(12) United States Patent
Chu et al.

(10) Patent No.: US 10,939,509 B2
(45) Date of Patent: Mar. 2, 2021

(54) RETURNED POWER FOR MICROWAVE APPLICATIONS

(71) Applicant: MicroCube, LLC, Fremont, CA (US)

(72) Inventors: Chun Yiu Chu, Oakland, CA (US); Dinesh I. Mody, San Jose, CA (US); Ketan Shroff, Pleasanton, CA (US); Amrish J. Walke, Milpitas, CA (US); Kirby Chiang, Los Altos, CA (US); Christopher Ah New, San Leandro, CA (US); Christine M. Tate, Sunnyvale, CA (US)

(73) Assignee: MicroCube, LLC, Fremont, CA (US)

( * ) Notice: Subject to any disclaimer, the term of this patent is extended or adjusted under 35 U.S.C. 154(b) by 683 days.

(21) Appl. No.: 15/256,259

(22) Filed: Sep. 2, 2016

(65) Prior Publication Data
US 2017/0118806 A1    Apr. 27, 2017

Related U.S. Application Data

(63) Continuation of application No. 13/854,673, filed on Apr. 1, 2013, now Pat. No. 9,462,642.
(Continued)

(51) Int. Cl.
  *H05B 6/64*    (2006.01)
  *H05B 6/70*    (2006.01)
  (Continued)

(52) U.S. Cl.
  CPC ....... *H05B 6/6447* (2013.01); *A61B 18/1815* (2013.01); *H05B 1/025* (2013.01);
  (Continued)

(58) Field of Classification Search
  CPC ........ H05B 6/6447; H05B 6/705; H05B 6/72; H05B 1/025; H05B 6/664; A61B 18/1815; A61B 2018/00267; A61B 2018/00642; A61B 2018/00785; A61B 2018/00875; A61B 2018/00755; A61B 2018/1846
  (Continued)

(56) References Cited

U.S. PATENT DOCUMENTS

| 5,364,392 A | 11/1994 | Warner et al. |
| 5,861,021 A | 1/1999 | Thome et al. |

(Continued)

FOREIGN PATENT DOCUMENTS

EP    2036512    3/2009

*Primary Examiner* — Quang T Van
(74) *Attorney, Agent, or Firm* — Levine Bagade Han LLP

(57) ABSTRACT

The present invention related to devices and methods that use returned power (RP) measurements during microwave energy delivery to perform one or more functions. For example, microwave devices and systems with one or more features to measure the returned microwave power. One or more measurements of the returned microwave power may be used to obtain information about one or more of: antenna shape, system status and system performance. One or more measurements of the returned microwave power shaping elements may also be used to obtain information about one or more properties of the target material. The invention also discloses devices and methods for delivering microwave energy to a variety of target materials to achieve a variety of desired microwave effects.

20 Claims, 22 Drawing Sheets

Related U.S. Application Data

(60) Provisional application No. 61/686,125, filed on Mar. 31, 2012.

(51) Int. Cl.
*A61B 18/18* (2006.01)
*H05B 1/02* (2006.01)
*H05B 6/72* (2006.01)
*H05B 6/66* (2006.01)
*A61B 18/00* (2006.01)

(52) U.S. Cl.
CPC ............ *H05B 6/664* (2013.01); *H05B 6/705* (2013.01); *H05B 6/72* (2013.01); *A61B 2018/00267* (2013.01); *A61B 2018/00642* (2013.01); *A61B 2018/00708* (2013.01); *A61B 2018/00755* (2013.01); *A61B 2018/00785* (2013.01); *A61B 2018/00875* (2013.01); *A61B 2018/1846* (2013.01)

(58) Field of Classification Search
USPC ....... 219/709, 748, 679, 750, 700, 701, 702, 219/690, 695, 697, 746; 422/21; 73/23.35; 95/87; 600/430; 607/101, 607/152, 154, 156
See application file for complete search history.

(56) References Cited

U.S. PATENT DOCUMENTS

| | | | |
|---|---|---|---|
| 6,067,475 A | 5/2000 | Graves et al. | |
| 6,471,696 B1 | 10/2002 | Berube et al. | |
| 7,197,363 B2 | 3/2007 | Prakash et al. | |
| 8,406,894 B2 * | 3/2013 | Johnson | A61N 5/04 607/101 |
| 2005/0199121 A1 * | 9/2005 | Crnko | G01N 30/30 95/87 |
| 2006/0287649 A1 | 12/2006 | Ormsby et al. | |
| 2007/0203480 A1 | 8/2007 | Mody et al. | |
| 2010/0121319 A1 | 5/2010 | Chu et al. | |
| 2010/0176123 A1 * | 7/2010 | Mihara | H05B 6/686 219/746 |
| 2011/0098697 A1 | 4/2011 | Braman | |
| 2011/0238054 A1 | 9/2011 | Kim et al. | |
| 2013/0041362 A1 | 2/2013 | Lee et al. | |
| 2013/0041365 A1 | 2/2013 | Rusin et al. | |
| 2013/0256302 A1 | 10/2013 | Chu et al. | |
| 2014/0352662 A1 * | 12/2014 | Serizawa | F02P 23/045 123/406.27 |
| 2014/0358140 A1 | 12/2014 | Emmons et al. | |

\* cited by examiner

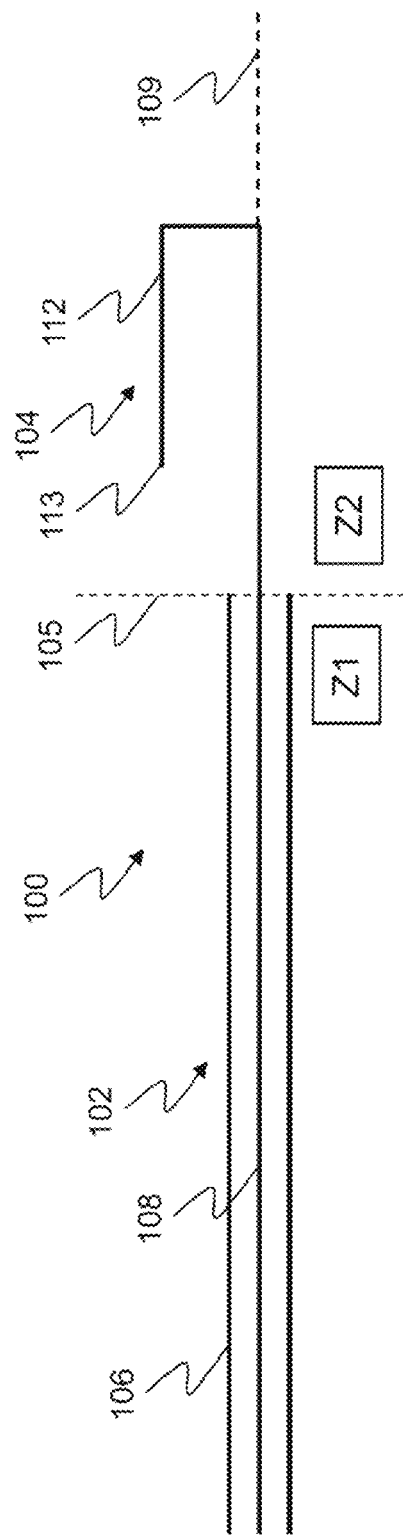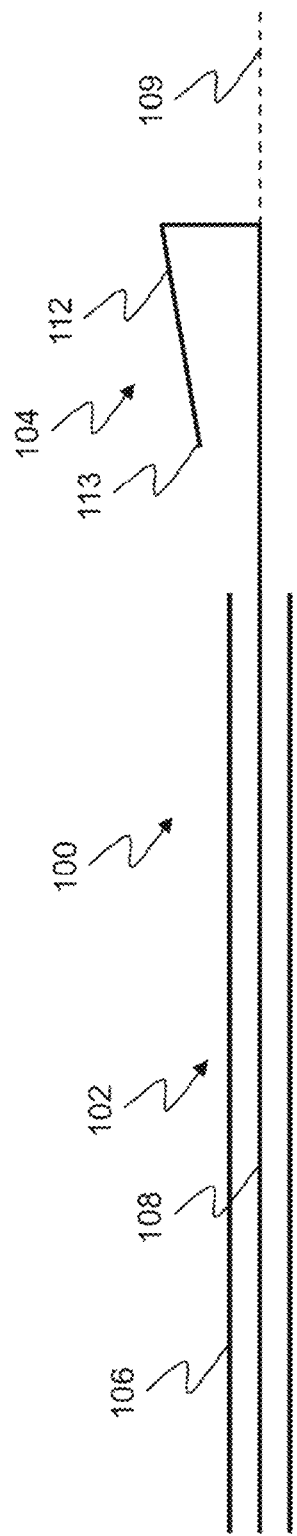
FIG. 1A
FIG. 1B

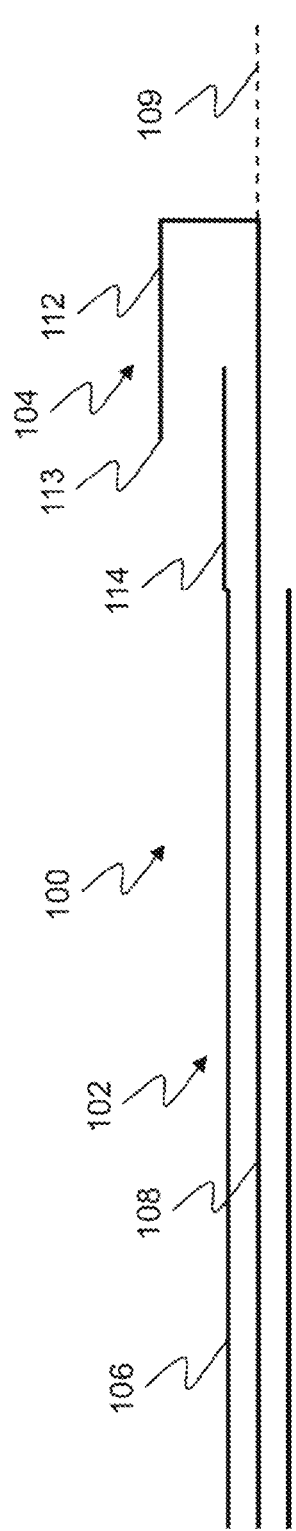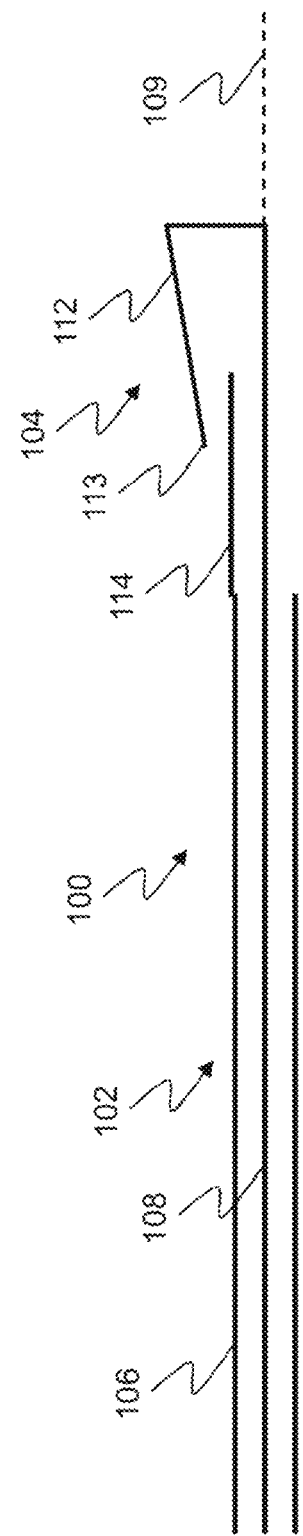

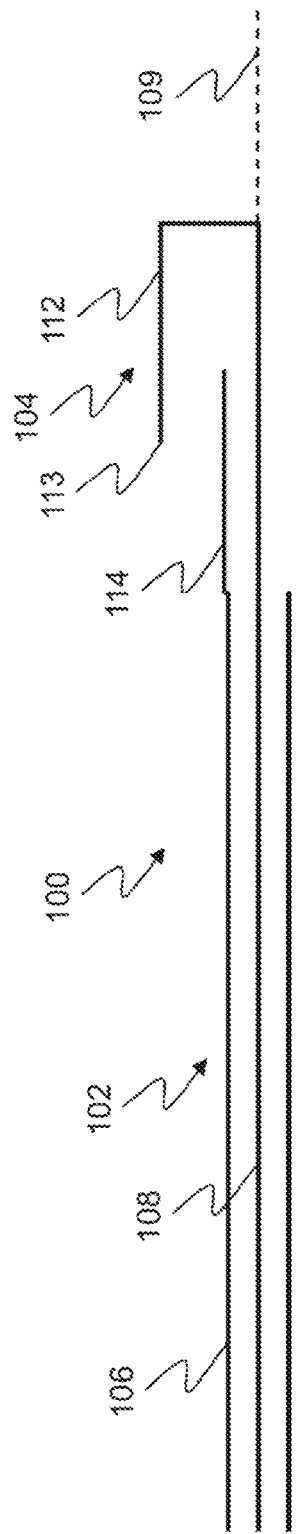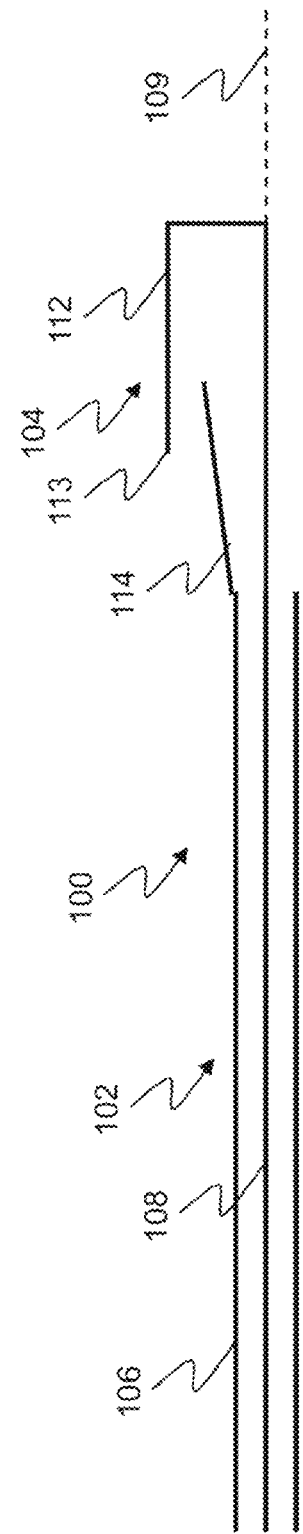

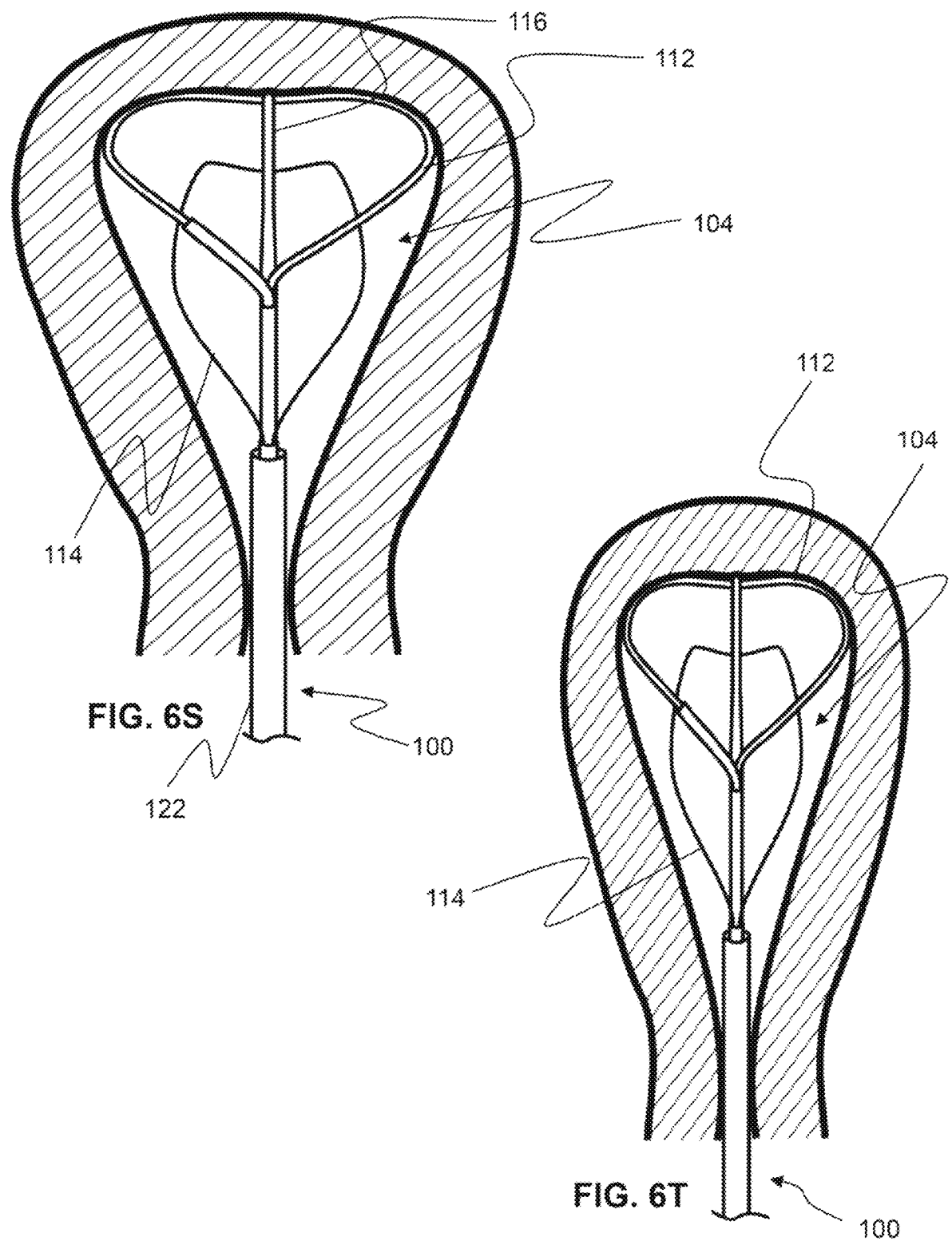

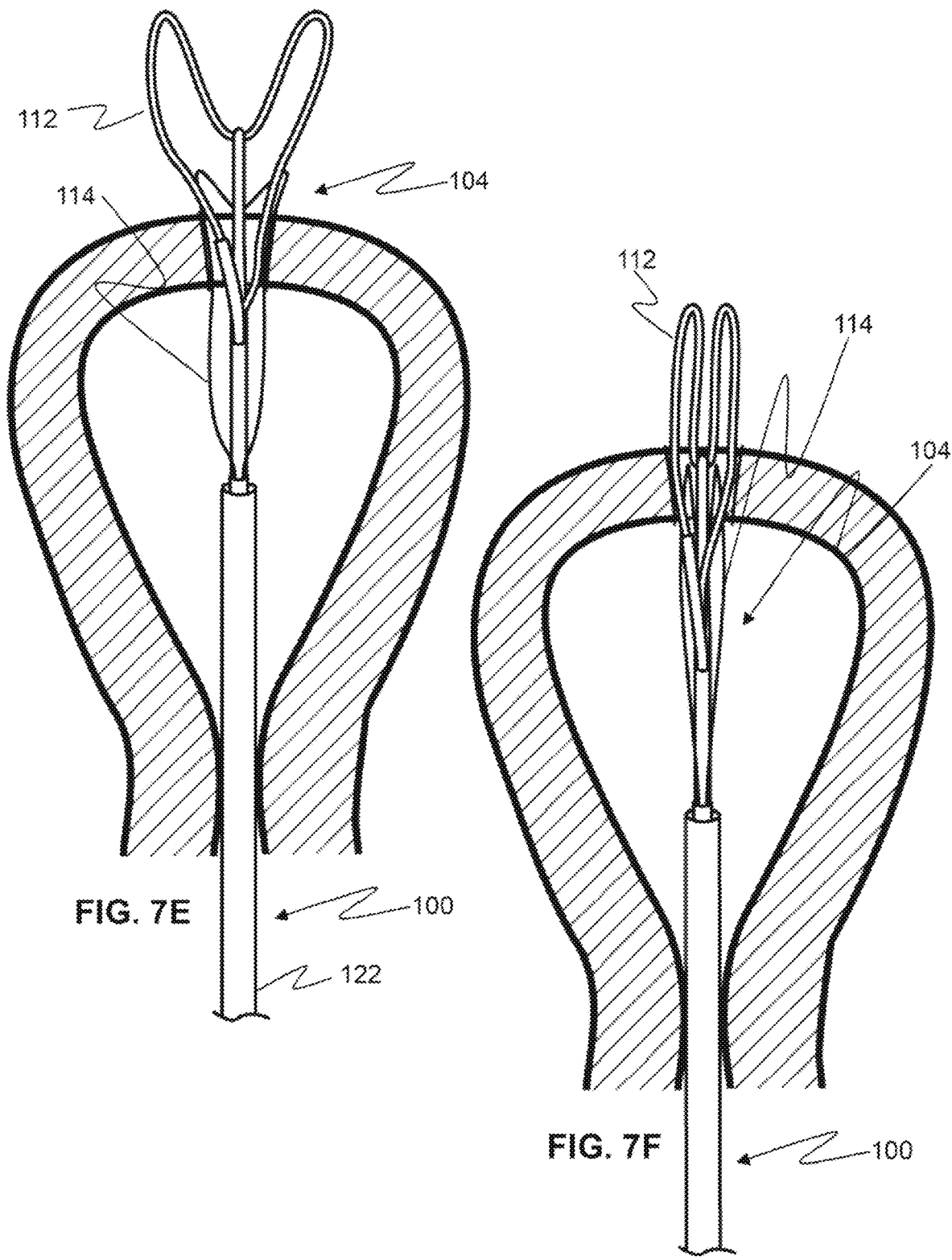

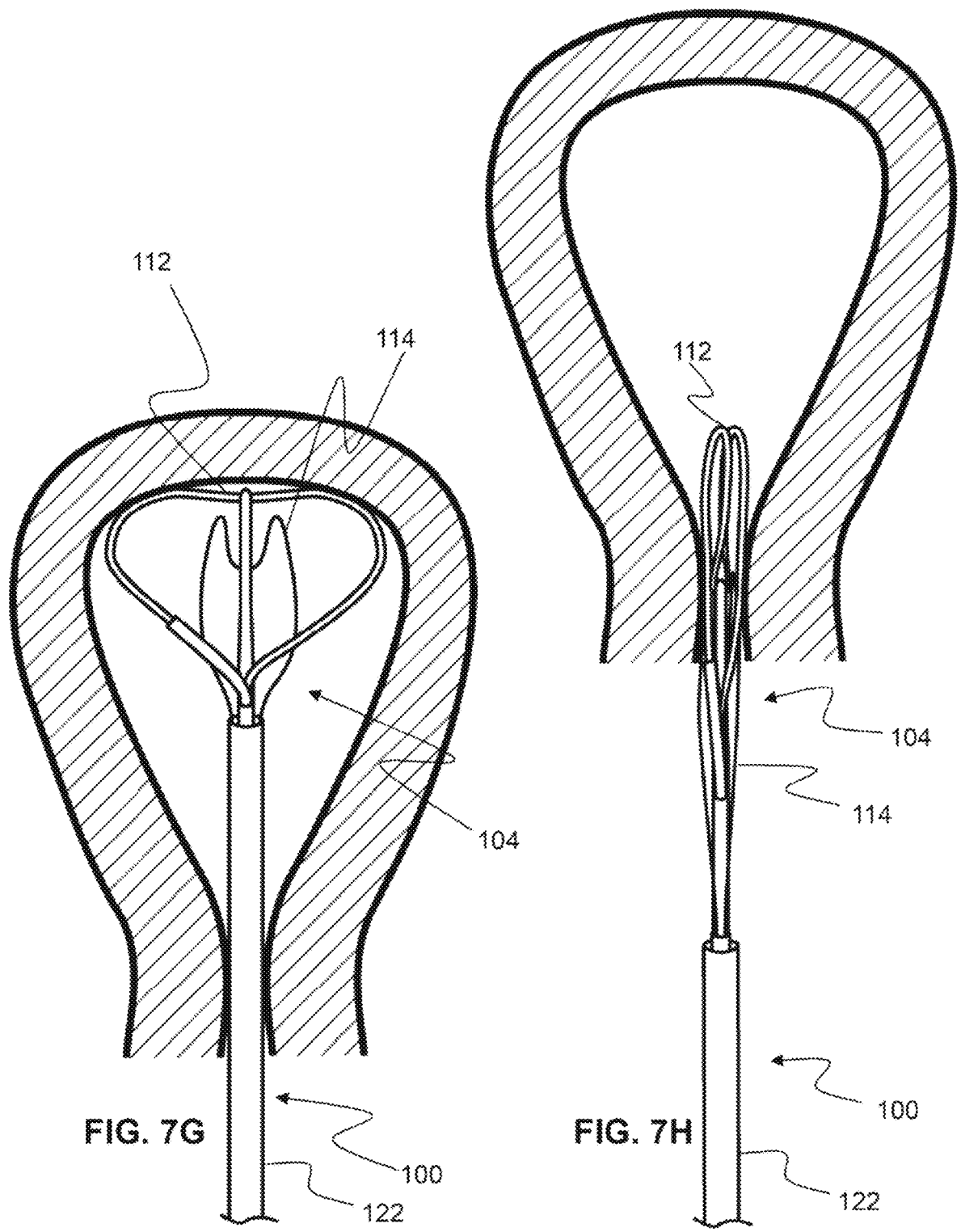

RETURNED POWER FOR MICROWAVE APPLICATIONS

CROSS-REFERENCE TO RELATED APPLICATION DATA

This application is a continuation of U.S. patent application Ser. No. 13/854,673 filed Apr. 1, 2013, which claims benefit of priority to U.S. Provisional Application No. 61/686,125, filed Mar. 31, 2012, both of which are incorporated by reference herewith in their entirety.

FIELD OF THE INVENTION

The present invention related to devices and methods that use returned power (RP) measurements during microwave energy delivery to perform one or more functions.

BACKGROUND

A typical microwave antenna designed for transmitting microwave energy comprises one or more metallic conductors that are electrically connected through a transmission line to a microwave generator. During use, the antenna acts as an impedance transformer between the microwave source and the medium to which the system is transmitting microwave energy. From a circuit perspective, the medium is equivalent to the load where the microwave energy from the microwave generator is ultimately deposited.

The antenna impedance is typically matched to the impedance of the microwave source to maximize the power transfer or minimize reflection of microwave power from the antenna and the medium. For a typical 50-ohm system, at the resonant frequency of the antenna, the antenna impedance presents itself to the transmission line as a pure 50-ohm resistance. At a frequency away from the resonant frequency, the antenna impedance can deviate from the pure resistance and can also have a reactance component: i.e. capacitance or inductance. Thus the system works most efficiently i.e. transmits maximum amount of power at the resonant frequency. During actual use, microwave generators typically generate microwave energy within a well defined frequency range (i.e. operating bandwidth). Therefore, antennas are typically designed such that the resonant frequency of the antenna is around this frequency range. Thus, any variation in the surrounding medium or the antenna itself during use can cause a sufficiently large change in the resonant frequency of the antenna such that the system performance deteriorates or otherwise changes.

Thus, there is a need for an improved design to avoid the problems described above. For example, an improved device and/or method can determine the change in variation in the surrounding medium or the antenna during use and use that information to take additional steps if necessary to improve delivery of microwave energy.

SUMMARY

This specification discloses multiple variations of antenna designs, systems, structures and devices, and associated methods, which illustrate various aspects of the invention. The various microwave antennas and the microwave engineering principles disclosed herein may be also used in a variety of industrial applications. For example, the near and/or far field of the microwave antennas disclosed herein may be used on target materials such as food, minerals, industrial products, semiconductors, etc. The near and/or far field of the microwave antennas disclosed herein may be used for data transmission and other communication, cooking or heating foods, in industrial processes for drying and curing products, in semiconductor processing and/or manufacturing (e.g. to generate plasma for processes such as reactive ion etching and plasma-enhanced chemical vapor deposition (PECVD)), during electrical or mechanical part manufacturing and/or testing and/or inspection, measuring the properties and/or dimensions of a medium surrounding an antenna, or simply to use the RP feedback to determine the configuration or shape of the antenna and/or the properties of the surrounding medium.

The present invention discloses embodiments of antennas that can optionally comprise one or more radiating elements and one or more shaping elements. During use, the shape of one or more radiating element(s) and/or one or more shaping element(s) may change relative to an antenna axis. This leads to a change in the position of the radiating element(s) and/or shaping element(s) relative to the surrounding medium, the distal region of a shielding element of a transmission line, antennas dielectrics (if any), floating conductors (if any) in the vicinity of radiating member, and other regions of radiating element(s) and/or shaping element(s). This in turn leads to a change in the electrical length of antenna due to the change in the interaction of the microwave energy emitted by one or more radiating element(s) with one or more of: the surrounding medium, the distal region of the shielding element, antenna dielectrics (if any), floating conductors (if any) in the vicinity of radiating member, shaping elements(s), and other regions of radiating element(s). The change in the electrical length of antenna and the corresponding change in the antenna impedance and the resonant frequency are detected by a change in the returned power (RP). The change in RP may be used to perform a variety of actions as disclosed in this specification.

The present invention also discloses embodiments wherein the properties of the surrounding medium change during the use of the antennas disclosed herein. This in turn leads to a change in the electrical length of antenna due to the change of signal speed/absorption and wavelength due to changes in one or more properties of the surrounding medium. The change in the electrical length of antenna and the corresponding change in the antenna impedance are detected by a change in the returned power (RP). The change in RP may be used to perform a variety of actions as disclosed in this specification.

The present disclosure also includes methods of providing microwave energy. For example, one such method can include introducing an antenna comprising a flexible radiating element into or adjacent to a target material; delivering microwave energy through the antenna to the target material; obtaining a returned power measurement of the antenna; and determining a change in an electrical length of the antenna using the returned power measurement and altering delivery of the microwave energy based on the change in electrical length.

In one variation, altering delivery of the microwave energy comprises repositioning the antenna to minimize deformation of the antenna. In some variations, obtaining the returned power measurement comprises obtaining a plurality of returned power measurements and where determining the change in the electrical length comprises determining a change in a shape of the radiating element.

In another variation a method can include delivering a test microwave energy to the target material, and where the method further comprises delivering a larger dose of microwave energy based on the returned power measurements of the test microwave energy.

In additional variations, the antenna is connected to a microwave generator and wherein obtaining the returned power measurement comprises measuring a magnitude of microwave energy returned to the generator and calculating the returned power measurement from the magnitude of the microwave energy returned to the generator; wherein calculating comprises dividing the returned power measured by the generator to the forward power measured by the generator.

Variations of the method include setting a returned power decision limit on a generator connected to the antenna, such that altering the delivery of the microwave energy occurs automatically if the returned power decision limit is met.

In additional variations, obtaining the returned power measurement occurs after changing a shape of the radiating element.

The method can also include using the returned power measurement to confirm proper deployment of the radiating element in the target material and where altering delivery of the microwave energy comprises repositioning the radiating element.

The returned power measurement can be used to confirm proper deployment of the antenna in the target material and where altering delivery of the microwave energy comprises repositioning the antenna. Alternatively, or in addition, the returned power measurement can be used to obtain feedback about a property of the target material. In some variations, the returned power measurement is used to terminate microwave energy delivery.

The antenna can further a shaping element, and wherein the change in electrical length of is due to the change in the interaction of the microwave energy emitted by the radiating element with the shaping element.

In another variation, the disclosure includes systems for delivering microwave energy. One variation of such a system a transmission line comprising a shielding element, an antenna comprising a flexible radiating element connected to the transmission line, wherein the system comprises a linear antenna axis parallel to and emerging from the distal end of the transmission line, a generator adapted to generate microwave energy; wherein the generator is configured to obtain a returned power measurement of the antenna to determine a change in the electrical length of the antenna due to a change in a physical configuration of the flexible radiating element relative to the antenna axis.

Variations of the system include a controller configured to determine the change in the electrical length of the antenna due to the change in an orientation, position, and/or relationship of the element to the antenna axis. The controller can also be configured to adjust a parameter of an output of the microwave energy based on the returned power measurement.

Another variation includes a controller configured to adjust the parameter of the output of the microwave energy based on the returned power measurement and a returned power limit. The controller can also be configured for impedance matching of the antenna based on the returned power measurement.

In another variation, the present disclosure includes a system for providing microwave energy, comprising an antenna comprising a flexible radiating element configured for placement into or adjacent to a target material; a microwave energy controller configured to deliver microwave energy through the antenna to the target material; the microwave energy controller configured to obtain a returned power measurement of the antenna and to determine a change in an electrical length of the antenna using the returned power measurement to permit altering delivery of the microwave energy based on the change in electrical length.

BRIEF DESCRIPTION OF THE FIGURES

FIGS. 1A and 1B show a schematic view of an embodiment of a microwave device of the present invention having a microwave antenna comprising a flexible radiating element.

FIGS. 1C-1D show two configurations of an antenna comprising a flexible radiating element and one or more shaping elements.

FIGS. 1E-1F show two configurations of an antenna comprising a radiating element and one or more flexible shaping elements.

FIGS. 6S and 6T show an antenna deployed in two target regions of different dimensions

FIGS. 7E-7H show embodiments of mis-deployed antennas wherein at least one of: radiating member and shaping member are mis-deployed.

DETAILED DESCRIPTION

Figure 2:
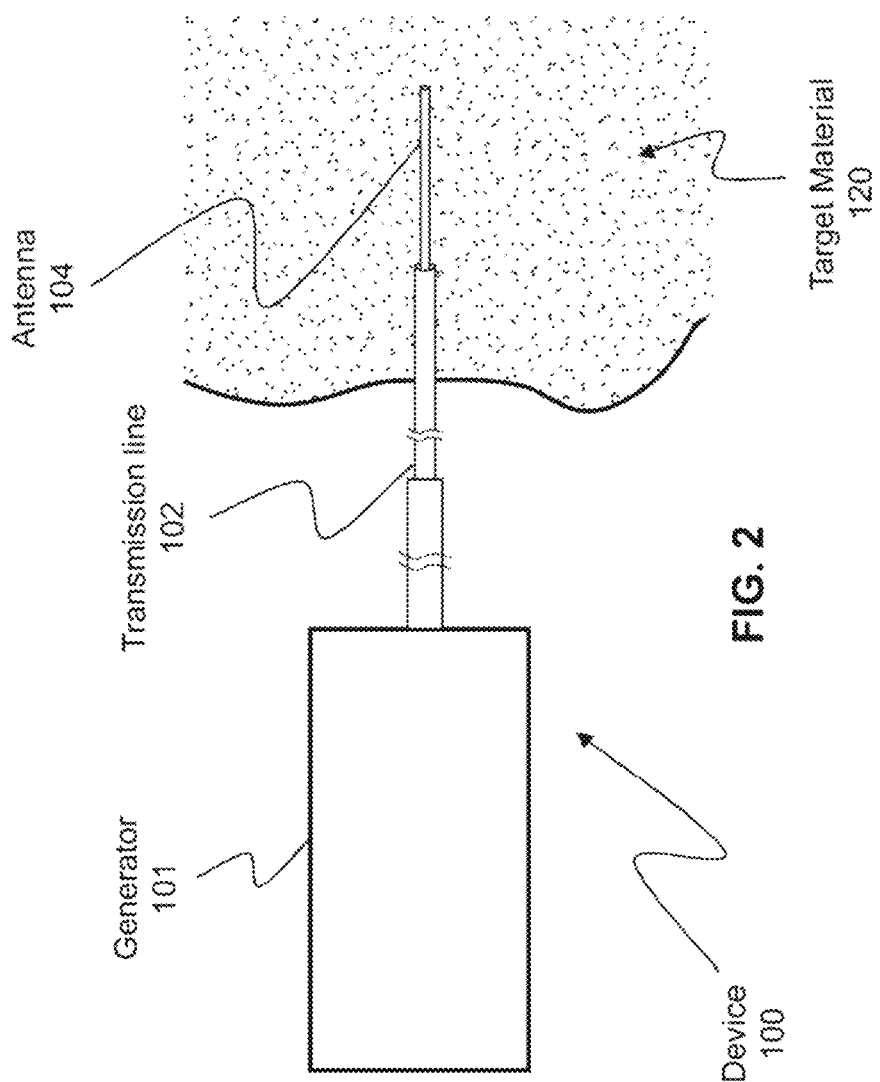
FIG. 2 shows a typical embodiment of a microwave device and method.

This specification discloses multiple antenna designs, systems, structures and devices, and associated methods, which illustrate various aspects of the invention. While these systems, structures and devices, and associated methods, are discussed primarily in terms of some particular antenna designs and some representative target materials, the methods and devices disclosed herein are applicable for use in other antenna and system designs as well as other target materials too.

FIGS. 1A and 1B show a schematic view of an embodiment of a microwave device 100 having a microwave antenna 104 comprising a flexible radiating element 112. In FIG. 1A, microwave device 100 comprises a transmission line such as a coaxial cable 102. An antenna 104 is connected to the distal end of coaxial cable 102. FIG. 1A shows microwave device 100 divided into a first zone Z1 and a second zone Z2 by an imaginary transition line 105. First zone Z1 is proximal to second zone Z2. Transition line 105 is defined by the distal end of coaxial cable 102 and is substantially perpendicular to the axis of coaxial cable 102 at the distal end of coaxial cable 102. In the embodiment shown in FIG. 1A, the distal region of coaxial cable 102 lies entirely within first zone Z1 and antenna 104 lies entirely within second zone Z2. When a microwave signal is fed to antenna 104 through coaxial cable 102, antenna 104 generates a microwave field.

Several of the embodiments disclosed herein use a characteristic parameter of the antenna called the electrical length of an antenna, a parameter that is in general, different from its physical length. Factors that can determine the electrical length of an antenna include: length of the conductor, diameter of the conductor, presence of nearby metal objects, shape of the conductor, one or more dielectrics on the conductor, surrounding medium, etc. The antenna impedance is related to the electrical length of the antenna at the frequency in use. In FIG. 1A, antenna 104 comprises a radiating element 112 which may be made of a variety of electrically conductive materials e.g. metals, conductive polymers, materials with embedded conductive particles, etc. The electrical length of radiating element 112 is dependent on a variety of factors including, but not limited to: the physical length of radiating element 112, the shape of radiating element 112, the material(s) used to construct shaping element 112, presence of one or more antenna dielectrics 116 in antenna 104, variation of the cross-sectional profile along the length of shaping element 112, presence of conductive element(s) within antenna 104 and the proximity of radiating element 112 with the distal region of transmission line 102, etc. In a preferred embodiment, the electrical length of radiating element 112 is an odd multiple of one quarter of the effective wavelength of the microwave energy input from the transmission line 102. Since the electrical length of radiating element 112 is a factor of the antenna impedance, any change in the electrical length of radiating element 112 may change the antenna impedance sufficiently to cause deterioration in the performance of antenna 104. This is explained in the examples shown in FIGS. 1A-1F.

In the embodiments of FIGS. 1A-1F, when microwave energy is delivered through coaxial cable 102 to antenna 104, a characteristic microwave field is emitted by radiating element 112. The microwave field interacts with the surrounding structures such as the surrounding medium, the distal region of shielding element 106, shaping elements 114 (if any), antennas dielectrics 116 (if any), floating conductors (if any) in the vicinity of radiating member 112, and other regions of radiating element 112. The interaction of this microwave field with conductive objects such as the distal region of shielding element 106, shaping elements 114, floating conductors in the vicinity of radiating member 112, and other regions of radiating element 112 induces a leakage current on those metallic objects. The leakage current in turn creates a second microwave field. The interaction of the characteristic microwave field emitted by radiating element 112 with the surrounding structures, especially surrounding conductive objects determines the characteristic electrical length of the antenna 104. Since a microwave field couples to the nearest conductive path, the interaction of the characteristic microwave field emitted by radiating element 112 with the shielding element 106 of the transmission line (e.g. the outer conductor 106 of the feeding coaxial cable 102) and any shaping elements 114 electrically connected to the shielding element 106 is especially important in determining the effective electrical length of antenna 104.

In FIG. 1B, the shape of radiating element 112 changes from the shape in FIG. 1A. The shape change is defined relative to an antenna axis 109 defined as a linear axis parallel to and emerging from the distal end of the transmission line 102. In FIG. 1A, radiating element 112 is in an axially expanded configuration or shape and in FIG. 1B, radiating element 112 is in an axially compressed configuration or shape. This shape change leads to a change in the position of the radiating element 112 relative to the surrounding medium, the distal region of shielding element 106, antennas dielectrics 116 (if any), floating conductors (if any) in the vicinity of radiating member 112, and other regions of radiating element 112. This in turn leads to a change in the electrical length of antenna 104 due to the change in the interaction of the microwave emitted by the radiating element 112 with one or more of: the surrounding medium, the distal region of shielding element 106, antennas dielectrics 116 (if any), floating conductors (if any) in the vicinity of radiating member 112, and other regions of radiating element 112. The change in the electrical length of antenna 104 and the corresponding change in the antenna impedance are detected by a change in the RP.

FIGS. 1C-1D show two configurations of an antenna 104 comprising a flexible radiating element 112 and one or more microwave field shaping elements 114. When microwave energy is delivered through coaxial cable 102 to antenna 104, a characteristic microwave field is emitted by radiating element 112. The microwave field interacts with the surrounding structures such as the surrounding medium, the distal region of shielding element 106, one or more shaping elements 114, antennas dielectrics 116 (if any), floating conductors (if any) in the vicinity of radiating member 112, and other regions of radiating element 112. In antenna 104, the nearest conductive path is provided by shaping element 114. Since a microwave field couples to the nearest conductive path, the interaction of the characteristic microwave field emitted by radiating element 112 with any shaping elements 114 electrically connected to the shielding element 106 and the shielding element 106 of the transmission line (e.g. the outer conductor 106 of the feeding coaxial cable 102) is especially important in determining the effective electrical length of antenna 104.

In FIG. 1D, the shape of radiating element 112 has been changed from the shape in FIG. 1C. The shape change is defined relative to an antenna axis 109 defined as a linear axis parallel to and emerging from the distal end of the transmission line 102. In FIG. 1C, radiating element 112 is in an axially expanded configuration or shape and in FIG. 1D, radiating element 112 is in an axially compressed configuration or shape. This shape change leads to a change in the position of the radiating element 112 relative to the shaping element 114, the surrounding medium, the distal region of shielding element 106, antennas dielectrics 116 (if any), floating conductors (if any) in the vicinity of radiating member 112, and other regions of radiating element 112. This in turn leads to a change in the electrical length of antenna 104 due to the change in the interaction of the microwave field emitted by the radiating element 112 with one or more of: the shaping element 114, the surrounding medium, the distal region of shielding element 106, antennas dielectrics 116 (if any), floating conductors in the vicinity of radiating member 112 (if any), and other regions of radiating element 112. The change in the electrical length of antenna 104 and the corresponding change in the antenna impedance are detected by a change in the returned power (RP).

FIGS. 1E-1F show two configurations of an antenna 104 comprising a radiating element 112 and one or more flexible shaping elements 114. When microwave energy is delivered through coaxial cable 102 to antenna 104, a characteristic microwave field is emitted by radiating element 112. The microwave field interacts with the surrounding structures such as the surrounding medium, the distal region of shielding element 106, one or more shaping elements 114, antennas dielectrics 116 (if any), floating conductors (if any) in the vicinity of radiating member 112, and other regions of radiating element 112. In antenna 104, the nearest conductive path is provided by shaping element 114. Since a microwave field couples to the nearest conductive path, the interaction of the characteristic microwave field emitted by radiating element 112 with any shaping elements 114 electrically connected to the shielding element 106 and the shielding element 106 of the transmission line (e.g. the outer conductor 106 of the feeding coaxial cable 102) is especially important in determining the effective electrical length of antenna 104.

In FIG. 1F, the shape of shaping element 114 has been changed from the shape in FIG. 1E. The shape change is defined relative to an antenna axis 109 defined as a linear axis parallel to and emerging from the distal end of the transmission line 102. In FIG. 1C, shaping element 114 is in an axially compressed configuration or shape and in FIG. 1D, shaping element 114 is in an axially expanded configuration or shape. This shape change leads to a change in the position of the shaping element 114 relative to the radiating element 112, surrounding medium, the distal region of shielding element 106, antennas dielectrics 116 (if any), and floating conductors (if any) in the vicinity of radiating member 112. This in turn leads to a change in the electrical length of antenna 104 due to the change in the interaction of the microwave energy emitted by the radiating element 112 with shaping element 114. The change in the electrical length of antenna 104 and the corresponding change in the antenna impedance are detected by a change in the returned power (RP).

In other embodiments, the shapes of both radiating element 112 and shaping element(s) 114 may change relative to an antenna axis 109 defined as a linear axis parallel to and emerging from the distal end of the transmission line 102. This shape change leads to a change in the electrical length of antenna 104 due to the change in the interaction of the microwave energy emitted by the radiating element 112 with one or more of: the surrounding medium, the distal region of shielding element 106, antennas dielectrics 116 (if any), floating conductors (if any) in the vicinity of radiating member 112, and other regions of radiating element 112. The change in the electrical length of antenna 104 and the corresponding change in the antenna impedance are detected by a change in the returned power (RP). Any of the changes in RB described herein can be used to perform a variety of actions as disclosed elsewhere in this specification.

FIG. 2 shows a typical embodiment of a microwave device and method. In a typical embodiment of a microwave device and method, microwave energy is delivered to device 100 from generator 101 through a suitable transmission line 102. The microwave energy output of generator 101 (called forward power or incident power), passes through transmission line 102, through the shaft of device 100 and ultimately to the antenna 104. Antenna 104 delivers a portion of the microwave energy to target material 120. Due to the nature of microwave physics, a portion of the forward power is returned back towards generator 101 from various points in the system. This portion is called returned power (RP). In the present invention, one or more parameters based on the RP are measured and/or calculated and used for taking user level or system level decisions.

In the present specification, RP is defined as one or more primary or derived parameters or combination thereof of the microwave energy returned towards the microwave energy source (e.g. generator 101) at one or more times during a procedure as described below.

In one embodiment, RP is calculated as a fraction by dividing the returned power (e.g. as measured by power detector 122) by the forward power (e.g. as measured by power detector 122). i.e. RP=(Returned Power)/(Forward Power). This returned power fraction may then be used to take one or more user level or system level decisions.

In one embodiment, the magnitude of the returned power is measured (e.g. in Watts). E.g. the average returned power may be measured. This returned power magnitude may then be used to take appropriate user level or system level decisions.

The returned power may be measured one or more times before the start of a microwave energy based procedure and/or during the microwave energy based procedure and/or after the end of the microwave energy based procedure. The returned power may be measured continuously during one or more periods of time or may be measured intermittently.

Figure 3:
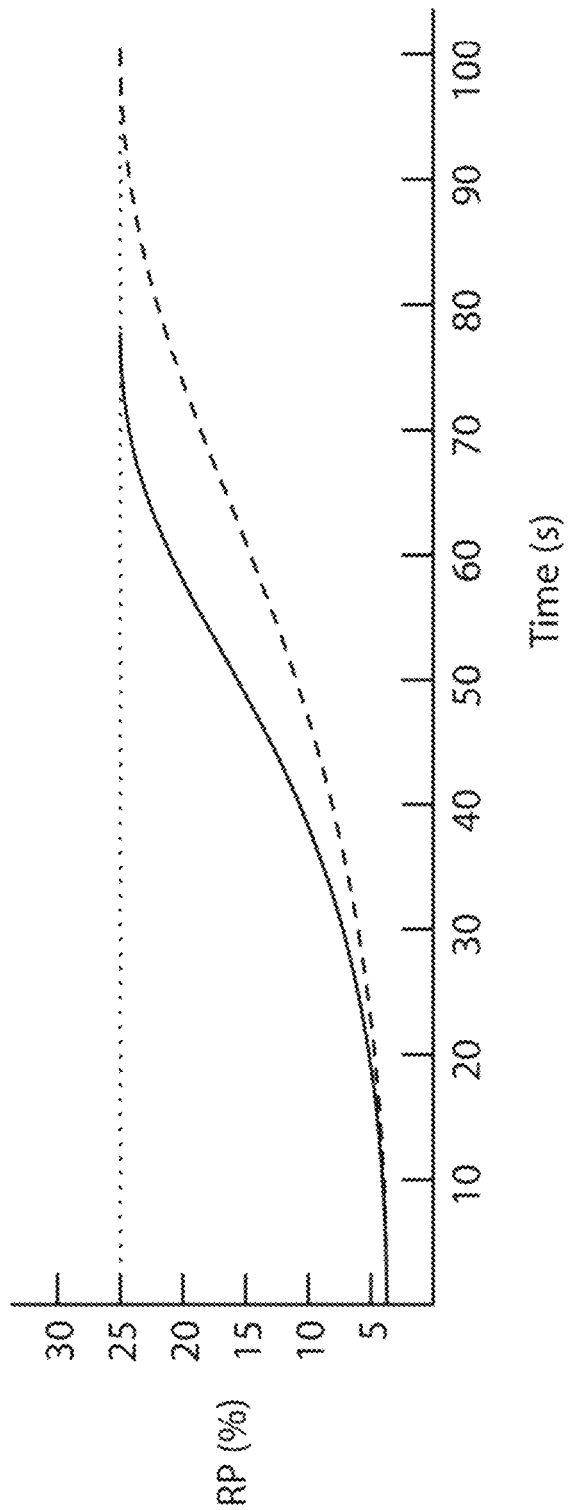
FIG. 3 shows a graph of RP versus time for two embodiments of microwave energy delivery.

In one embodiment, as shown in FIG. 3, a graph of returned power with a second parameter is calculated and/or displayed on a screen. Examples of such second parameters include, but are not limited to: time, antenna 104 and/or device 100 positions within target material 120, various deployment configurations of antenna 104, In one such embodiment, a graph of returned power with time is recorded and/or displayed on a screen. In another such embodiment, a graph of returned power with position of antenna 104 is recorded and/or displayed on a screen.

In embodiments wherein the change in returned power with a second parameter is calculated and/or displayed, one or more data processing steps may be performed on the returned power measurements. Examples of such data processing steps include, but are not limited to: calculating the trend of the returned power with the second parameter, calculating the first derivative i.e. the slope of the returned power, calculating the second or higher derivatives of the returned power, calculating the area-under-the-curve of the returned power.

In a further embodiment, the measured returned power is adjusted for expected microwave energy losses. Examples of such losses include, but are not limited to: losses encountered within generator 101 after the forward power is measured by a power meter, losses encountered within transmission line 102, losses encountered within shaft of device 100, losses encountered within antenna 104, reflections occurring at one or more interfaces from the point forward power is measured till the interface between the antenna and the shaft of device 100, expected measurement errors while measuring forward power and/or returned power, etc. The adjusted returned power is then used to take appropriate user level or system level decisions.

In one embodiment, the expected microwave energy losses are estimated after positioning antenna 104 inside a test material (e.g. saline or water). The test material may be chosen such that it simulates actual target material. The returned power measurements made after delivering microwave energy inside the test material can then be correlated with the expected microwave energy losses when antenna 104 is positioned inside the actual target material. In one embodiment, the test material is a microwave energy sink physically located inside the microwave generator 101 and the transmission line 102 is directly connected to a port connected to the test material to test one or more of: generator 101, transmission line 102 and any system connections as per the embodiments disclosed elsewhere in this specification.

In an additional embodiment, a lower level of microwave energy called test power is delivered and the corresponding RP is measured. This test power is low enough to not cause any appreciable microwave energy based changes in the target material. The returned power from the test power is used to take appropriate user level or system level decisions. In one such embodiment, the delivery and measurement of test power is done (one or more times) before and/or after one or more periods of typical microwave energy delivery. In another embodiment, the test power is delivered such that the total energy delivered is <20 J. In another embodiment, the delivery and measurement of test power is done (one or more times) intermittently in between periods of typical microwave energy delivery. In one embodiment, the test power is delivered as a pulse of a small pulse width (e.g. <1 s). In one embodiment, the magnitude of the test power is gradually increased or ramped up over a period of time (e.g. 3 s).

One or more statistical analyses of the returned power measurements may be made. Examples of simpler statistical analysis of RP measurements include, but are not limited to estimating one or more of: maximum, minimum, average, median, mode, standard deviation, etc. of the one or more measured values. The statistical analysis may be performed by comparing the actual RP value with previously stored or separately generated RP values. One or more trendlines may be plotted for one or more RP measurements. Examples of types of such trendlines include, but are not limited to: linear, logarithmic, power, polynomial, exponential, and moving average. The data from one or more RP measurements may be filtered using one or more filtering criteria. Examples of more complex statistical analysis of RP measurements include, but are not limited to a) determining the R (correlation coefficient) value to measure of the strength of linear dependence between RP measurements and a second parameter, b) R.exp.2 (coefficient of determination) to predict outcomes on the basis of other related information, etc.

In one embodiment, one or more additional parameters such as data obtained from one or more sensors are used in addition to data from one or more RP measurements to take one or more decisions. Examples of such additional parameters include, but are not limited to: temperature measurements, pressure measurements, electrical measurements at one or more regions, direct or machine aided visualization of the target material or one or more components of the system, data from a visual display, pre-existing data, etc.

One or more decision levels or limits may be used to take user level or system level decisions. In one embodiment, one or more decision levels or limits (e.g. one or more of 20%, 25%, 30%, 45%, etc.) are pre-programmed in the system software and/or hardware.

In another embodiment, one or more decision levels or limits are set either by a user or by the system based on defined criteria e.g. initial RP measurements, properties of the target material, etc. In one embodiment, the user inserts device 100 into the target material. Thereafter, a test microwave power is delivered and the returned power is measured. This returned power level is then used by the system and/or the user to set the one or more decision levels or limits for taking user level or system level decisions.

In another embodiment, one or more decision levels or limits are based on one or more initial measurements of RP. For example, a first measurement is made before an energy delivery cycle to get an initial RP level. This initial RP level is then used to determine one or more decision levels or limits. In one such embodiment, the system automatically prevents energy delivery energy delivery if the initial RP level is above a threshold.

In another embodiment, one or more decision levels or limits are based on the size of the target material. E.g. the size of the object or an anatomical organ to be treated. In one such embodiment, a higher RP limit is used for treating a larger target material to allow more energy delivery to the larger anatomy.

In another embodiment, one or more decision levels or limits are based on the shape of the target material.

In another embodiment, one or more decision levels or limits are based on the desired outcome of the energy delivery. In one such embodiment of endometrial ablation, a first set of one or more decision levels or limits are used when reduction in menstruation rather than amenorrhea is the desired outcome and a second set of one or more decision levels or limits are used when amenorrhea rather than reduction in menstruation is the desired outcome. In one such embodiment, one or more decision levels or limits and the energy delivery settings are used to automatically limit ablation depth to 1-4 mm beyond the endo-myometrial junction. In one such embodiment, the energy delivery settings are set to deliver a generator output dose ranging between 2,500-5,000 J.

In another embodiment, one or more decision levels or limits are based on the desired clinical condition to be treated. In one such embodiment of uterine ablation, a first set of one or more decision levels or limits are used for treating adenomyosis and a second set of one or more decision levels or limits are used for treating hyperplasia.

In another embodiment, one or more decision levels or limits are based on the desired depth of penetration of the microwave energy or the desired size of the thermal zone created using the microwave energy.

In another medical embodiment, one or more decision levels or limits are based on the pre-procedure measurements of one or more regions of the anatomy. Such pre-procedure measurements may be made using a variety of imaging tools (e.g. endoscopy, ultrasound imaging, direct mechanical measurement of one or more anatomical regions, etc.

In one embodiment, the energy delivery is adjusted in real time based on one or more or RP parameters and procedure feedback. Examples of RP parameters include, but are not limited to: total increase in RP, rate of increase of RP (e.g. unexpectedly sharp increase, unexpectedly slow increase, etc.) and other RP parameters as disclosed elsewhere in this specification. Examples of procedure feedback include, but are not limited to: pain experienced by the patient, imaging feedback about the progress of the procedure, change in a patient parameter, etc.

The following are embodiments of the timing of RP measurement(s). In one embodiment, RP is measured before or at the start of actual microwave energy delivery. The RP may be measured once or multiple times or continuously till a desired RP level is obtained. Thereafter, the delivery of power may be started.

In one embodiment, RP is measured during one or more device movements. The device may be subjected to one or more movements including, but not limited to:

adjusting the position of the device 100 and/or antenna 104 relative to a target material, deploying and/or undeploying antenna 104 into the target, turning or twisting the device 100 and/or antenna 104, engaging a steering or deflecting mechanism that steers or deflects device 100 and/or antenna 104, In one embodiment, RP is measured during a procedure of delivering microwave power. The measurements may be continuous or discreet. In one embodiment, microwave energy is delivered discontinuously and the measurements are made during one or more of microwave "on" times and microwave "off" times.

Similarly, RP may be measured after a procedure of delivering microwave power. This may be used for example to obtain feedback about the device 100 and/or the procedure.

In one embodiment, RP is measured after altering antenna 104. In one such embodiment, the shape of antenna 104 is altered and the returned power is measured before and/or during and/or after changing the shape of antenna 104. The shape of the antenna 104 may be altered by one or more of: twisting the antenna 104, engaging a shape altering mechanism that alters the shape of antenna 104, partially or completely deploying or undeploying antenna 104 The level and/or the change in the level of RP with the amount of alteration of antenna 104 may be measured and used to take further decisions.

In one embodiment, RP is measured after altering the local environment around antenna 104. In one such embodiment, a fluid (e.g. a liquid or gas) is introduced around one or more regions of antenna 104. The fluid environment may alter (e.g. improve or worsen) the matching between antenna 104 and the surrounding target material. The level and/or the change in the RP with the amount of alteration of the local environment around antenna 104 may be measured and used to take further decisions.

Any information about the RP in any of the embodiments disclosed herein may be used to alert the user or may be fed back into the generator to take one or more decision. The user can be alerted by one or more of: sounding an alarm, displaying the RP measurement(s), sending information to another device, and displaying one or more derived parameters of the RP such as a graph of RP against a secondary parameter.

FIG. 3 shows a graph of RP versus time for two embodiments of microwave energy delivery. In the graph with the solid line, the RP increases rapidly as the energy is delivered reaching the RP limit of 25% around the 80 s mark. This will cause a certain amount of microwave energy dose to be delivered to the target material. However, in certain situations, a greater dose of microwave energy might need to be delivered. In the graph with the dashed line, the microwave energy output to the target material is controlled (e.g. automatically by the system or manually by the user) based on the feedback of the graph of RP versus time. In one such embodiment, the microwave power may be lowered if the rate of increase of RP is greater than expected for achieving one or more of: preventing charring or material desiccation, maintaining the temperature of the medium surrounding antenna 104, and maintaining the temperature of antenna 104 or other system components. The lowering of microwave power level may allow the procedure to continue for a longer time with a consequential increase in the total energy dose. In one embodiment, the microwave power may be increased if the RP increase is lower than expected to enable a faster procedure even while delivering a desired energy dose. A faster procedure saves time by reducing the total duration of the procedure.

Figure 4A:
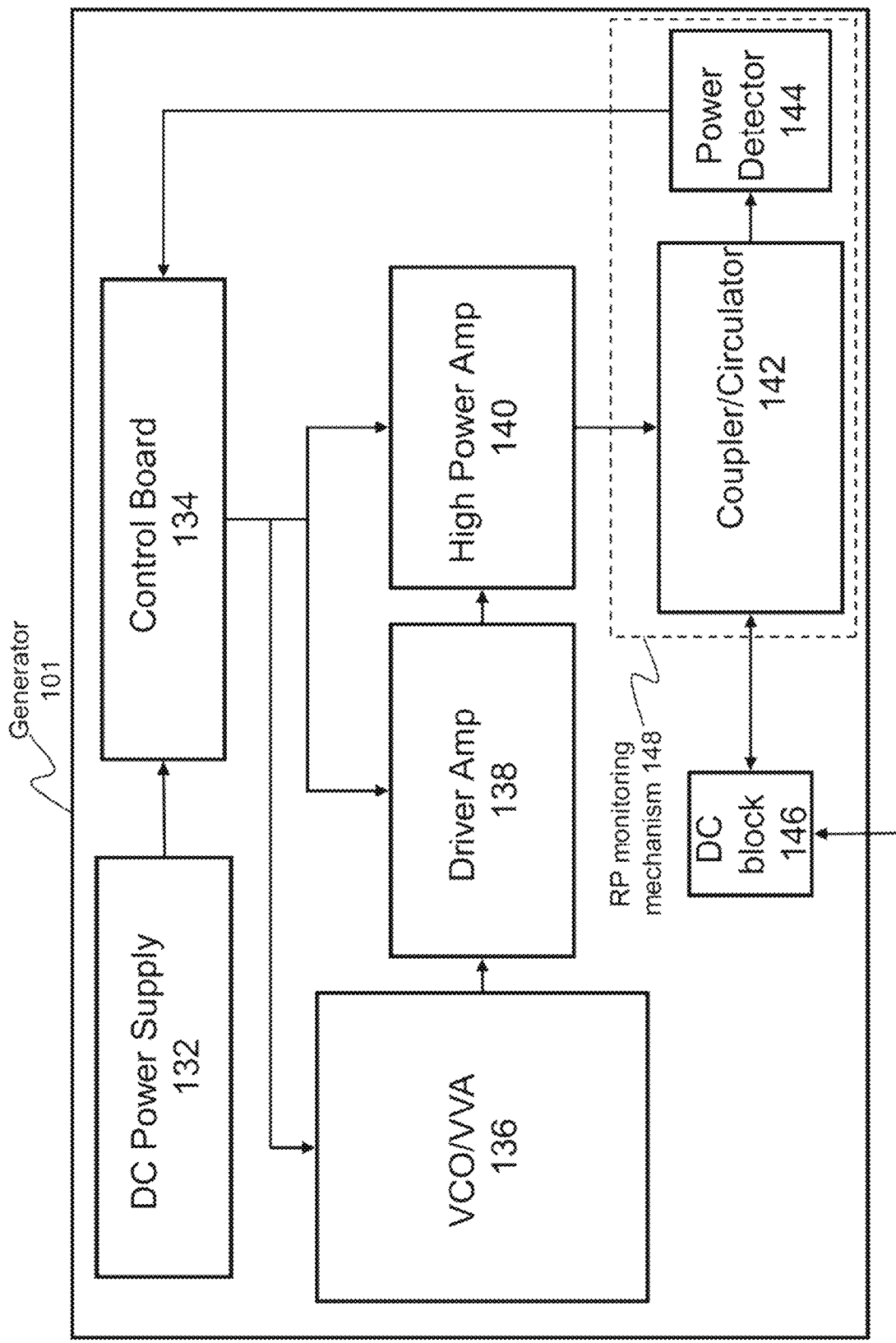
FIG. 4A shows one embodiment of a microwave generator of the present invention.

In one embodiment, the variation of RP versus time is used to deliver microwave energy at a power setting that raises the temperature of a target to a desired level and thereafter delivers microwave energy at a lower power setting to maintain the temperature of the target at the desired level FIG. 4A shows one embodiment of a microwave generator 101 of the present invention. Microwave generator 101 comprises a DC power supply 132, a control board 134, a VCO/VVA (Voltage-Controlled Oscillator/Voltage Variable Attenuator) module 136, a driver amplifier 138, a high power amplifier 140, a coupler/circulator module 142, a power detector 144 and a DC block 146. In this embodiment, DC power supply 132 supplies DC power to control board 134. Control board 134 in turn sends controlled amount of DC power to VCO/VVA module 136, driver amplifier 138 and high power amplifier 140. VCO/VVA module 136 generates microwave energy using the DC power. The microwave energy is sent to the driver amplifier 138 which in turn amplifies the microwave signal and feeds it to high power amplifier 140. The amplified microwave signal is then fed to coupler/circulator module 142 and thereafter is filtered using a DC block 146 that filters out any DC signals. The filtered microwave energy is then transmitted out of generator 101. In any of the microwave generators 101 used for any of the embodiments herein, information of one or more RP parameters measured at any location may be fed to the control board 134. Control board 134 may thereafter use the RP information to control the working of one or more of: VCO/VVA (Voltage-Controlled Oscillator/Voltage Variable Attenuator) module 136, a driver amplifier 138, a high power amplifier 140, and an impedance matching mechanism 150.

An example of a component that can be used to build DC power supply 132 is Condor GPMP900 series 900 W at 28V. Examples of components that can be used to build VCO are ROS-928C-19+, ROS-1340-119+ and CVCO55CL. Examples of components that can be used to build VVA are RVA-2500 and SVA-2000+. Examples of transistor components that can be used to build driver amplifier 138 are Sirenza XDO10-51S-D4F and Freescale MWIC930NR1. Examples of transistor components that can be used to build high power amplifier 140 are NXP BLF6G 10Ls-200R, Infineon PTF082001E and Freescale MRFE6S9135HR3. Examples of components that can be used to build circulator are M2Global 900-824960-501, Start Microwaves GDC-0094 and RF&NoiseComponents DC-910-154. An example of a component that can be used to build DC block 146 is HR-21/22. Power detector 144 may comprises a diode detector. Examples of such diode detectors include, but are not limited to: ResNet 8P2 and Broadwave 851-096-POS.

In one embodiment, generator 101 comprises a RP monitoring mechanism 148 for monitoring the amount of microwave energy that is returned back to the generator 101 during use. In one embodiment, the returned power monitoring mechanism 148 comprises coupler/circulator module 142 and power detector 144 that interfaces with control board 134. Coupler/circulator module 142 comprises a pair of couplers and a circulator. A first coupler is used to divert a small portion (e.g. <1%) of the incident power to a first power detector 144. A second coupler is used to divert a small portion (e.g. <1%) of the returned power to a second power detector 144. The circulator ensures that the RP does not damage the generator components. Thus, generator 101 can monitor both incident power and returned power. This monitoring of the incident power and/or returned power may be used to take one or more decisions disclosed herein.

In another embodiment, returned power monitoring mechanism 148 is a separate module (separate from generator 101). For example, an external power meter or a vector network analyzer may be used to measure the returned power. In one such example, a portion of incident and/or returned power passing through the transmission line 102 and/or device 100 is measured.

Figure 4B:
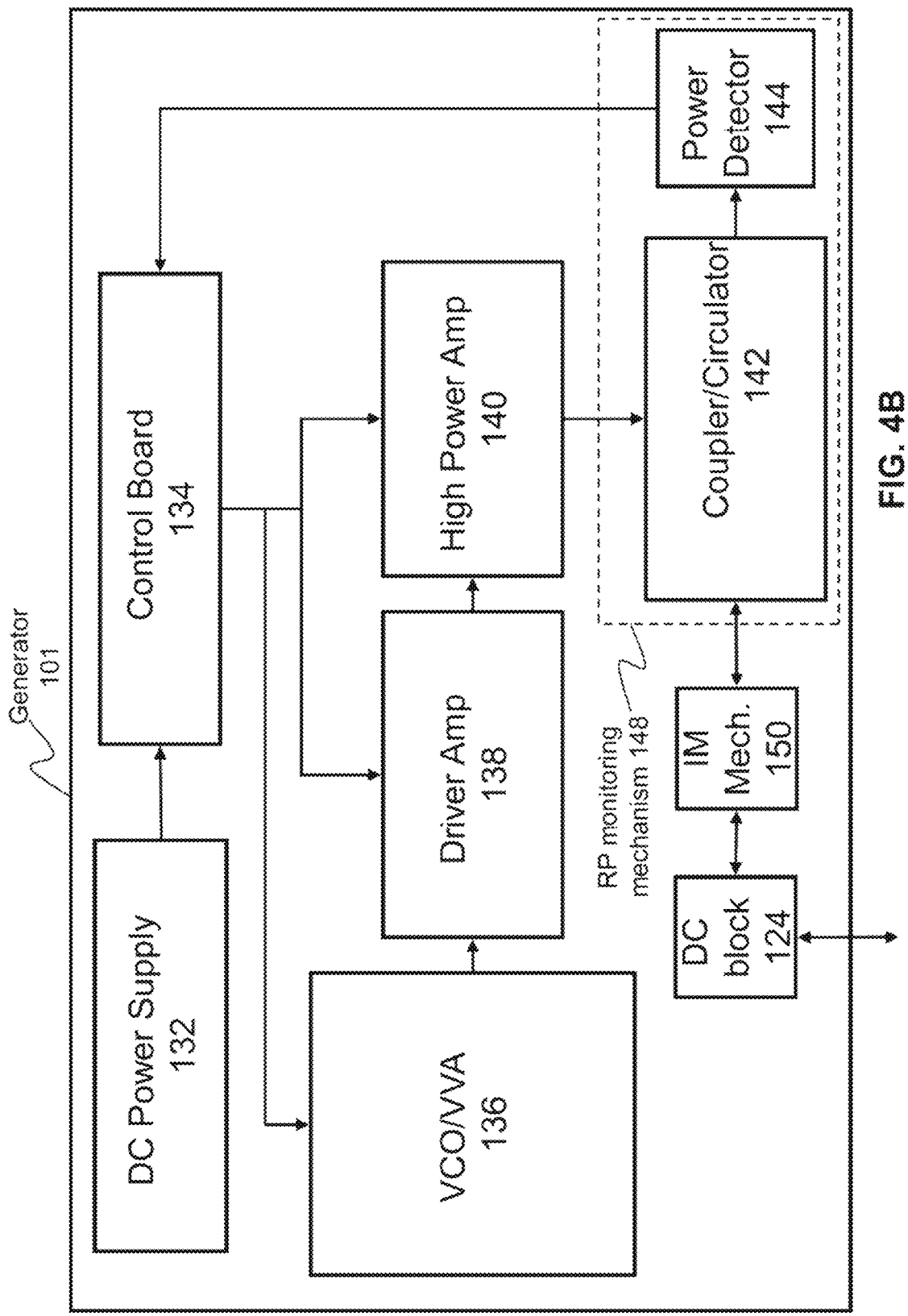
FIG. 4B shows one embodiment of a microwave generator of the present invention comprising an impedance matching mechanism.

FIG. 4B shows one embodiment of a microwave generator 101 of the present invention comprising an impedance matching mechanism. Impedance matching (IM) mechanism 150 may be used to match the source impedance of generator 101 to the load impedance of the load comprising the combination of transmission line 102 and antenna 104 to minimize microwave energy reflection. In one embodiment, IM mechanism 150 is used for complex conjugate matching to maximize power transfer. In one embodiment, IM mechanism 150 is used to exactly cancel the reactive part of the presented load impedance and transform its resistive part to match the one of the system. In one embodiment, IM mechanism 150 comprises a stub positioned a distance from the load. In one embodiment, the length of the stub and/or the distance of stub from the load are varied for tuning the impedance to achieve impedance matching. In another embodiment, IM mechanism 150 comprises a tuner controller that receives a signal indicative of the magnitude of RP from one or both of: RP monitoring mechanism 148 and control board 134. This signal is used to automatically match the source impedance of generator 101 to the load impedance of the load comprising the combination of transmission line 102 and antenna 104.

Figure 5:
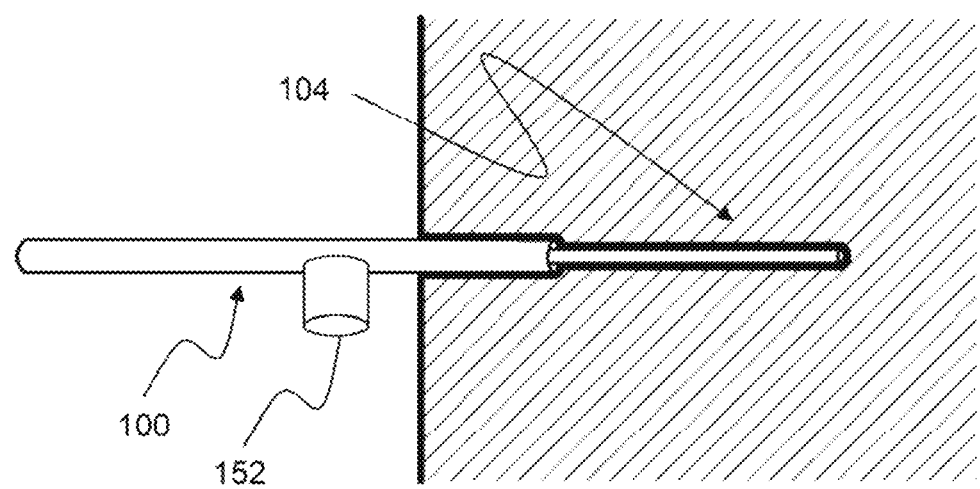
FIG. 5 shows one embodiment of a device of the present invention comprising an impedance matching mechanism.

FIG. 5 shows one embodiment of a device 100 of the present invention comprising an impedance matching mechanism. Impedance matching (IM) mechanism 150 may be used to match the source impedance of generator 101 to the load impedance of the load comprising the combination of transmission line 102 and antenna 104 to minimize microwave energy reflection. In one embodiment, IM mechanism 150 is used for complex conjugate matching to maximize power transfer. In one embodiment, IM mechanism 150 is used to exactly cancel the reactive part of the presented load impedance and transform its resistive part to match the one of the system. In one embodiment, IM mechanism 150 comprises a stub 150 positioned a distance from antenna 104. In the embodiment shown, the stub 150 is in communication with the transmission line of device 100. In one embodiment, the length of the stub 150 and/or the distance of stub from antenna 104 are varied for tuning the impedance to achieve impedance matching. In another embodiment, IM mechanism 150 comprises a tuner controller that receives a signal indicative of the magnitude of RP from one or both of: RP monitoring mechanism 148 and control board 134. This signal is used to automatically match the source impedance of generator 101 to the load impedance of the load comprising the combination of transmission line 102 and antenna 104.

In any of the embodiments herein, including the embodiments shown in FIG. 4B and FIG. 5, IM mechanism 150 may be controlled or adjusted manually by the user based on the RP feedback. In any of the embodiments herein, including the embodiments shown in FIG. 4B and FIG. 5, IM mechanism 150 may be controlled automatically or semi-automatically by control board 134 using the RP feedback.

In any of the embodiments herein, including the embodiments shown in FIG. 4B and FIG. 5, the microwave system may comprise one or more passive or active devices or combinations thereof to perform impedance matching. Examples of such impedance matching devices include, but are not limited to: transformers, resistors, inductors, capacitors, transmission lines, baluns, antenna tuners, matching networks, and terminations. Such one or more one or more passive or active devices may be located at one or more of: within microwave generator 101, between microwave generator 101 and antenna 104 and on antenna 104.

Some embodiments herein illustrate the use of RP measurements for antenna and/or system modification. In one such embodiment, one or more RP measurements may be used to tune antenna 104 and/or the system. This may be done by one or more of: adjusting a tuning stub or other tuning mechanism, adjusting the position and/or configuration of antenna 104, adding or removing an element (e.g. a dielectric) from antenna 104 or other system component, etc.

Figure 6A:
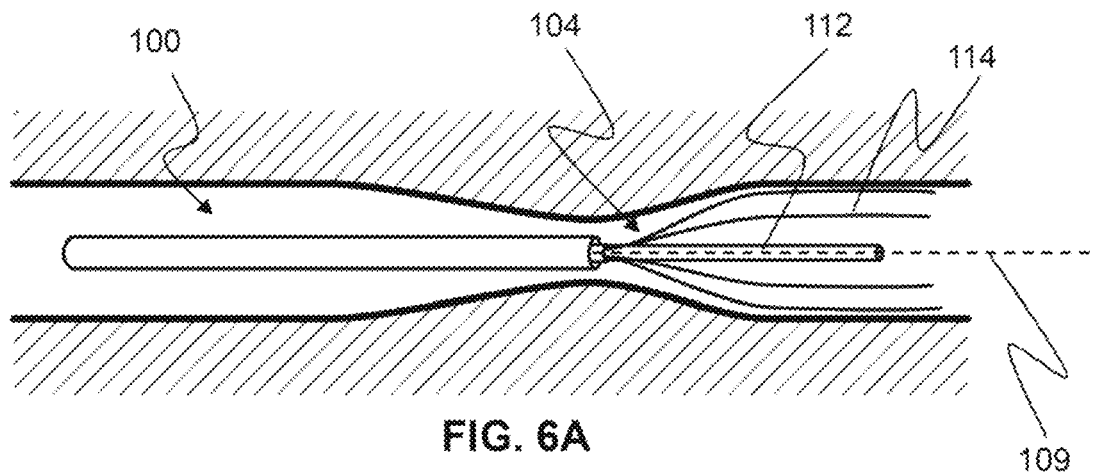
FIGS. 6A-6C show the steps of using an antenna in three different locations of different dimensions within a single target region.
Figure 6B:
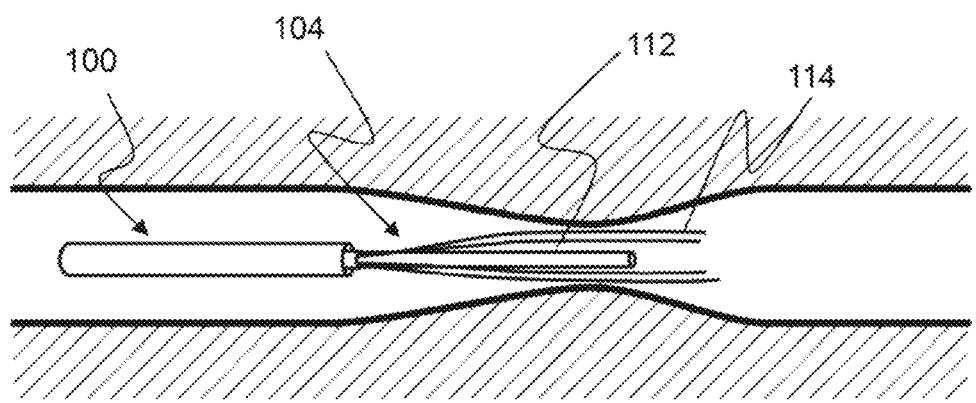
Figure 6C:
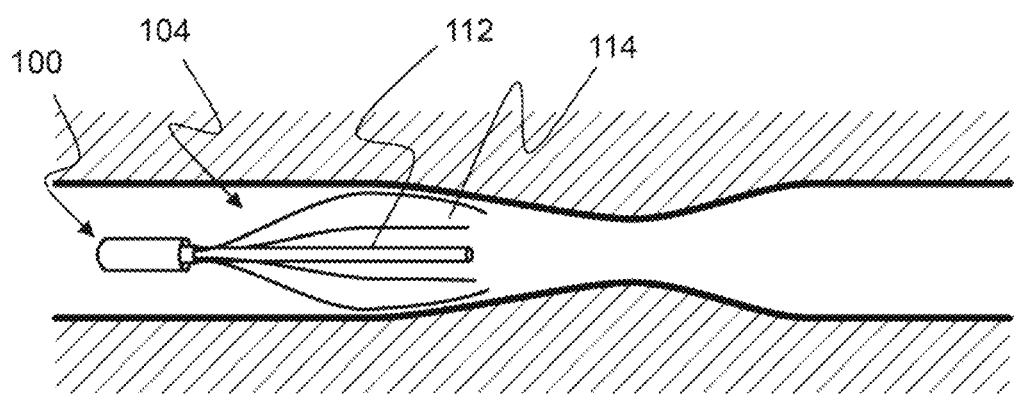

The following embodiments illustrate the use of one or more RP measurements for identification of the surrounding medium and/or automatic adjustment of energy delivery. FIGS. 6A-6C show the steps of using an antenna 104 in three different locations of different dimensions within a single target region. An antenna 104 such as an antenna disclosed in one or more of US 2010/0137857, US 2011/0004205 (incorporated by reference herein) and related patent applications and a hollow target region are used only as examples to illustrate the general device and method embodiment of delivering microwave energy to multiple locations of different dimensions within a single target region. In FIG. 6A, antenna 104 is positioned at a distal location within a target region. This location has a greater dimension. Examples of dimensions include, but are not limited to: length, width, height, thickness, circumference, area, volume, diameter, etc. Antenna 104 in FIG. 6A is deployed such that one dimension (e.g. the outer diameter) of antenna 104 is greater. In FIG. 6B, antenna 104 is deployed within a target region with a smaller anatomical dimension. This leads to a change in the shape of antenna 104 by a change in the shape of one or both of: radiating element 112 and shaping element(s) 114, and antennas dielectrics 116 (if any). The shape change is defined relative to an antenna axis 109 defined as a linear axis parallel to and emerging from the distal end of the transmission line 102. For example, in FIGS. 6A and 6C, shaping elements 114 are in an axially expanded configuration or shape and in FIG. 6B, shaping elements 114 are in an axially compressed configuration or shape. This shape change leads to a change in the position of the shaping elements 114 relative to the radiating element 112 and one or more of: surrounding medium, the distal region of shielding element 106, antenna dielectrics 116 (if any), and floating conductors in the vicinity of radiating member 112 (if any). This in turn leads to a change in the electrical length of antenna 104 due to the change in the interaction of the microwave energy emitted by the radiating element 112 as described earlier. The change in the electrical length of antenna 104 and the corresponding change in the antenna impedance are detected by a change in the returned power (RP). The change in RP may be used to perform a variety of actions as disclosed elsewhere in this specification.

In the embodiments shown in FIGS. 6A-6C, RP may be measured one or more times at each location as disclosed elsewhere in this document. In one such embodiment, a RP limit (e.g. between 15%-75%) is set in the system such that energy delivery is automatically terminated if the RP limit is reached. Microwave energy may be delivered to the three sites by delivering energy to a distal site, moving antenna 104 in a discreet step from the distal site to a proximal site and thereafter delivering energy to the proximal site. In an alternate embodiment, energy may be delivered to the sites by delivering energy continuously while moving antenna 104 continuously from the distal site to the proximal site. In one embodiment of antenna 104, a wider configuration as shown in FIGS. 6A, 6C leads to a lower RP than in the narrower configuration as shown in FIG. 6B. Thus, for a same energy delivery setting, the RP limit is expected to be reached earlier at the site in FIG. 6B than at the site in FIGS. 6A, 6C. Further, for a same energy delivery setting, the power delivered is expected to be lower at the site in FIG. 6B than at the sites in FIGS. 6A, 6C. This will enable an automatic adjustment of energy delivery by delivering a larger energy dose in a wider target region and a smaller energy dose at a narrower target region. This in turn leads to a constant energy dose or power delivery at locations with larger and smaller dimensions. Thus the present invention allows for an automatically adjusted energy delivery in locations of varying dimensions. The change in RP may also be used by a user to determine the shape of a target region e.g. for determining the location of the narrowest or widest region in target region, determining the contour of the target region, etc.

In the embodiment shown in FIGS. 6A-6C, the device can comprise an ablation device 100 with a three dimensional antenna 104 comprising a radiating element and multiple shaping elements adapted to ablate a volume of target material. Antenna 104 comprising a substantially linear or curvilinear radiating element 112. Antenna 104 further comprises a plurality of shaping elements 114. The four shaping elements 114 are identical and are arranged symmetrically around radiating element 112. Embodiments of antenna 104 may be designed with 1-10 shaping elements 114. Shaping elements 114 may be symmetrically or non-symmetrically arranged around radiating element 112. Shaping elements 114 may or may not be identical. Shaping elements 114 may be linear or non-linear. Each shaping element 114 shown is elongate, non-linear and comprises a bend or an angled region. Each shaping element is electrically connected to the outer conductor of coaxial cable 102 or other transmission line such that each shaping element 114 is located substantially distal to the distal end of the transmission line 102 (in zone Z2). The distal end of radiating element 112 and/or shaping elements 114 may comprise a sharp or penetrating tip. In one embodiment, shaping elements 114 are a retractable claw structure that extends from ablation device 100. In one embodiment, the design of radiating element 112 is similar to a 14 mm long monopole antenna. Shaping elements 114 shape and enhance the electromagnetic field in the volume between radiating element 112 and shaping elements 114. This creates a large, volumetric energy delivery zone between radiating element 112 and shaping elements 114 which is substantially confined to the extent of shaping elements 114. Further, shaping elements 114 reduce the leakage current that will otherwise be induced on the outer wall of the outer conductor of coaxial cable 102 or other transmission line. It should be noted that there is no direct electrical conduction between radiating element 112 and shaping elements 114.

When microwave energy is delivered through a transmission line to antenna 104 in FIGS. 6A-6C, a first microwave field is emitted by radiating element 112. The first microwave field interacts with shaping elements 114. This interaction induces a leakage current on shaping elements 114. The leakage current in turn creates a second microwave field. The first microwave field and the second microwave field together combine to produce a unique shaped microwave field of antenna 104 that is clinically more useful that the unshaped microwave field generated by an antenna 104 comprising only radiating element 112. Thus the original microwave field is redistributed by the design of shaping elements 114. Shaping elements 114 alone are not capable of functioning as an antenna; rather shaping elements 114 shape or redistribute the electromagnetic or microwave field emitted by radiating element 112 to produce a shaped microwave field that is clinically more useful. Further, the combination of radiating element 112 and shaping elements 14 improves the power deposition of antenna 104. In absence of shaping elements 114, antenna 104 in FIG. 6A acts like a monopole antenna. Addition of shaping elements 114 generates a shaped microwave field instead of the natural microwave field of a monopole antenna.

In an embodiment of a procedure, antenna 104 is inserted into a material through small punctures. Thereafter, antenna 104 is deployed such that the target material is substantially enclosed or surrounded by the claw-like shaping elements 114. The degree of deployment of antenna 104 may be adjusted to suit different target material sizes. In one such embodiment, one or more pull wires or tethers are attached to shaping elements 114 to control the position of shaping elements 114. In another embodiment, shaping elements 114 are pre-shaped and are made of a material with shape memory properties such as Nitinol. Shaping elements 114 are retracted inside a sheath or a tubular structure in a collapsed configuration before inserting into the target material. Once a portion of the catheter or tubular structure is inserted inside the target material, shaping elements 114 and radiating element 112 are deployed. Shaping elements 114 are deployed to their un-collapsed, preset shape by extending them from the catheter or tubular structure.

In the embodiment of FIGS. 6A-6C, the nearest conductive path to the microwave field emitted by radiating element 112 is provided by the conductive shaping elements 114 instead of the shielding element of the distal region of the transmission line 102. The presence of shaping elements 114 prevents the microwave field from coupling to the distal region of the transmission line 102. Virtually none of the microwave field is located around the distal region of transmission line 102. Further, since a vast majority of the emitted microwave field is deposited in zone Z2, the power deposition of antenna 102 is improved. Virtually no portion of the field is wasted in zone Z1.

In one embodiment of antenna 104 of FIGS. 6A-6C, radiating element 112 comprises an elongate conductor that is about 39+/−10 mm long. The distal end of the elongate conductor may be covered by a metallic tubular cap that is in conductive contact with the elongate conductor. Entire radiating element 112 is covered with a layer of dielectric material such as silicone. Each shaping element 114 comprises a proximal bend and a distal bend. The proximal bend is arranged at a longitudinal distance of about 5 mm from the distal end of the transmission line measured along the length of the radiating element 112. The longitudinal distance between the proximal bend and the distal bend measured along the length of the radiating element 112 is about 29 mm. The longitudinal distance between the distal bend and the distal end of shaping element 114 measured along the length of the radiating element 112 is about 5 mm. Thus the total longitudinal length of each shaping element 114 measured along the length of radiating element 112 is about 39 mm. The maximum diameter of the structure formed by shaping elements 114 is about 30 mm. In this embodiment, shaping elements 114 in antenna 104 improve the matching and also reduce the return loss. Further, shaping elements 114 improve the frequency range over which important performance parameters are acceptable. Thus, a larger frequency range (bandwidth) is available over which antenna 104 delivers an acceptable performance. This in turn allows for a design of antenna 104 wherein minor deformations of antenna 104 during typical use or due to minor manufacturing variations do not significantly affect the performance of antenna 104.

Figure 6D:
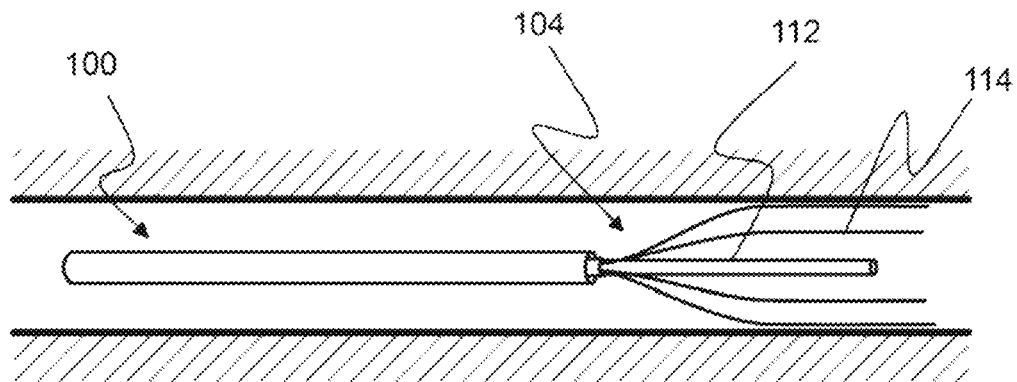
FIGS. 6D-6F show the steps of a method of delivering microwave energy to a target material wherein the properties of the target material change as the microwave energy is delivered.
Figure 6E:
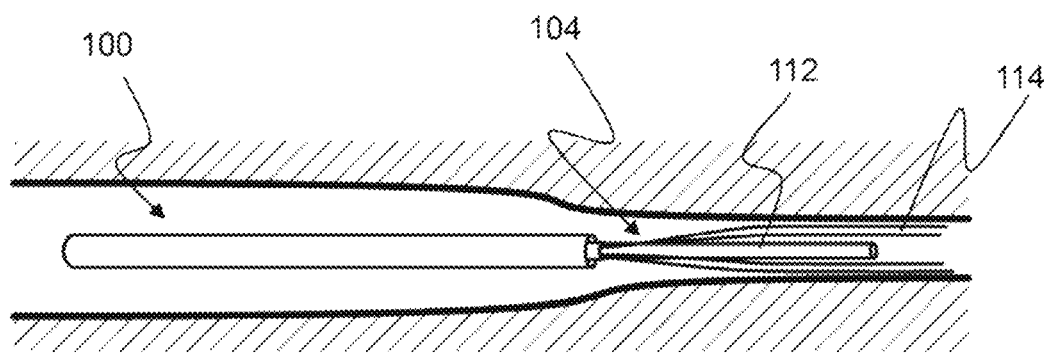
Figure 6F:
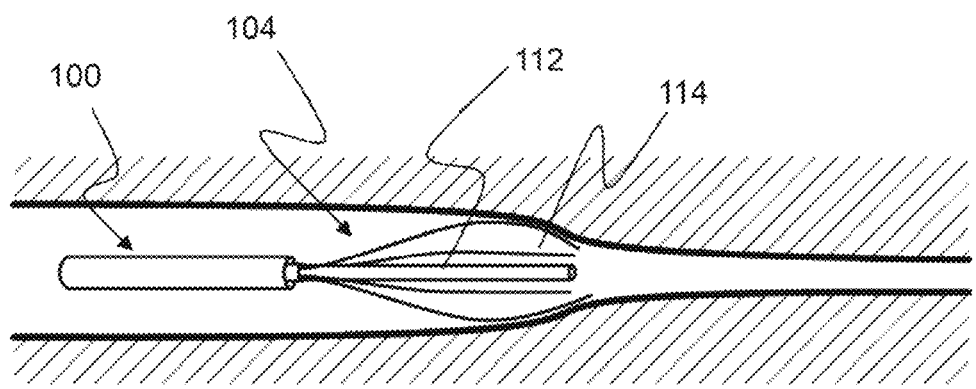

FIGS. 6D-6F show the steps of a method of delivering microwave energy to a target material wherein the properties of the target material change as the microwave energy is delivered. An antenna 104 such as an antenna disclosed in one or more of US 2010/0137857, US 2011/0004205 (both of which are incorporated by reference) and related patent applications and a hollow target are used only as examples to illustrate the general device and method embodiment of delivering microwave energy to a target region wherein the properties of the target region change as the microwave energy is delivered. In FIG. 6D, a microwave antenna 104 is positioned inside a hollow target region and is used to deliver microwave energy to the target material. In FIG. 6E, the delivered microwave energy has led to a change in one or more properties of the target region. Examples of such properties include, but are not limited to: but are not limited to: a physical dimension, area, capacitance, concentration, density, dielectric properties, elasticity, electrical conductivity, impedance, flow rate, fluidity, friability, hardness, inductance, intrinsic impedance, length, location, loss tangent, mass, moisture content, permittivity, plasticity, resistivity, strength, stiffness/flexibility, volume. In the example shown, microwave energy delivery has led to a change in the internal dimension (e.g. the diameter) of the target region. Other examples of microwave energy based changes to tissue include, but are not limited to: changing the water content of an organ or tissue e.g. dehydrating tissue, softening of tissue, changing the dielectric properties of tissue. In FIG. 6E, the change in material properties has led to a change in the shape of antenna 104 which in turn leads to a change in the interaction of the microwave energy emitted by the radiating element 112 relative to one or more of: radiating element 112, surrounding medium, the distal region of shielding element 106, antenna dielectrics 116 (if any), and floating conductors in the vicinity of radiating member 112 (if any). This in turn leads to a change in the electrical length of antenna 104 as described earlier. The change in the electrical length of antenna 104 and the resulting antenna impedance change are detected by a change in the returned power (RP). The change in RP may be used to perform a variety of actions as disclosed elsewhere in this specification. After the step in FIG. 6E, the antenna 104 may be moved to a different location such as shown in FIG. 6F. In another embodiment, the change in the microwave properties of the surrounding material leads to a change in the interaction of the microwave energy emitted by the antenna 104 relative to the surrounding medium. This in turn leads to a change in the electrical length of antenna 104 as described earlier. The change in the electrical length of antenna 104 and the resulting antenna impedance change are detected by a change in the returned power (RP). The change in RP may be used to perform a variety of actions as disclosed elsewhere in this specification.

In the embodiments shown in FIGS. 6D-6F, RP may be measured one or more times at each location as disclosed elsewhere in this document. In one such embodiment, a RP limit (e.g. 25+/−10%) is set in the system that automatically terminates power delivery if the RP limit is reached. Microwave energy may be delivered to the various sites by delivering energy to a first site, moving antenna 104 in a discreet step from the first site to a second site and thereafter delivering energy to the second site. In an alternate embodiment, energy may be delivered to the sites by delivering energy continuously while moving antenna 104 continuously from the first site to the second site. In one embodiment of antenna 104, a wider configuration as shown in FIG. 6D leads to a lower RP than in the narrower configuration as shown in FIG. 6E. This automatically adjusts the energy delivery as the procedure progresses till e.g. the RP limit or a set time limit is reached. Further, this allows a greater energy delivery to large target region and lower energy delivery to smaller target regions. Thus the present invention allows for an automatically adjusted energy delivery in situations wherein the properties of the target region change as the microwave energy is delivered with a consequential increase in efficiency of energy delivery by preventing wastage of energy delivery after the desired microwave effect has been achieved. One or more RP measurements may also be used by a user to determine the shape of a target region e.g. for determining the effect of the energy delivery, determining the contour of the target region, determining the end-point of a procedure, etc.

The target region may be an anatomical region. In one example, the target region is a blood vessel or a duct or another hollow organ. Microwave energy delivery leads to a shrinkage of the organ due to heat induced collagen shrinkage thereby causing a narrowing or occlusion of the blood vessel or duct. In one embodiment, the system comprises a RP limit such that after a sufficient shrinkage has happened, the change in dimensions of antenna 104 lead to an increase in RP until the RP limit is reached. Thereafter, the system automatically stops further energy delivery thereby ensuring the safety of the procedure by preventing excessive energy delivery. This may be used to occlude anatomical regions such as veins (e.g. varicose veins), blood vessels feeding a benign or malignant tumor, etc.

Figure 6G:
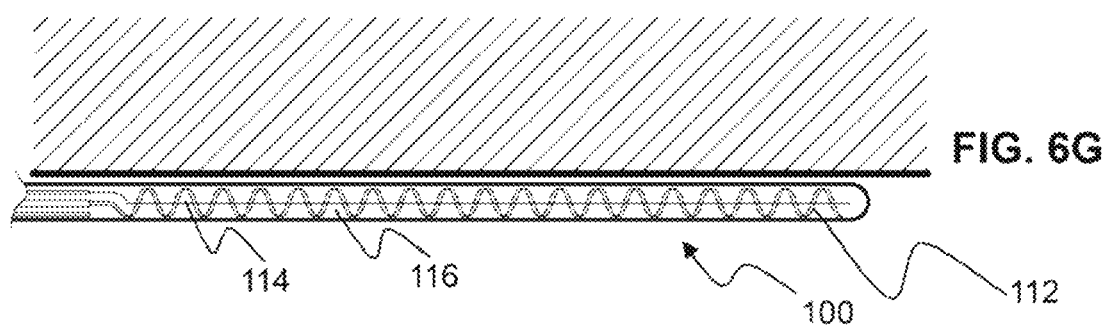
FIGS. 6G-6J show various configurations of a flexible linear microwave antenna deployed in target regions of varying shape.
Figure 6H:
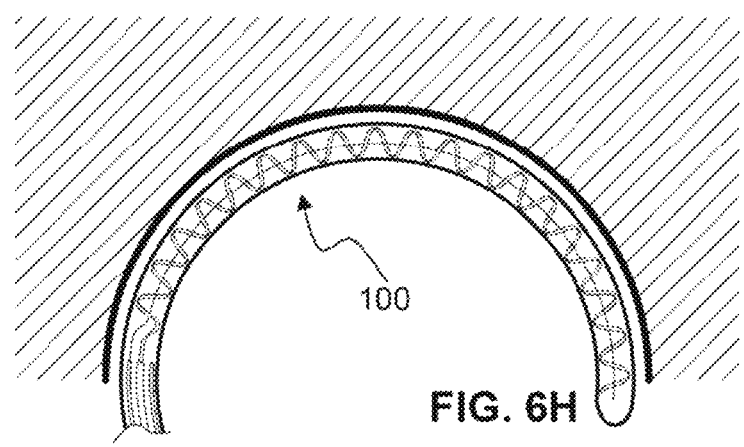
Figure 6I:
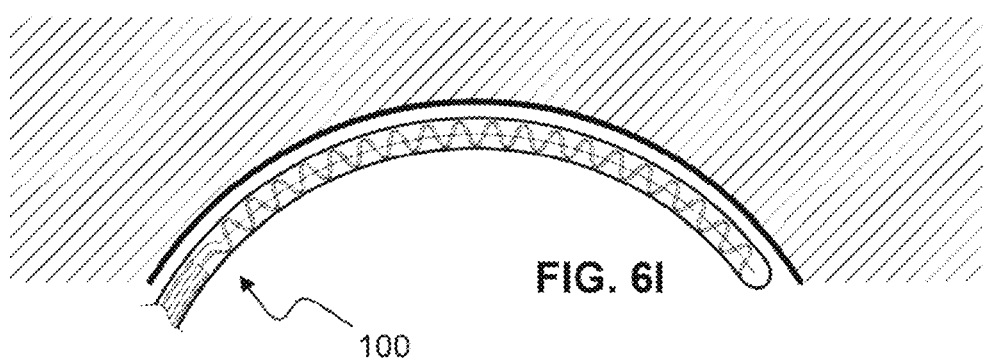
Figure 6J:
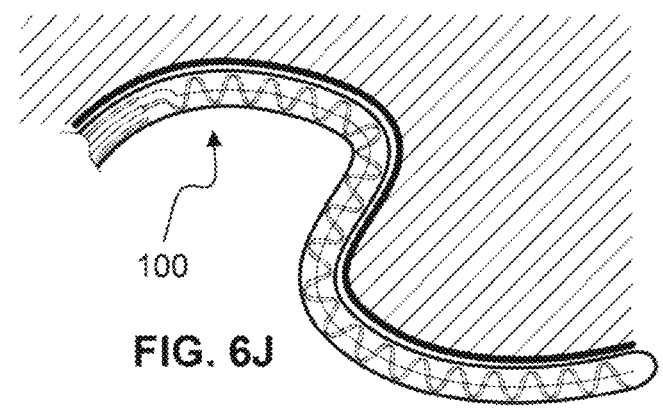

FIGS. 6G-6J show various configurations of a flexible linear microwave antenna deployed in target regions of varying shape. An antenna 104 such as an antenna disclosed in one or more of US 2010/0137857, US 2011/0004205 (incorporated by reference) and related patent applications and a target region surface such as an external or internal surface are used only as examples to illustrate the general device and method embodiment of treating target regions of varying shape. In FIG. 6G, the surface of the target region is flat and thus antenna 104 is in a relatively straight configuration. FIGS. 6H-6I show antenna 104 deployed in locations with a single acute curve, a single less-acute curve and double curves respectively with a consequent change in the antenna 104 configuration. The shape or configuration change of antenna 104 is due to the change in shape of both radiating element 112 and shaping element 114 relative to an antenna axis 109 defined as a linear axis parallel to and emerging from the distal end of the transmission line 102. For example, in FIG. 6G, both radiating element 112 and shaping element 114 are in an axially compressed configuration or and in FIG. 6H, both radiating element 112 and shaping element 114 are in an axially expanded configuration or shape. Due to this shape change, there is a change in the interaction of the microwave energy emitted by the radiating element 112 relative to one or more of: radiating element 112, surrounding medium, the distal region of shielding element 106, antenna dielectrics 116 (if any), and floating conductors in the vicinity of radiating member 112 (if any). This in turn leads to a change in the electrical length of antenna 104 as described earlier. The change in the electrical length of antenna 104 and subsequent change in antenna impedance is detected by a change in the RP. The change in RP may be used to perform a variety of actions as disclosed elsewhere in this specification including, but not limited to: determining the configuration of antenna 104, determining the shape of the target region, determining the contour of a target region, determining the end-point of a procedure, etc.

In the antenna 104 of FIGS. 6G-6J a shaping element 114 is used to improve the performance of a helical antenna. The resultant antenna can be used to create a uniform zone of energy delivery along the length of the antenna 104 without adversely affecting material(s) surrounding the transmission line. In the antenna 104 of FIGS. 6G-6J, an exemplary microwave ablation device 100 comprises a transmission line 102 such as a coaxial cable. An antenna 104 is connected to the distal end of coaxial cable 102. In the embodiment shown, the width of antenna 104 is substantially the same as the width of the coaxial cable 102. Microwave ablation device 100 divided into a first zone Z1 and a second zone Z2 (similar to the embodiment in FIG. 1A) by an imaginary transition line 105. First zone Z1 is proximal to second zone Z2. Transition line 105 is defined by the distal end of coaxial cable 102 and is substantially perpendicular to the axis of coaxial cable 102 at the distal end of coaxial cable 102. The distal region of coaxial cable 102 lies entirely within first zone Z1 and antenna 104 lies entirely within second zone Z2. In one embodiment, a single microwave signal is fed to antenna 104 through coaxial cable 102. When microwave energy is delivered to antenna 104 though coaxial cable 102, antenna 104 generates a microwave field. The near and/or far field of the microwave field generated by antenna 104 may be delivered to the target material. Antenna 104 comprises a radiating element 112 and a shaping element 114. In one embodiment, radiating element 112 is a continuation of the inner conductor 108 of coaxial cable 102. Shaping element 114 shapes the microwave field emitted by radiating element 112. Shaping member 114 is located distal to the distal end of coaxial cable 102 (in zone Z2). In one embodiment, shaping element 114 is made of an electrically conductive material e.g. a metal or a conductive polymer and is electrically connected to a region of outer conductor 106 of coaxial cable 102. In an alternate embodiment, a conductive shaping element 114 is electrically isolated from outer conductor 106. In this embodiment, shaping element 114 functions as a passive radiator or parasitic element of antenna 104. Shaping element 114 in this electrically isolated embodiment absorbs microwaves radiated from radiating element 112 and re-radiates microwaves. Referring back to FIG. 6G, it should be noted that there is no direct electrical conduction between radiating element 112 and shaping element 114. When microwave energy is delivered through coaxial cable 102 to antenna 104, a first microwave field is emitted by radiating element 112. This first microwave field is a normal mode microwave field of a small diameter (antenna diameter D is much less than microwave wavelength) helical antenna. The first microwave field interacts with shaping element 114. This interaction induces a leakage current on shaping element 114. The leakage current in turn creates a second microwave field. The second microwave field is an elongated, axial mode microwave field due to the elongate shape of shaping element 114. The first microwave field and the second microwave field together combine to produce a unique shaped microwave field of antenna 104 that is more useful that the unshaped microwave field generated by an antenna 104 comprising only radiating element 112. Thus the original microwave field is redistributed by the design of shaping element 114.

Further, the specific design of shaping element 114 may be used to improve the power deposition of an antenna 104 comprising radiating element 112. Shaping element 114 may be made of one or more non-insulated or insulated elements. Examples of such elements include, but are not limited to: straight or curved segments of metallic elements, elements with a circular or oval shape, elements with a polygonal shape (e.g. triangular, square, rectangular, pentagonal, etc.), multiple elements joined together by an electrically conducting joint(s), multiple elements joined together by a non-electrically conducting joint(s), elements with multiple curves, symmetrically arranged segments of elements, non-symmetrically arranged segments of elements, elements comprising outer coatings or layers of non-conducting materials, etc.

The embodiment of antenna 104 shown in FIG. 6G has a linear shape that is especially suited for the delivery of microwave energy to a linear region of material.

In the embodiment of FIG. 6G, the surface of radiating element 112 is enclosed within one or more layers of dielectric materials. The thickness and type of dielectric material along the length of radiating element 112 is engineered to optimize the microwave field shape. Thus one or more dielectric materials covering radiating element 112 may also be used as non-conducting shaping elements to shape the microwave field. The one or more dielectric materials covering radiating element 112 shape the microwave field by changing the local dielectric environment in the region adjacent to radiating element 112. In this embodiment, every portion of radiating element 112 is covered with some dielectric material such that no metallic surface of radiating element 112 is exposed to surrounding material. Thus, in this embodiment, radiating element 112 is electrically insulated from material. Thus, in this embodiment, radiating element 112 is able to transmit a microwave field into the surrounding material, but unable to conduct electricity to the surrounding material. Thus, in this embodiment, there is no electrical conduction and no conductive path between radiating element 112 and shaping element 114. Further, in this embodiment, there is no electrical conduction and no conductive path between radiating element 112 and the surrounding material. In one embodiment, the dielectric on a proximal portion of radiating element 112 is a continuation of the dielectric 110 of coaxial cable 102. The thickness of a dielectric on radiating element 112 may vary along the length of radiating element 112. Further, the cross section of a dielectric on radiating element 112 may not be radially symmetric.

In the embodiment of FIG. 6G, radiating element 112 is non-linear and is made of a helically arranged length of a metallic conductor. The helix may be symmetric with a constant pitch and a constant diameter along the length of the helix. In one embodiment, the straightened length of the conductor used for constructing radiating element 112 is about three quarters of the effective wavelength at 915 MHz. In alternate embodiments, this length may be an odd multiple of one quarter of the effective wavelength at one of: 433 MHz ISM band, 915 MHz ISM band, 2.45 GHz ISM band and 5.8 GHz ISM band. Although in FIG. 6G, radiating element 112 has about 19 turns, embodiments of ablation devices 100 may be constructed wherein radiating element 112 has about 1 to 30 turns. The pitch of a helical radiating element 112 may range between 0.3 mm and 20 mm. Radiating element 112 may be made from a metallic element or alloy selected from the group comprising Nitinol, stainless steel or copper.

Any of the radiating elements 112 disclosed herein may comprise a plating of a conducting metal such as Ag or Au on the outer surface of radiating element 112. The metallic conductor used for constructing radiating element 112 may have a round, oval, rectangular or square cross section. In one embodiment, the metallic conductor used for constructing radiating element 112 has a round cross section with a diameter of 0.5 mm+/−0.4 mm. In another embodiment, the metallic conductor used for constructing radiating element 112 has a rectangular cross section with cross sectional dimensions of 10 mm+/−9.5 mm by 0.5 mm+/−0.4 mm. In another embodiment of a radiating element with a rectangular cross section, the cross sectional dimensions are 1 mm+/−0.3 mm by 0.1 mm+/−0.05 mm. In an alternate embodiment, radiating element 112 is made of a length of a metallic conductor that is arranged in a substantially two dimensional configuration. For example, the length of a metallic conductor may be arranged in a substantially wavy or zigzag or serpentine configuration. In the embodiment in FIG. 6G, radiating element 112 is arranged symmetrically around shaping element 114 and partially or fully encloses shaping element 114. Shaping element 114 may be made of a linear or helical length of a metallic conductor. The outer diameter of shaping element 114 may be uniform or may be non-uniform along the length of antenna 104. In the embodiment shown in FIG. 6G, shaping element 114 is made of a substantially linear length of a metallic conductor. Shaping element 114 may be made from a metallic element or alloy selected from the group comprising Nitinol, stainless steel or copper. Shaping element 114 may comprise a plating of a conducting metal such as Ag or Au on the outer surface of shaping element 114. The metallic conductor used for constructing shaping element 114 may have a round, oval, rectangular or square cross section. In one embodiment, the metallic conductor used for constructing shaping element 114 has a round cross section with a diameter of 0.5 mm+/−0.3 mm. In another embodiment, the metallic conductor used for constructing shaping element 114 has a rectangular cross section with dimensions of 0.5 mm+/−0.3 mm by 0.5 mm+/−0.3 mm. Antenna 104 further comprises one or more antenna dielectrics 116 between radiating element 112 and shaping element 114.

In one embodiment, antenna dielectric 116 is sufficiently flexible to create a flexible antenna 104. The flexibility of antenna 104 allows antenna 104 to bend from a substantially straight, linear configuration to a substantially non-linear configuration and vice-versa during use. The flexibility of antenna 104 also allows antenna 104 to bend relative to the distal end of the transmission line during use. This in turn allows a user to introduce antenna 104 to the target location through tortuous or non-linear introduction paths. In one embodiment, antenna dielectric 116 is sufficiently stiff to create a sufficiently stiff antenna 104. The stiffness of antenna 104 prevents antenna 104 from bending during use. This in turn enables the user to use antenna 104 to puncture or penetrate through a target material. Such embodiments of antenna 104 may be used for ablating solid volumes of materials. Examples of dielectrics that can be used between radiating element 112 and shaping element 114 include, but are not limited to EPTFE, PTFE, FEP and other floropolymers. Silicone, Air, PEEK, polyimides, natural or artificial rubbers and combinations thereof. Additionally the entire antenna 104 may be covered or encapsulated in a dielectric. Examples of dielectrics that can be used to cover or encapsulate antenna 104 include, but are not limited to EPTFE, PTFE, FEP and other floropolymers, Silicone, PEEK, polyimides, natural or artificial rubbers and combinations thereof. Antenna dielectric 116 may comprise one or more layers of such dielectrics. The dielectric used to cover or encapsulate antenna 104 may be porous or non-porous. In FIG. 6G, the length of antenna 104 may be between 10 mm and 80 mm and the width of antenna 104 is between 1 mm and 40 mm.

In one particular embodiment, antenna 104 has a length of 45 mm+/−7 mm and a width of 2 mm+/−0.5 mm. Radiating element 112 is electrically connected to inner conductor 108 of coaxial cable 102. This may be done for example, by soldering or resistance welding radiating element 112 to inner conductor 108. Radiating element 112 may be a continuation of inner conductor 108 of coaxial cable 102. Shaping element 114 is electrically connected to outer conductor 106 of coaxial cable 102. This may be done for example, by soldering or resistance welding shaping element 114 to outer conductor 106. Antenna 104 may be floppy, flexible or substantially rigid. Antenna 104 may be malleable or have shape memory or elastic or super-elastic properties.

The distal end of antenna 104 may be soft or atraumatic. Antenna 104 may be designed such that the length of antenna 104 is adjustable. For example, length of antenna 104 may be increased or reduced to increase or reduce the length of an ablation zone. In this embodiment, shaping element 114 may have a helical or substantially wavy or zigzag or serpentine configuration. The length of antenna 104 may be increased or reduced during and/or before a procedure. In one embodiment, the length and/or the diameter of the ablation zone is changed by one or more of: changing the length of radiating element 112, changing the length of shaping element 114, changing the shape of radiating element 112, changing the shape of shaping element 114 and changing the relative positions of radiating element 112 and shaping element 114.

Any of the embodiments of changing the shape or an antenna 104 disclosed herein may lead to a change in the effective length of the antenna 104 which in turns leads to a change in the antenna impedance. This may be detected by measuring RP at one or more times during use. In one embodiment, one or both of radiating element 112 and shaping element 114 are a part of a flexible circuit and are manufactured using commonly known techniques for manufacturing flexible circuits.

In the embodiment of FIG. 6G, the shape of radiating element 112 is different from the shape of shaping element 114. Further in the embodiment in FIG. 6G, radiating element 112 is non-linear. Further in the embodiment in FIG. 6G, shaping element 114 is substantially linear. However radiating element 112 and shaping element 114 are generally oriented such that their axes are parallel to each other. Alternate embodiments of antenna 104 may be designed wherein radiating element 112 is substantially linear. Alternate embodiments of antenna 104 may be designed wherein shaping element 114 is substantially non-linear. Alternate embodiments of antenna 104 may be designed wherein radiating element 112 and shaping element 114 are generally oriented such that their axes are not parallel.

Although in the embodiment in FIG. 6G shaping element 114 is connected to the distal end of coaxial cable 102, other embodiments of antenna 104 may be designed wherein shaping element 114 is connected to coaxial cable 102 at a region other than the distal end of coaxial cable 102. For example, in one alternate embodiment, shaping element 114 is metallic and is electrically connected to a region of outer conductor 106 of coaxial cable 102 proximal to the distal end of the coaxial cable 102.

In FIG. 6G, since radiating element 112 is in electrical contact with inner conductor 108, there is a first electrically conductive path extending from inner conductor 108 till the distal end of radiating element 112. In the embodiments wherein shaping element 114 is made of a conductive material and is electrically connected to outer conductor 106 of coaxial cable 102, there is a second electrically conductive path extending from outer conductor 106 till the distal end of shaping element 114. In such embodiments, even though there are two conductive paths that extend from first zone Z1 to the second zone Z2, the designs, materials and the microwave properties of the two conductive paths may be significantly different in first zone Z and second zone Z2. In first zone Z1, outer conductor 106 of coaxial cable 102 is located symmetrically around inner conductor 108 and at a constant distance from inner conductor 108. However, in second zone Z2, radiating element 112 is located symmetrically around shaping element 114 and at a constant distance from shaping element 114. In first zone Z1, outer conductor 106 of coaxial cable 102 always acts as a shield for the microwave field in first zone Z1 whereas in second zone Z2, shaping element 114 may or may not act as a shield for the microwave field in second zone Z2.

In any of the embodiments herein, radiating element 112 may be a continuation of inner conductor 108 of a coaxial cable 102. In another embodiment, radiating element 112 is length of a conductor attached to inner conductor 108. In one embodiment, the proximal end of radiating element 112 is electrically connected to the distal end of inner conductor 108. In one embodiment, the proximal end of radiating element 112 is soldered to inner conductor 108. In another embodiment, the proximal end of radiating element 112 is laser welded to inner conductor 108. The proximal end of radiating element 112 may be electrically connected to inner conductor 108 in various configurations including, but not limited to lap joint and butt joint. The proximal end of shaping element 114 is electrically connected to a region of outer conductor 106. In one embodiment, the proximal end of shaping element 114 is electrically connected to the distal end of outer conductor 106. In one embodiment, the proximal end of shaping element 114 is soldered to outer conductor 106. In another embodiment, the proximal end of shaping element 114 is laser welded to outer conductor 106. The proximal end of shaping element 114 may be electrically connected to outer conductor 106 in various configurations including, but not limited to lap joint and butt joint.

The SAR profile generated by the device embodiment of FIG. 6G is substantially radially symmetric around antenna 104 and circumferentially and volumetrically envelops entire antenna 104. This entire circumferentially and volumetrically enveloping microwave field around antenna 104 can be delivered to the target material. Further, the microwave field generated by antenna 104 of FIG. 6G is substantially restricted to second zone Z2. There is an insignificant amount of the microwave field in first zone Z1 containing coaxial cable 102. Thus, there is negligible backward coupling between the microwave field and the distal portion of coaxial cable 102. This in turn reduces the risk of ablating material proximal to the distal end of coaxial cable 102. Further, the microwave field is substantially uniform along the length of antenna 104 as compared to a comparable monopole antenna. Embodiments of linear antenna 104 designed to operate at 915 MHz and other microwave frequencies may be designed that can create uniform, symmetrical, continuous, linear or volumetric lesions with a lesion length greater than 35 mm.

In alternate embodiments, the SAR profile may be designed to be substantially non-uniform along the length of a linear antenna 104. For example, an antenna 104 may be designed to have a SAR profile that is wider and/or stronger at the center of antenna 104 and is less strong at the ends of antenna 104. In order to achieve this, one or more design parameters of antenna 104 in FIG. 6G may be modified. Examples of such modifications include, but are not limited to: adding of one or more additional conductive shaping elements 114; varying the width and/or the cross section shape of shaping element 114 and/or radiating element 112 along the length of antenna 104; varying the pitch of helical radiating element 112 and/or helical shaping element 114 along the length of antenna 104; varying the thickness, type and other design parameters of one or more antenna dielectrics 116, etc.

Antenna 104 in FIG. 6G has several advantages over a comparable monopole antenna. In systems comprising a monopole antenna, there is a region of concentrated microwave field or a "hot spot" near the distal end of the transmission line (e.g. a coaxial cable) or at the proximal end of the monopole antenna. About half of the microwave field in such systems is present in first zone Z1. Thus, there is a significant amount of microwave field present in first zone Z1. Thus, there is a high risk of ablating material proximal to the distal end of coaxial cable 102. The presence of a significant amount of microwave field in first zone Z1 is due to undesirable coupling between the microwave field and the outer conductor of the coaxial cable or other transmission line. This undesirable coupling can also cause backward heating of coaxial cable 102 that may lead to collateral damage of material.

In several of the embodiments herein, shaping element 114 plays a critical role in shaping the microwave field generated by antenna 104. In the embodiment of FIG. 6G, the nearest conductive path to the microwave field emitted by radiating element 112 is provided by the conductive shaping element 114 instead of the shielding element of the distal region of the transmission line 102. The presence of shaping element 114 prevents the microwave field from coupling to the distal region of the transmission line 102. Virtually none of the microwave field will be located around the distal region of transmission line 102. Further, since a vast majority of the emitted microwave field is deposited in zone Z2, the power deposition of antenna 102 is improved. Virtually no portion of the field is wasted in zone Z1. Further, the shaping element 114 in antenna 104 of FIG. 6G improves the matching and reduces the return loss.

Any of the shaping elements 114 herein may be used to provide an additional resonance point in the frequency spectrum. This in turn may be used to increase the frequency range (bandwidth) over which antenna 104 delivers an acceptable performance. For example, the design of shaping element 114 in FIG. 6G improves the frequency range over which important performance parameters are acceptable. Thus, a larger frequency range (bandwidth) is available over which antenna 104 delivers an acceptable performance. This in turn allows for a design of antenna 104 wherein minor deformations of antenna 104 during use or due to minor manufacturing variations do not significantly affect the performance of antenna 104, but can be detected using the present invention.

In one particular embodiment of antenna 104 of FIG. 6G, dielectric 116 is transparent and flexible. The linear length of antenna 104 from the distal end of coaxial cable 102 till the distal end of radiating element 112 is about 4.5+/−0.5 cm. Alternate embodiments of antenna 104 may be designed with a linear length ranging from 2.5-5.5 cm. In the particular embodiment, the outer diameter of antenna 104 is about 2 mm. Alternate embodiments of antenna 104 may be designed with an outer diameter ranging from 1.5-4 mm.

In one method embodiment, antenna 104 is used to deliver microwave energy to multiple target regions by repositioning antenna 104. The shape of antenna 104 may or may not be the same at these multiple regions. Antenna 104 may be bent during use without adversely affecting its microwave field shape.

In one method embodiment, a radiating element 112 and a shaping element 114 of an antenna 104 are placed on opposite sides of a target material. Shaping element 114 shapes the microwave field emitted by radiating element 112 such that the microwave field is concentrated in the region between radiating element 112 and shaping element 114. This concentrated microwave field in the region between radiating element 112 and shaping element 114 is used to achieve the desired effect in the material.

In one method embodiment, a target material is located between an antenna 104 and a microwave shield or reflector. Thereafter, microwave energy is delivered to treat the target material.

Any of the embodiments of RP measurement disclosed herein may be used to manually or automatically alter the energy delivery settings during the microwave energy delivery. Examples of such energy delivery settings include, but are not limited to: time limit of the microwave energy delivery, the average power, and the pulse width, height or frequency if the microwave energy is delivered in discrete pulses (i.e. altering the duty cycle).

The following embodiments illustrate the use of RP measurements for the automatic or manual termination of energy delivery. Such method embodiments can use any of the antennas 104 disclosed herein and in one or more of US 2010/0137857, US 2011/0004205, US 2010/0121319 (incorporated by reference herein) and related patent applications.

As microwave energy is delivered to a target material, one or more properties of the target material such as moisture content, temperature, impedance, a physical dimension, permittivity, dielectric constant, loss tangent, resistivity, hardness, and friability, and other properties disclosed herein progressively change. This changes the microwave interaction of antenna 104 with the surrounding medium which in turn changes the effective length of antenna 104 as described earlier. Thus the impedance matching of an antenna with the target tissue will progressively change as the microwave energy delivery progresses leading to progressively varying RP. This degree of RP variation will be dependent on the degree of microwave-induced change of the target material. Thus the present invention can be used to determine the degree of change in the target material due to the effect of the microwave energy. Further, the present invention may also be automatically shut off the energy delivery after creating a desired microwave-induced change (e.g. by a set RP limit) or convey to the user the changed RP indicating the creation of the desired material change.

In one such embodiment of microwave ablation antennas, as microwave energy is delivered to a target tissue, the tissue gets ablated and properties of tissue such as moisture content and other properties disclosed herein progressively change. This changes the microwave interaction of antenna 104 with the surrounding medium which in turn changes the effective length of antenna 104 as described earlier. Thus the matching of an antenna with the target tissue will progressively change as the ablation progresses leading to progressively varying RP. This degree of RP variation will be dependent on the degree of ablation of the tissue. Thus the present invention can be used to determine the degree of ablation. Further, the present invention may also be automatically shut off the energy delivery after creating a desired ablation (e.g. by a set RP limit of 25+/−10%) or to indicate to the user the changed RP indicating the creation of the desired ablation.

In one such embodiment of endometrial ablation, as the ablation progresses, the RP progressively increases. The ablation is allowed to progress till the RP reaches as set RP limit (e.g. a set RP limit of 25+/−10%) or a time limit after which the system automatically terminates energy delivery. This allows the full thickness of the endometrium to be ablated while preventing excessive delivery of microwave energy which might compromise procedure safety.

Figure 6K:
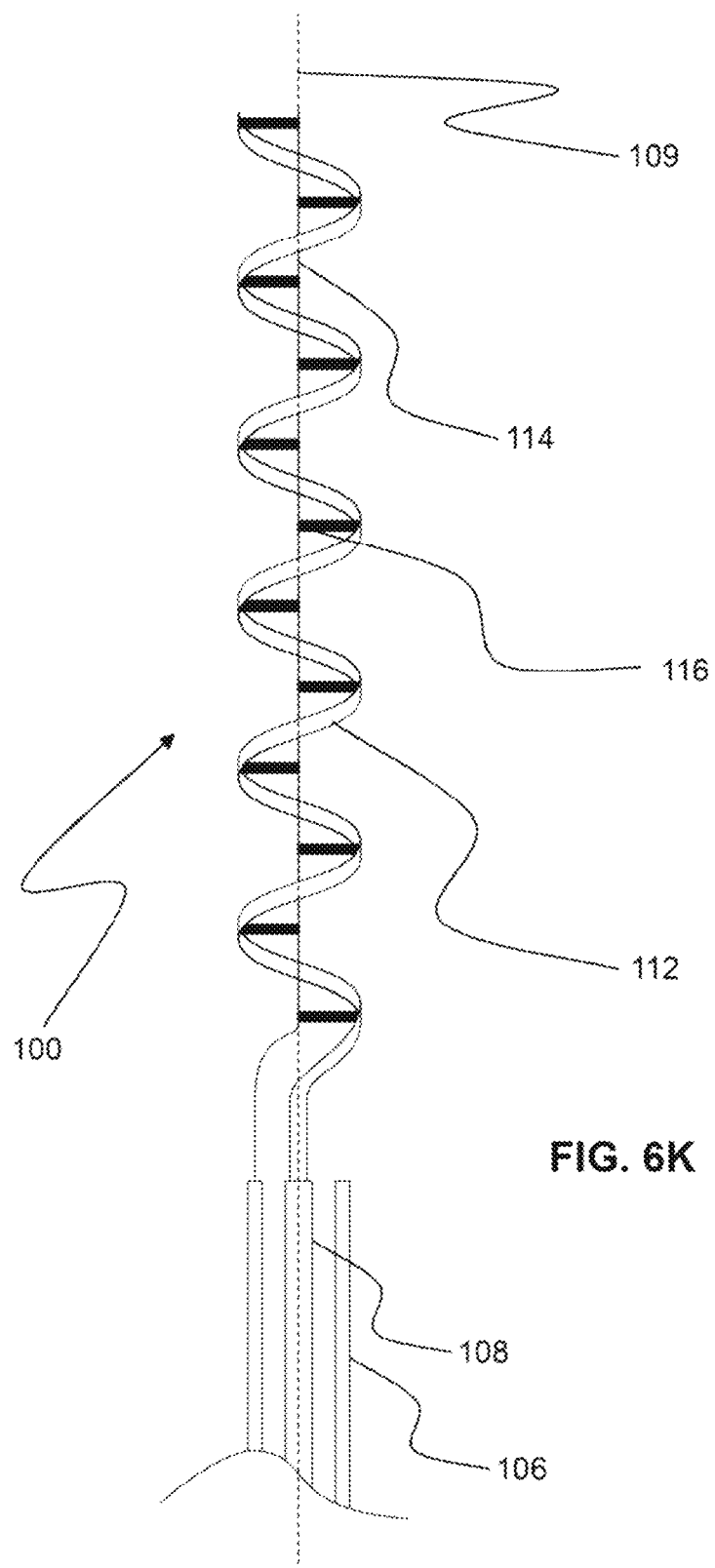
FIG. 6K shows an embodiment of an antenna similar to the antenna in FIGS. 6G-6J comprising a radiating element and a shaping element connected to each other by one or more flexible dielectric attachments.

FIG. 6K shows an embodiment of an antenna similar to the antenna in FIGS. 6G-6J comprising a radiating element and a shaping element connected to each other by one or more flexible dielectric attachments. The attachments 116 shown in FIG. 6K are made of a dielectric material and thus called antenna dielectrics 116 in this specification. Antenna dielectric 116 allows a greater relative motion between radiating element 112 and shaping element 114 than in the antenna 104 in FIG. 6G wherein both radiating element 112 and shaping element 114 are embedded in an antenna dielectric 116. Antenna dielectrics 116 may be made of one or more of the following: elements with a spring action; flexible elastic elements; flexible non-elastic elements; straight or curved segments of dielectric materials; etc. ANY OTHERS?. In one embodiment, radiating element 112 is flexible and antenna 104 self-expands in diameter in a mechanically unconstrained environment. In a mechanically constrained environment, antenna 104 self-expands to the maximum extent possible. The antenna impedance in the constrained configuration and the non-constrained configuration are different.

Figure 6L:
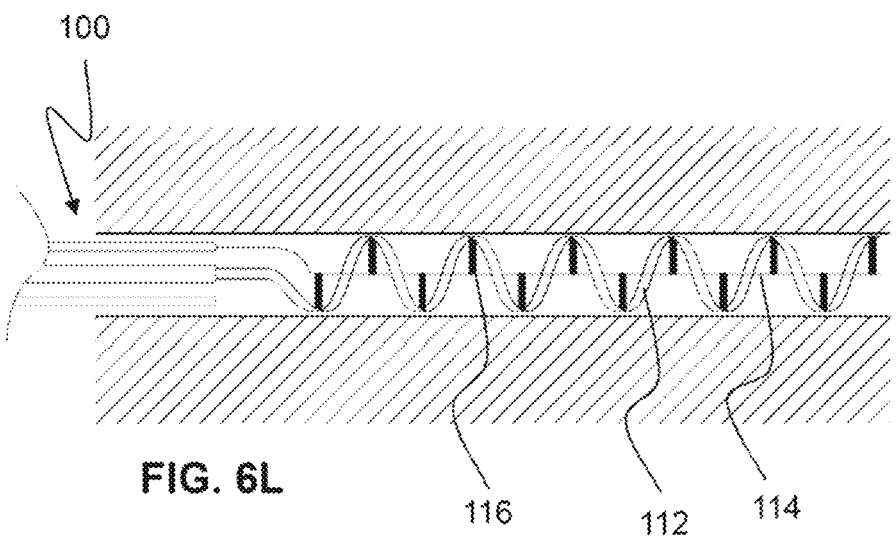
FIGS. 6L, 6M and 6N show three configurations of the antenna of FIG. 6K in a constrained configuration, a less constrained configuration and a least constrained configuration respectively.
Figure 6M:
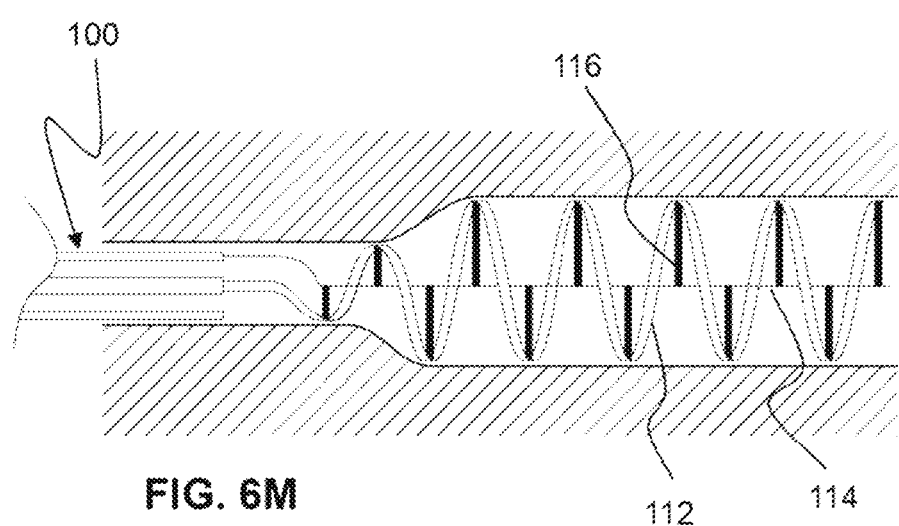
Figure 6N:
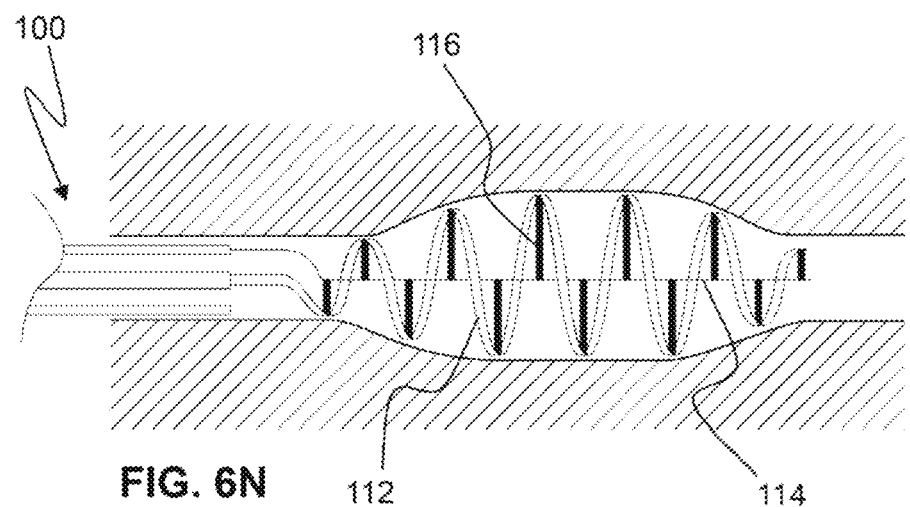

FIGS. 6L, 6M and 6N show three configurations of antenna 104 of FIG. 6K in a constrained configuration, a less constrained configuration and a least constrained configuration respectively. The configuration change is defined as a change in the shape of one or both of: radiating element 112 and shaping element 114 relative to an antenna axis 109 defined as a linear axis parallel to and emerging from the distal end of the transmission line 102. For example, in FIGS. 6M and 6N, shaping element 114 is in an axially expanded configuration or shape and in FIG. 6L, shaping element 114 is in an axially compressed configuration or shape. In FIG. 6L, antenna 104 is deployed in a target region of a smaller dimension. The target region is of a sufficient stiffness so that it does not get deformed when antenna 104 is deployed in the target region. This causes antenna 104 to be deployed in a more constrained configuration in the target region of a smaller dimension in FIG. 6L as compared to the target region of a greater dimension in FIG. 6M. The antenna configurations in constrained and un-constrained configurations may be different due to one or more of: change in the shape of radiating element 112, change in the shape of shaping element 112, change in the position and/or shape of antenna dielectrics 116, and change in the length of antenna 104. Specifically, in the embodiments shown in FIGS. 6L and 6M, the shape of radiating element 112 has been changed along with the shape and/or the position of antenna dielectrics 116. This leads to a change in the position of radiating element 112 relative to shaping element 114, surrounding medium, the distal region of shielding element 106, antennas dielectrics 116 (if any), and floating conductors (if any) in the vicinity of radiating member 112. This in turn leads to a change in the electrical length of antenna 104 due to the change in the interaction of the microwave energy emitted by the radiating element 112 with shaping element 114. The change in the electrical length of antenna 104 and the corresponding change in the antenna impedance are detected by a change in the returned power (RP). The change in RP may be used to perform a variety of actions as disclosed elsewhere in this specification.

The target region in FIG. 6N has the same dimension as that in FIG. 6L. However, in this embodiment, the target region is of a sufficient flexibility so that it gets deformed when antenna 104 is deployed in the target region. This causes the antenna 104 to be deployed in a less constrained configuration in FIG. 6N as compared to the embodiment in FIG. 6L. Comparing FIGS. 6L and 6N, the shape of radiating element 112 has been changed along with the shape and/or the position of antenna dielectrics 116. This leads to a change in the position of radiating element 112 relative to shaping element 114, surrounding medium, the distal region of shielding element 106, antennas dielectrics 116 (if any), and floating conductors (if any) in the vicinity of radiating member 112. This in turn leads to a change in the electrical length of antenna 104 due to the change in the interaction of the microwave energy emitted by the radiating element 112 with shaping element 114. The change in the electrical length of antenna 104 and the corresponding change in the antenna impedance are detected by a change in the returned power (RP). The change in RP may be used to perform a variety of actions as disclosed elsewhere in this specification. In one embodiment, the RP of a system comprising an antenna 104 of FIG. 6K increases as the degree of constraint of antenna 104 increases. The embodiments in FIGS. 6L-6N demonstrate that the RP value may be a function of both the mechanical and microwave properties of the target material. Any of the embodiments herein may use RP feedback to determining the mechanical and/or microwave properties of the target material.

Figure 6O:
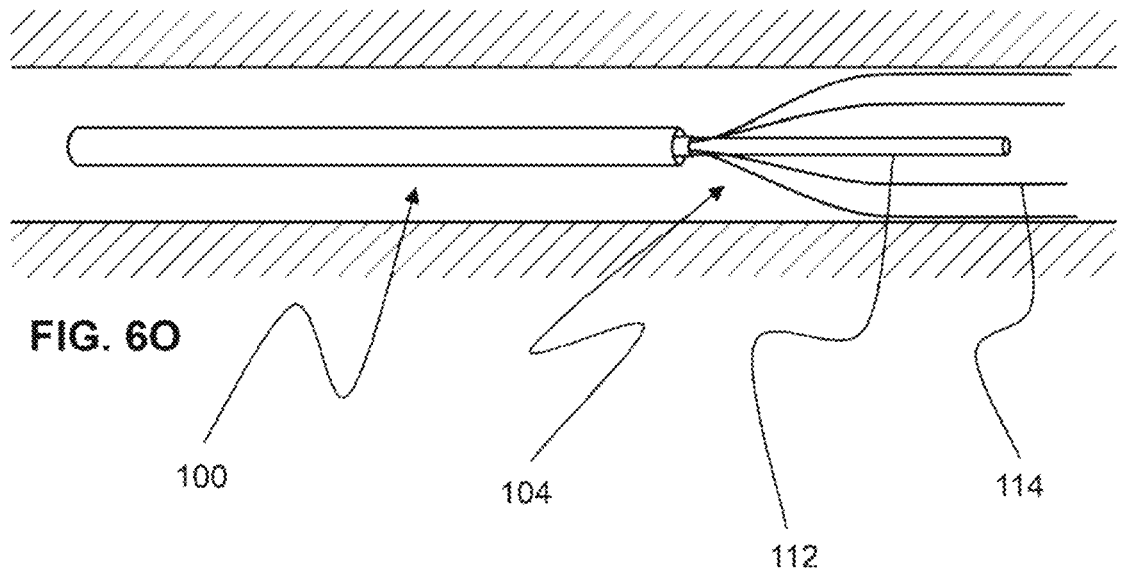
FIGS. 6O and 6P show an antenna similar to that in FIG. 6A in a constrained configuration and a less constrained configuration respectively.
Figure 6P:
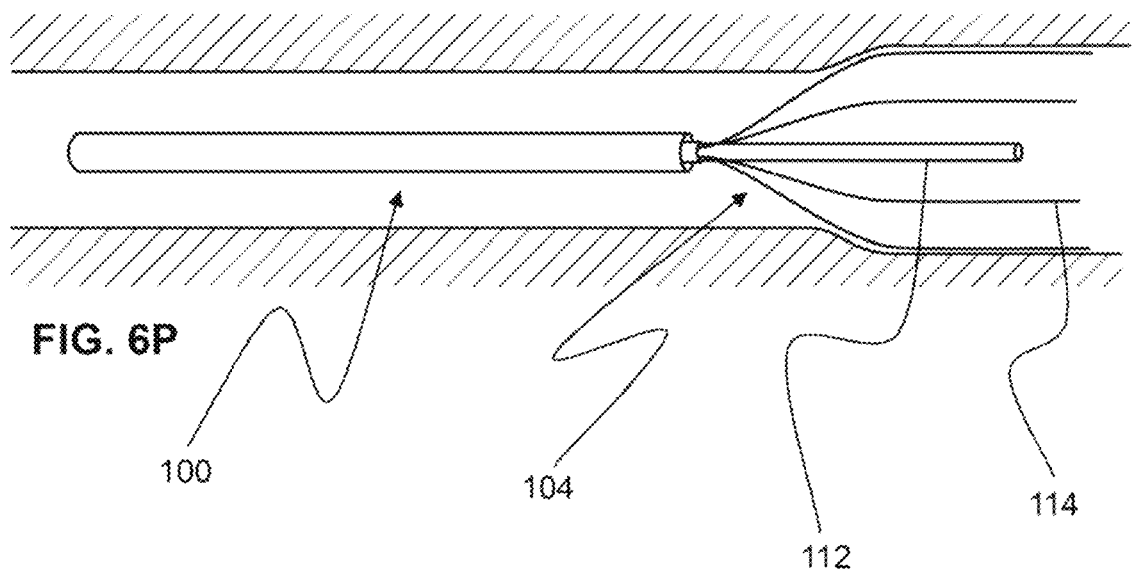

FIGS. 6O and 6P show an antenna 104 similar to that in FIG. 6A in a constrained configuration and a less constrained configuration respectively. The dimensions of the target regions in FIGS. 6O and 6P and their microwave properties are the same. However, the target region in FIG. 6O is of a sufficient stiffness so that it does not get deformed when antenna 104 is deployed and the target region in FIG. 6P has a sufficient flexibility so that it gets deformed when antenna 104 is deployed. This causes antenna 104 to be deployed in a more constrained configuration in FIG. 6O as compared to the configuration in FIG. 6P. The antenna configurations in constrained and un-constrained configurations may be different due to one or more of: change in the shape of radiating element 112, change in the shape of shaping element 112, change in the position and/or shape of antenna dielectrics 116, and change in the length of antenna 104. Specifically, in the embodiments shown in FIGS. 6O and 6P, the shapes of shaping elements 114 have been changed along with the shape and/or the position of antenna dielectrics 116 (if any). This leads to a change in the position of the shaping elements 114 relative to the radiating element 112, surrounding medium, the distal region of shielding element 106, antennas dielectrics 116 (if any), and floating conductors (if any) in the vicinity of radiating member 112. This in turn leads to a change in the electrical length of antenna 104 due to the change in the interaction of the microwave energy emitted by the radiating element 112 with shaping element 114. The change in the electrical length of antenna 104 and the corresponding change in the antenna impedance are detected by a change in the returned power (RP). The change in RP may be used to perform a variety of actions as disclosed elsewhere in this specification. The embodiments in FIGS. 6O-6P further demonstrate that the RP value may be a function of both the mechanical and microwave properties of the target material.

Figure 6Q:
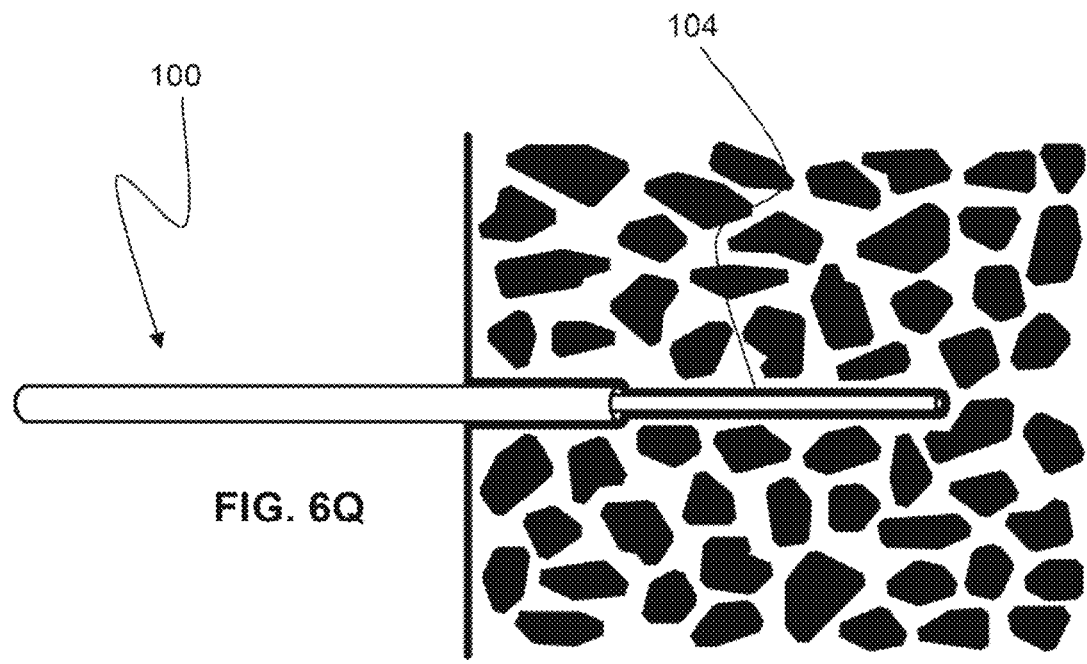
FIGS. 6Q and 6R show an embodiment of a method of determining one or more properties of a target material using a device of the present invention.
Figure 6R:
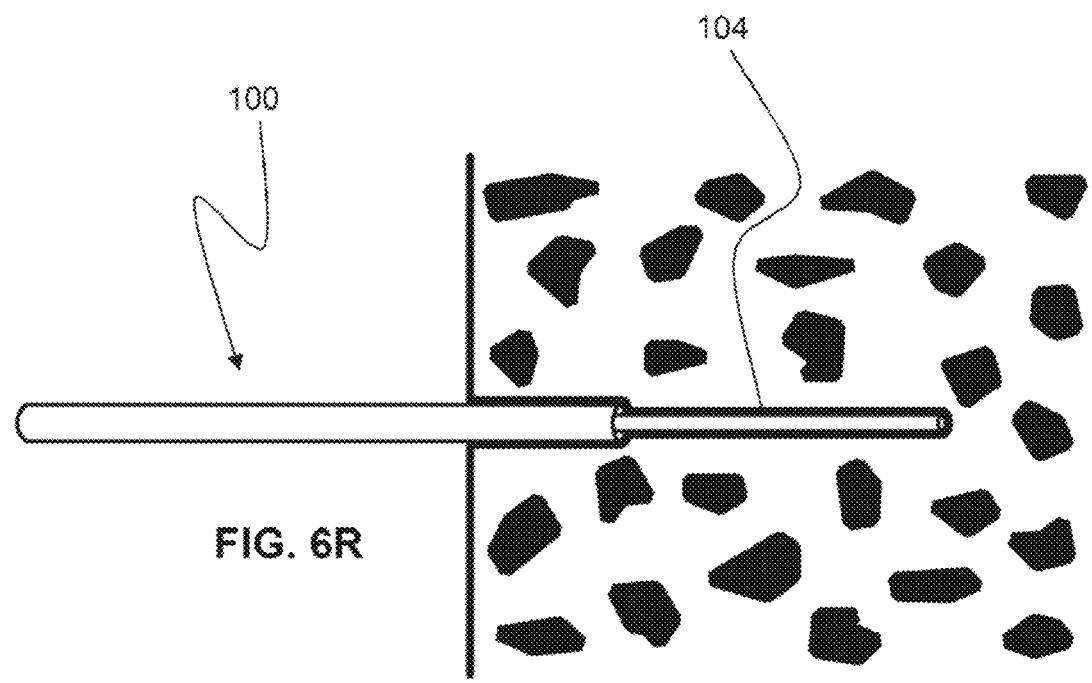

FIGS. 6Q and 6R show an embodiment of a method of determining one or more properties of a target material using a device of the present invention. In FIGS. 6Q and 6R, the same antenna 104 is inserted into or otherwise brought into proximity of two target materials that differ in at least one material property. Antenna 104 may be one of the antennas disclosed herein or an antenna comprising a method or device embodiment of the present invention. One or more RP readings are made as disclosed elsewhere in this specification. The difference in the one or more RP readings (e.g. difference between the RP readings in two materials, difference in the RP reading between a test/target material and reference RP reading(s), etc.) is used to determine the properties of the target material(s). Examples of target materials include, but are not limited to: a mineral or an industrial raw material, an ore or portions of a mine, a metal or metallic substance, a dielectric material, a food product or ingredient, a fluid, wood, cement or other building material, a semiconductor material, a biological material including human tissue, a plastic or polymer material, or any other material disclosed herein. Example of target material properties include, but are not limited to: a physical dimension, area, capacitance, concentration, density, dielectric properties, elasticity, electrical conductivity, impedance, flow rate, fluidity, friability, hardness, inductance, intrinsic impedance, length, location, loss tangent, mass, moisture content, permittivity, plasticity, resistivity, strength, stiffness/flexibility, volume.

FIGS. 6S and 6T show antenna 104 deployed in two target regions of different dimensions. In FIGS. 6S and 6T, planar antennas 104, the uterine cavity and the uterus are used only as examples to illustrate the general device and method embodiment. In FIG. 6S, antenna 104 is deployed in a uterus with a uterine cavity that is wider than the uterine cavity in FIG. 6T. Thus, antenna 104 in FIG. 6S is deployed with a wide width than the antenna in FIG. 6T. Thus, there is a greater distance between radiating element 112 and shaping element 114 in the configuration in FIG. 6S than in the configuration in FIG. 6T. This in turn leads to a change in the electrical length of antenna 104 due to the change in the interaction of the microwave energy emitted by the radiating element 112 with shaping element 114. The change in the electrical length of antenna 104 and the corresponding change in the antenna impedance are detected by a change in the returned power (RP). In one embodiment, a laterally or axially compressed configuration of this antenna 104 (e.g. in FIG. 6T) wherein radiating element(s) and shaping elements(s) are very close to each other in an antenna disclosed in one or more of US 2010/0137857, US 2011/0004205, US 2010/0121319 (incorporated by reference herein) and related patent applications has a higher RP than a laterally uncompressed configuration (e.g. in FIG. 6S). Thus by measuring the RP during one or more times and/or during one or more positions in the uterine cavity, one or more of the following may be determined: the deployed antenna shape, anatomical dimensions, outlines of the uterine cavity, presence of uterine pathology such as fibroids or polyps or congenital deformations, thin-wall uteri, presence of foreign bodies (e.g. IUD) in uterine cavity, and presence of air pockets. Further, if a RP limit is set in the generator (e.g. a RP limit of 25+/−10%), the system will stop energy delivery earlier in FIG. 6T than in FIG. 6S since the starting RP will be higher in FIG. 6T than in FIG. 6S. Further, for a same energy delivery setting, the power delivered to the tissue is expected to be lower in FIG. 6T than in FIG. 6S due to the difference in RP. This will enable an automatic adjustment of energy delivery by delivering a larger energy dose for a larger target region and a smaller energy dose for a smaller target region. The change in RP may be also used to perform a variety of actions as disclosed elsewhere in this specification. In another embodiment, an antenna 104 comprising a flexible radiating member 112 and lacking a shaping member 114 may be used similarly. In another embodiment, an antenna 104 comprising a relatively inflexible radiating member 112 and a flexible shaping member 114 may be used similarly. The shape change in FIGS. 6S and 6T can also be defined in terms of the change in the shape of the radiating element 112 and shaping element 114 relative to an antenna axis 109 defined as a linear axis parallel to and emerging from the distal end of the transmission line 102. For example, in FIG. 6S, radiating element 112 and shaping element 114 are in an axially expanded configuration or shape and in FIG. 6T, radiating element 112 and shaping element 114 are in an axially compressed configuration or shape.

The invention also includes several embodiments of planar antennas 104 e.g. as shown in FIGS. 6S and 6T. Such planar antennas 104 may be used to deliver energy to planar or non-planar regions. Such planar antennas 104 may comprise single or multiple splines, curves or loops in a generally planar arrangement. Planar antennas 104 may be used for ablating a material surface. In FIGS. 6S and 6T, microwave ablation device 100 comprises a transmission line (such as a coaxial cable 102) terminating in an antenna 104 at the distal end of the transmission line. In one embodiment, a single microwave signal is fed to antenna 104 through coaxial cable 102. When microwave energy is delivered to antenna 104 though coaxial cable 102, antenna 104 generates a microwave field. The near field of the microwave field generated by antenna 104 may be used for endometrial ablation and other methods. In FIGS. 6S and 6T, antenna 104 comprises a radiating element in the form of an outer loop 112 and a shaping element in the form of a metallic center loop 114. Outer loop 112 and center loop 114 may touch each other when deployed in the anatomy. In one embodiment, outer loop 112 is a continuation of the inner conductor of coaxial cable 102. Center loop 114 shapes or redistributes the microwave field radiated by outer loop 112. It should be noted that there is no direct electrical conduction between outer loop 112 and center loop 114. When microwave energy is delivered through coaxial cable 102 to antenna 104, a first microwave field is emitted by outer loop 112. The first microwave field interacts with center loop 114. This interaction induces a leakage current on center loop 114. The leakage current in turn creates a second microwave field. The first microwave field and the second microwave field together combine to produce a unique shaped microwave field of antenna 104. Thus the original microwave field is redistributed by the design of center loop 114. Center loop 114 alone is not capable of functioning as an antenna; rather center loop 114 shapes or redistributes the electromagnetic or microwave field emitted by outer loop 112 to produce a shaped microwave field. Further, the combination of outer loop 112 and center loop 114 improves the power deposition of antenna 104.

In one embodiment, outer loop 112 has no sharp corners. Sharp corners in outer loop 112 may cause the field to concentrate in the vicinity of the sharp corners. In one embodiment, the minimal radius of curvature of a corner in outer loop 112 is at least 0.5 mm. In the embodiment in FIG. 6S, the radius of curvature of corner regions in outer loop 112 is at least 1 mm.

In one embodiment, antenna 104 has a shape that substantially approximates the shape of the target material. For example, antenna in FIGS. 6S and 6T has a roughly triangular shape that approximates the shape of the uterine cavity and is especially suited for endometrial ablation. The proximal portion of the antenna 104 is directed towards the cervix and corner regions 154 of outer loop 112 are directed towards the fallopian tubes. However, as mentioned before, microwave thermal ablation does not necessarily require perfect contact with the target material. Thus antenna 104 is able to ablate all or substantially all of the endometrium. The entire endometrium can be ablated in a single ablation by antenna 104 having a single microwave antenna. Thus, repositioning of antenna 104 after an ablation may not be needed.

Further, antenna 104 in the working configuration is generally flat and flexible. The plane of outer loop 112 is substantially parallel to the plane of center loop 114. The flat and flexible antenna 104 in FIGS. 6S and 6T in its deployed configuration has an atraumatic distal end in which the distal region of antenna 104 is wider than the proximal portion of antenna 104. The flexible nature of antenna enables antenna 104 to take the natural shape of the introduction passage instead of distorting the passage or getting hindered due to the passage.

In one embodiment of a deployed configuration of antenna 104 as shown in FIGS. 6S and 6T, the length of outer loop 112 measured along the outer loop 112 from the distal end of coaxial cable 102 until the distal end of outer loop 112 is about three quarters of the effective wavelength at the 915 MHz ISM band. The effective wavelength is dependent on the medium surrounding the antenna and the design of an antenna dielectric on the outer loop 112. The design of the antenna dielectric includes features such as the type of dielectric(s) and thickness of the dielectric layer(s). The exact length of the outer loop 112 may be determined after tuning the length of outer loop 112 to get good impedance matching. The length of the outer loop 112 in one embodiment is 100+/−15 mm. In one embodiment, the width of deployed outer loop 112 is 40+/−15 mm and the longitudinal length of deployed outer loop 112 measured along the axis of coaxial cable 102 till the distal most region of outer loop 112 is 35+/−10 mm.

In the embodiment shown in FIGS. 6S and 6T, an antenna dielectric 116 in the form of a roughly Y-shaped, relatively stiff, antenna dielectric piece 116 comprising two distal end regions is located roughly at the center of antenna 104. Dielectric piece 116 provides sites for mechanical attachment of various regions of antenna 104 and helps antenna 104 to be deployed from and retracted into an introducing sheath 122. A first distal end region is roughly oriented towards the central axis of antenna 104 and has sites for attachment of distal regions of outer loop 112 and center loop 114 as shown. In one embodiment, the first distal end region has two openings through which distal regions of outer loop 112 and center loop 114 pass. In another embodiment, first distal end region is attached to outer loop 112 and center loop 114 by one or more of: glues or adhesives, mechanical fastening structures, heat shrinkable elements, etc. Distal end of outer loop 112 is mechanically connected to a second distal end region as shown. The mechanical connection may be made by one or more of: glues or adhesives, mechanical fastening structures, heat shrinkable elements, etc. Dielectric piece 116 may be constructed from a material selected from the group consisting of: PEEK, PEBAX, ABS and other relatively stiff polymer materials. An additional function of the dielectric piece 116 is to provide the user with force feedback about the proper position of the device inside a uterus or other target material.

In one embodiment of a clinical procedure, antenna 104 is inserted in a collapsed, undeployed configuration through introducing sheath 122 into the uterine cavity. Thereafter, antenna 104 is pushed distally relative to introducing sheath 122 to deploy antenna 104 out of the distal end of introducing sheath 122. This causes antenna 104 to attain the deployed configuration as shown in FIGS. 6S and 6T. Thereafter, antenna 104 is pushed distally such that the distal most region of antenna 104 (first distal end region 162 of dielectric piece 116) pushes against the fundus. The sufficiently stiff dielectric piece 116 causes the user to feel a resistance as soon as the distal most region of antenna 104 pushes against the fundus. This in turn provides the user with a force feedback about the position of antenna 104 against the fundus.

In one embodiment, the proximal portion of outer loop 112 is designed to be stiffer and have greater mechanical strength than the distal portion. This may be achieved by leaving original dielectric material 110 of coaxial cable 102 on the proximal portion of outer loop 112. In an alternate embodiment, this is achieved by coating the proximal portion of outer loop 112 by a layer of antenna dielectric.

In the embodiment shown in FIGS. 6S and 6T, the cross sectional shape of outer loop 112 is not uniform along the entire length of outer loop 112. In this embodiment, the proximal portion of outer loop 112 is a continuation of the inner conductor of coaxial cable 102. This portion has a substantially circular cross section. A middle portion of outer loop 112 has a substantially flattened or oval or rectangular cross section. The middle portion may be oriented generally perpendicular to the distal region of coaxial cable 102 in the deployed configuration as shown in FIGS. 6S and 6T. The middle portion of outer loop 112 is mechanically designed to bend in a plane after deployment in the anatomy. This in turn ensures that the distal most region of ablation device 100 is atraumatic and flexible enough to conform to the target material anatomy. This helps in the proper deployment of outer loop 112 in the uterus. In one embodiment, the middle portion of outer loop 112 is a continuation of inner conductor of coaxial cable 102 and is flattened.

In one embodiment, the distal most portion of outer loop 112 is a continuation of inner conductor of coaxial cable 102 and is non-flattened such that it has a circular cross section. In one embodiment, outer loop 112 is made of a length of a Nitinol or stainless steel wire. A distal portion of the wire is deformed (e.g. by flattening) or has material removed (e.g. by grinding, laser machining, EDM, etc.). Thereafter, the wire is plated with a layer of highly conductive materials such as Au or Ag. This wire is used to replace the inner conductor 108 of coaxial cable 102. This assembly is then used to construct microwave device 100. In another embodiment, outer loop 112 is made of a length of a Nitinol or stainless steel wire clad with a layer of highly conductive materials such as Au or Ag. A distal portion of the wire is deformed (e.g. by flattening). This wire is used to replace the inner conductor 108 of coaxial cable 102. This assembly is then used to construct microwave device 100.

One or more outer surfaces of outer loop 112 may be covered with one or more layers of antenna dielectrics 116. One or more outer surfaces of center loop 114 may be covered with one or more layers of antenna dielectrics 116. The thickness and type of antenna dielectric material along the length of outer loop 112 are engineered to optimize the microwave field shape. In one embodiment shown in FIGS. 6S and 6T, every portion of outer loop 112 is covered with some antenna dielectric material such that no metallic surface of outer loop 112 is exposed to material. Thus, in the embodiment of FIGS. 6S and 6T, outer loop 112 is able to transmit a microwave field into material, but unable to conduct electricity to material. Thus, in the embodiment of FIGS. 6S and 6T, there is no electrical conduction and no conductive path between outer loop 112 and center loop 114 even though outer loop 112 and center loop 114 may physically touch each other when deployed in the target material. Examples of dielectric materials that can be used as antenna dielectrics in one or more embodiments disclosed herein include, but are not limited to EPTFE, PTFE, FEP and other floropolymers, Silicone, Air, PEEK, polyimides, cyanoacrylates, polyolefins, epoxy, natural or artificial rubbers and combinations thereof. The antenna dielectric 116 on the proximal portion of outer loop 112 may be a continuation of the dielectric 110 of coaxial cable 102. There may be an additional layer of a stiffer antenna dielectric 116 over this layer of antenna dielectric 116.

In FIGS. 6S and 6T, the shape of outer loop 112 is different from the shape of center loop 114. Further, in FIGS. 6S and 6T, outer loop 112 and center loop 114 are substantially planar and the plane of outer loop 112 is substantially parallel to the plane of center loop 114. Further, in FIGS. 6S and 6T, both outer loop 112 and center loop 114 are non-linear.

In the embodiments wherein the transmission line is a coaxial cable, two proximal ends of center loop 114 are in electrical contact with two regions on the outer conductor 106. In one embodiment, the two proximal ends of center loop 114 are electrically connected to diametrically opposite regions on or near the distal end of outer conductor 106 such that center loop 114 is located distal to the distal end of the transmission line 102 (in zone Z2). A transmission line jacket may be located over a part of or the entire portion of the transmission line e.g. a coaxial cable that connects to antenna 104. The distal end of transmission line jacket may be located near the two proximal ends of center loop 114. Transmission line jacket may be made of sufficiently stiff materials including, but not limited to: PEEK, PEBAX, FEP, floropolymers, polyurethanes, etc. that increase the stiffness of the transmission line. This in turn allows the user to obtain force feedback during the procedure as described earlier. Also, the stiff transmission line jacket facilitates the pushing or pulling or turning of the device during a procedure by a user.

In a method embodiment, when ablation device 100 is used for endometrial ablation, antenna 104 of FIGS. 6S and 6T generates a microwave field that is more concentrated in the center of the uterus and is less concentrated towards the cornual regions and towards the cervix. Thus, the depth of ablation generated by antenna 104 is deeper in the center of the uterus and is less deep towards the cornual regions and towards the cervix. Such a profile is clinically desired for improved safety and efficacy. In one embodiment, the ablation profile is shaped to ablate a majority of the basalis layer of the uterine endometrium. In one embodiment, center loop 114 is made of a round or flat wire. In one embodiment, center loop 114 is made of a wire of round cross section with two flattened ends and a central flattened portion. In one such embodiment, center loop 114 is made of an Ag or Au clad Nitinol or stainless steel wire with a circular cross sectional profile and a diameter of 0.01"+/−0.005". Such loop shaped shaping elements 114 do not act as a shield for the microwave field i.e. there is no sharp drop in the microwave field intensity past center loop 114. In the embodiment of FIGS. 6S and 6T, center loop 114 is roughly oval in shape. In the embodiment of FIGS. 6S and 6T, the width of center loop 114 is 20+/−10 mm and the longitudinal length of deployed center loop 114 measured along the axis of coaxial cable 102 from line 105 till the distal most region of center loop 114 is 33+/−10 mm. When ablation device 100 is used for endometrial ablation, outer loop 112 and center loop 114 both contact the endometrial material surface.

Center loop 114 may be mechanically independent from outer loop 112 or may be mechanically attached to outer loop 112. In the embodiment shown in FIG. 4A, center loop 114 and outer loop 112 are both mechanically connected to dielectric piece 116.

Parts of center loop 114 may or may not be covered by one or more layers of antenna dielectric materials 116. In the embodiment of FIGS. 6S and 6T, one or more or all metallic surfaces of center loop 114 are exposed to the device environment. Portions of outer loop 112 and center loop 114 may be made from one or more of lengths of metals such as copper, Nitinol, aluminum, silver or any other conductive metals or alloys. One or more portions of outer loop 112 and center loop 114 may also be made from a metallized fabric or plastics.

The SAR profile generated by an antenna similar to the antenna of FIGS. 6S and 6T is shaped such that the field intensity towards the center of antenna 104 is higher than the field intensity towards the corners of antenna 104. This in turn means that the ablation at the center of antenna 104 will be deeper than the ablation at the corners of antenna 104. Also, the microwave field is shaped such that it is wider distally and narrower proximally. The microwave field volumetrically envelops entire antenna 104 and is substantially bilaterally symmetric. The shaped microwave field is more uniformly distributed over a wider area of the antenna 104 than the microwave field of an antenna lacking center loop 114. Further, an insignificant portion of the shaped microwave field extends proximally to the distal end of coaxial cable 102.

In the embodiment of FIGS. 6S and 6T, the nearest conductive path to the microwave field emitted by radiating element 112 (outer loop 112) is provided by the conductive shaping element 114 instead of the shielding element of the distal region of the transmission line 102. The presence of shaping element 114 prevents the microwave field from coupling to the distal region of the transmission line 102. Virtually none of the microwave field is located around the distal region of transmission line 102. Further, since a vast majority of the emitted microwave field is deposited in zone Z2, the power deposition of antenna 102 is improved. Virtually no portion of the field is wasted in zone Z1. In absence of center loop 114, the microwave field interacts with an element of transmission line 102 such as the outer conductor of a coaxial cable. This results in a non-desirable profile of the microwave field e.g. a concentrated field around the distal region of the transmission line 102. This interaction can also cause backward heating of coaxial cable 102 that may lead to collateral damage of material.

The presence of center loop 114 also improves the matching, reduces the return loss and increases the power efficiency. In the presence of center loop 114, microwave power is delivered more efficiently to the material and not wasted as heat generated within ablation device 100. Shaping element 114 also increases the frequency range (bandwidth) over which antenna 104 delivers an acceptable performance. Thus, a larger frequency range (bandwidth) is available over which antenna 104 delivers an acceptable performance. This in turn allows for a design of antenna 104 wherein minor deformations of antenna 104 during typical clinical use or due to minor manufacturing variations do not significantly affect the performance of antenna 104.

Several alternate planar antennas 104 may be designed that comprise anywhere between 1-4 planar radiating elements 112 and 1-6 planar shaping elements 114. The shape of the one or more planar radiating elements 112 and planar shaping elements 114 may be selected from the group consisting of: full or partial loop, linear segments, heart shaped segments, spirals, curved segments, zig-zag segments, etc.

Any of the microwave antennas 104 disclosed herein may be designed such that a portion of the antenna 104 is deployable by engaging a mechanical deployment system. The mechanical deployment system may be used to change antenna 104 from an insertion configuration to a working configuration capable of carrying out its intended purpose. One example of such a mechanical deployment system is a system of one or more pullable and releasable pull wires.

Figure 6U:
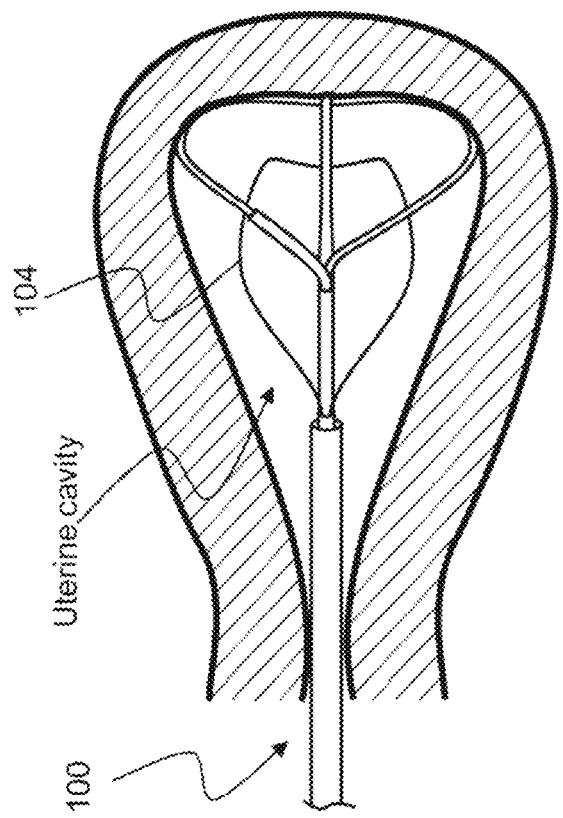
FIGS. 6U and 6V show two steps of a method of ablating the uterine endometrial lining.
Figure 6V:
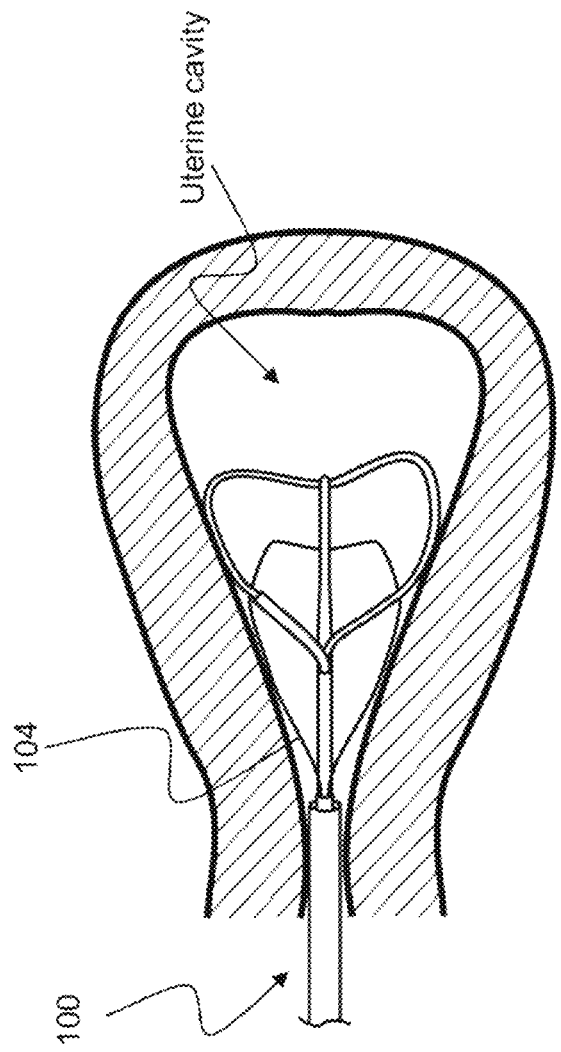

FIGS. 6U and 6V show two steps of a method of ablating the uterine endometrial lining using an antenna such as an antenna disclosed in one or more of US 2010/0137857, US 2011/0004205, US 2010/0121319 (incorporated by reference) and related patent applications. Just as in FIGS. 6S and 6T the uterine cavity and the uterus are used only as examples to illustrate the general device and method embodiment of treating a target region longer than the antenna 104 wherein the dimensions of the target region vary along its length. In the embodiment shown in FIGS. 6U and 6V, RP may be measured one or more times as disclosed elsewhere in this document.

In one such embodiment, a RP limit (e.g. 25+/−10%) is set in the system that automatically terminates power delivery if the RP limit is reached. In FIGS. 6U and 6V, the uterine cavity is treated at at least two sites: a distal, fundal site as shown in FIG. 6U and a proximal site as shown in FIG. 6V. This is especially useful to treat longer uterine cavities. The at least two sites may be treated by treating the distal site, moving antenna 104 in a discreet step from the distal site to the proximal site and thereafter treating the proximal site.

In an alternate embodiment, the at least two sites may be treated by delivering energy continuously while moving antenna 104 in a continuously from the distal site to the proximal site. Antenna 104 has a wider configuration at the distal site and thus the RP is expected to be lower at the distal site. Further, the lesions created at the distal site and the proximal site may partially overlap. Since the tissue within the lesion has lowered water content due to desiccation, the RP is expected to be higher at the proximal site. Thus, for a same energy delivery setting, the RP limit is expected to be reached earlier at the proximal site than at the distal site. Further, for the same set power, the power delivered to the tissue is expected to be lower at the proximal site than at the distal site due to the difference in RP. This will enable an automatic adjustment of energy delivery by delivering a larger energy dose at the distal site and a smaller energy dose at the proximal site. This translates to greater energy delivery and hence deeper ablation at the distal site than at the proximal site. This is important for both safety and efficacy of an endometrial ablation procedure since the endometrium and the myometrium are thicker at the distal, fundal region than at the proximal, lower uterine region. Thus the present invention allows for an automatically adjusted energy delivery in the uterine cavity with a greater safety and efficacy than a similar system lacking the automatically adjusted energy delivery of the present invention.

In one embodiment, the time limit setting for treating the proximal site is lower than that for treating the distal site. In one such embodiment, the time limit set for treating the proximal site is between 15%-80% of the time limit set for treating the distal site.

Further, as the antenna 104 is moved into the cervical canal, antenna 104 is expected to be mis-deployed as shown later in FIG. 7F which in turn translates to a significantly higher RP. Thus the system may not be able to deliver energy at all or deliver only an insignificant amount of energy before automatically shutting off if antenna 104 is inadvertently positioned in the cervical canal. This automatically ensures the safety of the endometrial ablation procedure even if the antenna is positioned in the cervical canal. This embodiment may also be used by a user to test for the location of internal cervical os or a narrow region in a target material by determining the position of the antenna 104 at the point at which the RP rises significantly or the RP limit is reached. This in turn can be used to estimate the uterine cavity length from the fundus to the internal os. Thus antenna 104 using the present invention may also be used to determine the anatomy of an organ. In another embodiment, an antenna 104 comprising a flexible radiating member 112 and lacking a shaping member 114 may be used similarly. In another embodiment, an antenna 104 comprising a relatively inflexible radiating member 112 and a flexible shaping member 114 may be used similarly.

The following embodiments illustrate the use of returned power measurements for determining antenna positioning and deployment.

Figure 7A:
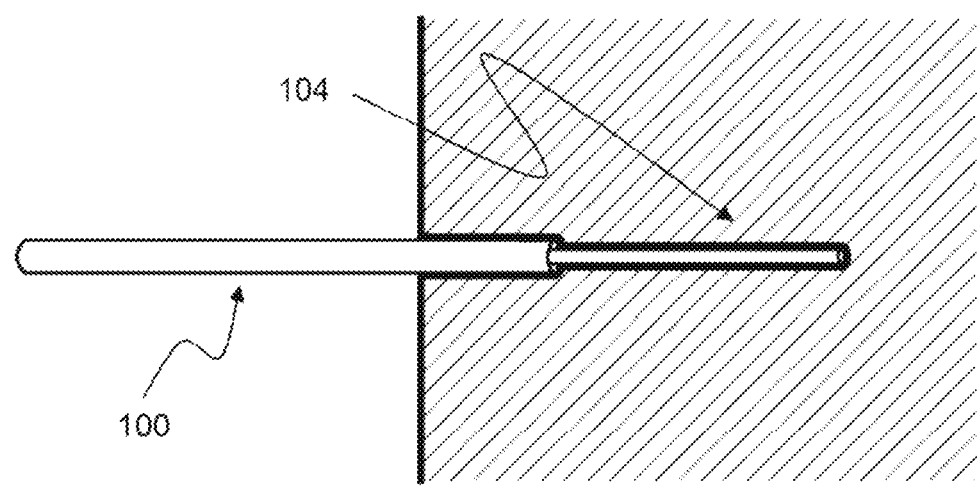
FIGS. 7A and 7B show two steps of a method of confirming the position of an antenna inside a target material.
Figure 7B:
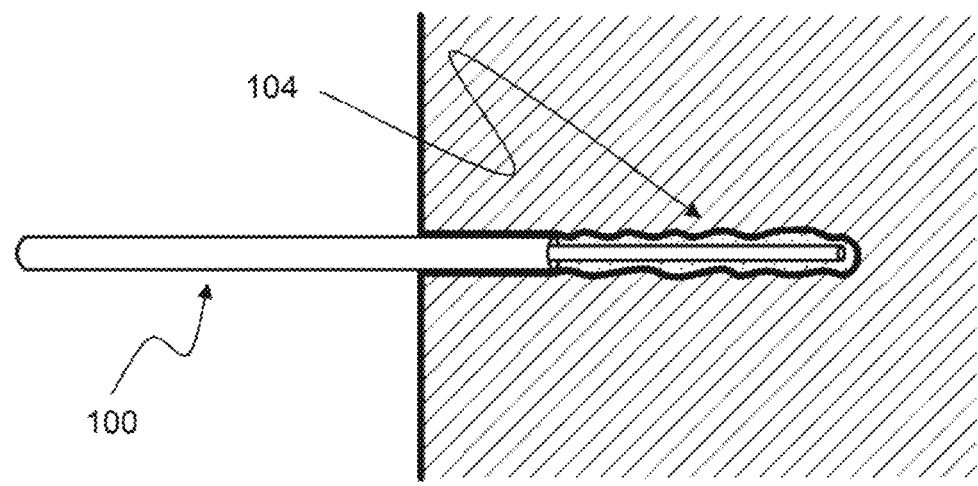

FIGS. 7A and 7B show two steps of a method of confirming the position of antenna 104 inside a target material. This may be used e.g. to confirm the position of antenna 104 inside a cavity in the target material. In medical applications, the cavity can be a bodily cavity or passage (e.g. uterine cavity, a blood vessel, etc.). The method may also be used to detect a perforation or leakage of the cavity or region. The cavity may be a natural or artificially created cavity or passage. The method may also be used e.g. to confirm the position of antenna 104 inside a solid material. In FIG. 7A, antenna 104 is inserted into a region of the target material. In FIG. 7B, a fluid is injected or otherwise introduced into the target material surrounding antenna 104. The injected fluid changes the microwave properties of the medium surrounding antenna 104. This in turn leads to a change in the microwave interaction of the radiating element 112 and shaping element 114 (if any) relative to the surrounding medium. This in turn leads to a change in the electrical length of antenna 104 due to the change in the interaction of the microwave energy emitted by the radiating element 112. The change in the electrical length of antenna 104 and the corresponding change in antenna impedance is detected by a change in the returned power (RP). The change in RP between steps shown in FIGS. 7A and 7B can be used to determine or confirm the position of antenna 104 inside a desired target material or region and/or used to perform a variety of actions as disclosed elsewhere in this specification. In one embodiment, a fluid that improves the matching of antenna 104 with surrounding material is injected into the target material. This will lead to a reduction in the RP if the fluid is retained in the surrounding material. This will give an indication that antenna 104 is within solid material or within a cavity that is intact. In another embodiment, a fluid (e.g. a gas like carbon dioxide, a dielectric, etc.) that worsens the matching of antenna 104 with surrounding material is injected into the target material. This will lead to an increase in the RP if the fluid is retained in the surrounding material. This will give an indication that antenna 104 is within a solid material or within a cavity that is intact. A loss of the fluid (e.g. due to antenna 104 located in a leaky or non-intact cavity or within a large cavity e.g. a large blood vessel) will not cause a significant change in the RP thereby allowing the user to determine the position of antenna 104 and/or obtain feedback about the property of material surrounding antenna 104.

In another method embodiment, an additional step of removing the injected fluid (e.g. by suction) is performed. One or more RP readings during one or more of: before fluid is injected, after injection of fluid, and after removal of fluid may be taken and used to determine or confirm the position of antenna 104 inside a target material and/or used to perform a variety of actions as disclosed elsewhere in this specification. If antenna 104 is inserted into a cavity, one or more natural or artificially created openings into the cavity and/or the insertion track of device 100 may be permanently or temporarily sealed during one or more of: before fluid is injected, after injection of fluid, and after removal of fluid. Perforation or leakage of the cavity or region can also be detected by measuring the change or lack or change in the RP readings between steps shown in FIGS. 7A and 7B. In one such embodiment, a fluid is injected into the medium surrounding antenna 104 and the pressure of the fluid is maintained. The variation of RP with time is used to determine perforation or leakage of the cavity or region. Absence or partial or complete presence of antenna 104 in the target material cavity or region can also be detected by measuring the change or lack or change in the RP readings between steps shown in FIGS. 7A and 7B.

Figures 7C, 7D:
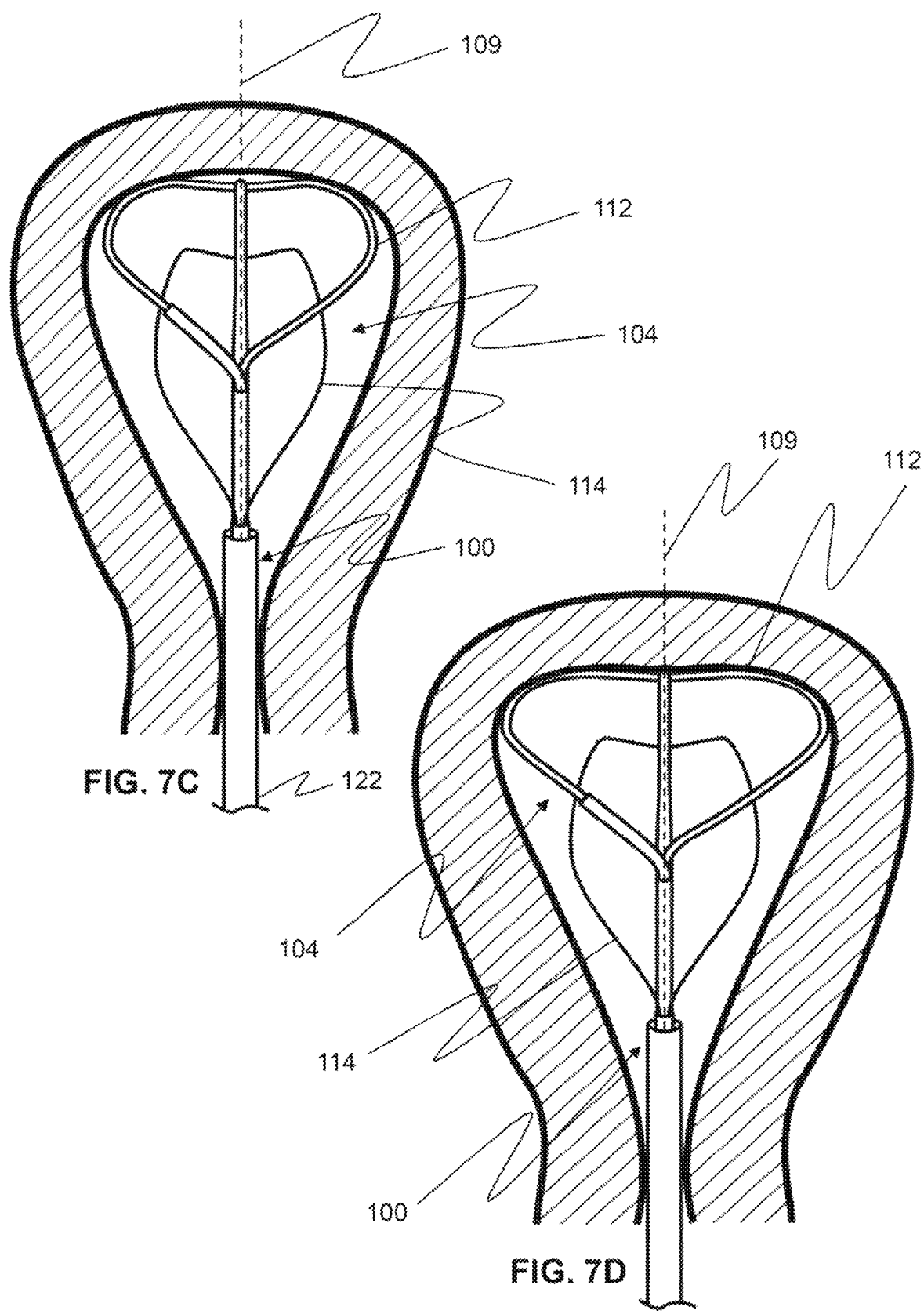
FIGS. 7C and 7D show two steps of a method of ablating the uterine endometrial lining.

FIGS. 7C and 7D show two steps of a method of ablating the uterine endometrial lining using an antenna such as an antenna disclosed in one or more of US 2010/0137857, US 2011/0004205, US 2010/0121319 (incorporated by reference and related patent applications.

In the embodiment shown in FIGS. 7C and 7D, returned power may be measured using any of the embodiments disclosed elsewhere in this document. The user advances the device 100 into the uterine cavity and deploys antenna 104 close to the fundus as shown in FIG. 7C. Thereafter, a test power is sent to the antenna 104. The RP is measured. The position of the antenna 104 may be moved one or more times such that antenna 104 is positioned to push against the fundus as shown in FIG. 7D. Since the uterine cavity is typically widest at the fundal region, antenna 104 is better deployed in FIG. 7D than in FIG. 7C. In one method embodiment, the user moves the antenna distally or proximally at the fundal region while measuring the RP to ultimately position the antenna 104 at the fundal location where the RP is the lowest i.e. to improve the matching of antenna 104 with surrounding material by adjusting the antenna configuration that produces lowest RP. Since the RP is related to the efficiency of the system in delivering microwave energy, this step also helps to increase the energy delivery efficiency of the system while ensuring proper antenna deployment.

Thus, the present invention can be used to determine one or both of: 1. antenna deployment and 2. position within the uterine cavity. This example may involve a setting a returned power limit of 25+/−10%.

One or more portions of antenna 104 such as radiating member 112 and shaping member 114 may mis-deployed because antenna 104 in located within a wrong anatomical location or is still within a sheath. FIGS. 7E-7H show embodiments of mis-deployed antennas wherein at least one of: radiating member 112 and shaping member 114 are mis-deployed. In FIGS. 7E and 7F, antenna 104 is partially within a perforation of the uterus and is partially deployed in the extra-uterine space. In this configuration, the radiating element 112 and shaping element 114 are compressed together. This in turn leads to a change in the electrical length of antenna 104 due to the change in the interaction of the microwave emitted by the radiating element 112 with one or more of: the surrounding medium, the distal region of shielding element 106, antennas dielectrics 116 (if any), floating conductors in the vicinity of radiating member 112 (if any), and other regions of radiating element 112. The change in the electrical length of antenna 104 and the corresponding change in the antenna impedance are detected by an abnormal increase in the returned power (RP) as described previously. Thus, using the present invention, this mis-deployment of the antenna 104 can be detected.

In one embodiment, the system comprising an antenna 104 used for endometrial ablation is designed such that even if antenna 104 is fully deployed in the peritoneal cavity, the imperfect contact of antenna 104 with bowel loops is automatically detected by the system which in turn prevents or stops energy delivery through antenna 104. In one such embodiment, the RP limit of the system is set as 25+/−10%.

FIG. 7G shows an embodiment of antenna 104 that is only partially deployed from an introducing sheath 138. In this configuration, the radiating element 112 and shaping element 114 are compressed together. This will lead to an abnormal change in the RP as described previously. Using the present invention, this partial deployment of the antenna 104 can be detected.

Using a similar concept, the presence of an endometrial ablation antenna 104 inside a false passage or inside the cervical canal (e.g. as shown in FIG. 7H) can be detected.

Using a similar concept, the presence of an antenna 104 inside a narrow or distorted anatomy can be detected.

Figure 7I:
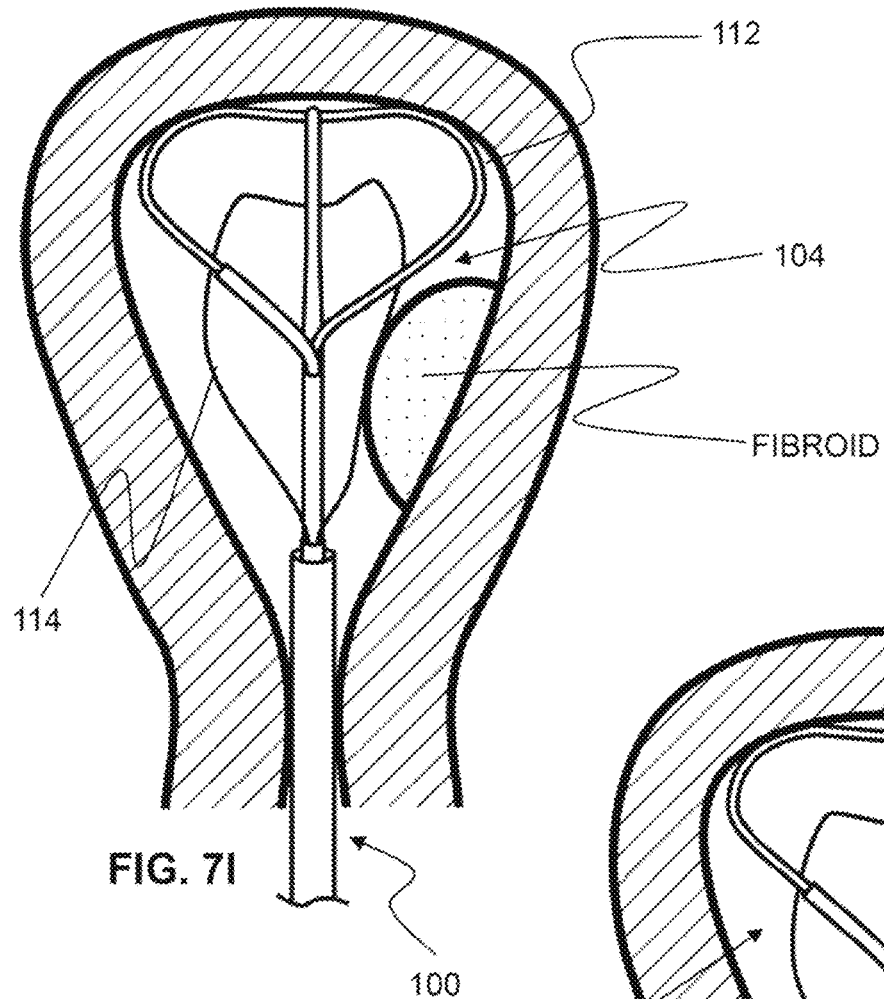
FIGS. 7I and 7J show two deployment embodiments of antennas deployed in cavities with and without a cavity distorting lesion respectively.
Figure 7J:
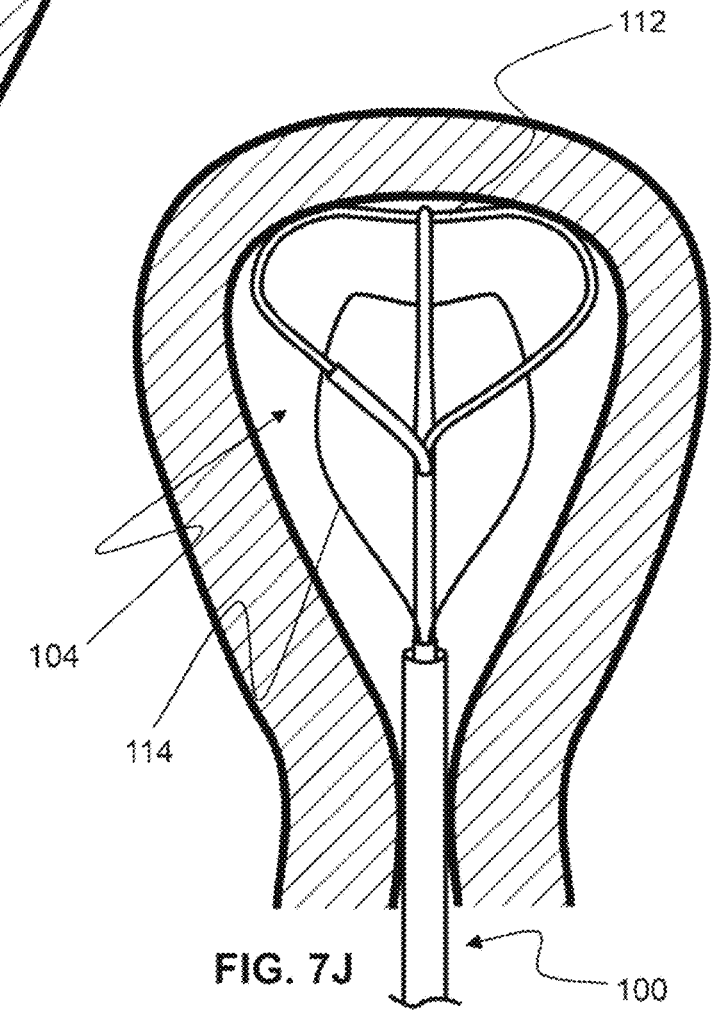

In anatomical regions with lesions such as polyps, fibroids, adhesions, congenital abnormalities, constructions, deposits of calcified substances or plaque, etc. and in anatomy with a non-typical or distorted shape, the deployment of one or more regions of the antenna 104 may be hindered by one or more anatomical regions or materials. These situations might prevent full deployment of the antenna. FIGS. 7I and 7J show two deployment embodiments of antennas deployed in a uterine cavity with and without a cavity distorting lesion respectively. In FIG. 7I, the antenna 104 is distorted by a cavity distorting lesion (e.g. a polyp, fibroid, adhesions or scarring, malignancy, development abnormalities of the Müllerian duct(s), etc.). This has affected the deployment of antenna 104 which in turn will lead to a change in the impedance of antenna 104 as described previously. Thus, the configuration of antenna 104 in FIG. 7I will be different than in the configuration of FIG. 7J wherein the antenna 104 is not distorted. Using the present invention, this deformation of the antenna 104 configuration can be detected. Similar methods may be used for any other antenna 104 disclosed herein on any of the target materials disclosed herein.

In another embodiment, one or more RP measurements are used to determine abnormal orientation (e.g. several flexion, severe anteversion, or severe retroversion) of the uterus and/or the uterine cavity.

Further, one or more parts of the antenna 104 may get stuck to each other during deployment. Also, the antenna 104 may be inadvertently twisted or distorted or bent inside the anatomy. Using the present invention, this deformation of the antenna 104 configuration can be detected. Thereafter, the user may move antenna 104 back and forth or take other measures to ensure that the antenna gets unstuck and is properly deployed. The proper deployment can be determined e.g. by noting a lower or the lowest RP reading. An improper deployment can be determined, for example, by noting a higher RP than expected.

In one embodiment, generator 101 comprises one or more software or hardware elements that comprise a fixed or programmable returned power limit that is used to automatically shut-off or prevent energy delivery to antenna 104 when a mis-deployed antenna 104 or any other system condition disclosed herein is detected by the detection of a RP above the returned power limit. This may be used to prevent energy delivery when the antenna is in a non-desired configuration or when antenna 104 is located in a non-target region of the material. Such feedback can then be used to re-position and/or redeploy antenna 104 at the correct location and configuration. In medical applications, this may be used to increase the safety of a medical procedure by preventing energy delivery when the antenna is in a non-desired configuration or when antenna 104 is located in a non-target region of the anatomy.

One or more RP measurements may be used for determining the proper functioning of antenna 104 and/or the system. During use, antenna 104 may be broken or otherwise damaged or altered to a sufficient extent to affect its performance or safety. For example, one or more of radiating member 112 and shaping member 114 may be broken or otherwise damaged or altered. This can be detected using one or more embodiments of the present invention by detecting a change in the RP.

Similarly, breakage or other damage or alteration to one or more non-antenna regions of device 100, transmission line 102, or generator 101 and the connections between these components can be detected using one or more embodiments of the present invention by detecting a change in the RP.

This information can then be used to take one or more decisions including, but not limited to: terminate the procedure, replace the device, repair the damage, etc.

The method and device embodiments disclosed herein may be used with linear antennas as shown in FIG. 6G, planar antennas as shown in FIG. 6S and three-dimensional antennas as shown in FIG. 6O. One of more radiating elements 112 disclosed herein may be made of one or more non-insulated or insulated elements. Examples of such elements include, but are not limited to: straight or curved segments of metallic elements, elements with a circular or oval shape, elements with a polygonal shape (e.g. triangular, square, rectangular, pentagonal, etc.), multiple elements joined together by an electrically conducting joint(s), multiple elements joined together by a non-electrically conducting joint(s), elements with multiple curves, symmetrically arranged segments of elements, non-symmetrically arranged segments of elements, elements comprising outer coatings or layers of non-conducting materials, elements with a 3-dimensional shape (e.g. helical, tubular, etc.) etc.

Similarly, one of more shaping elements 114 disclosed herein may be made of one or more non-insulated or insulated elements. Examples of such elements include, but are not limited to: straight or curved segments of metallic elements, elements with a circular or oval shape, elements with a polygonal shape (e.g. triangular, square, rectangular, pentagonal, etc.), multiple elements joined together by an electrically conducting joint(s), multiple elements joined together by a non-electrically conducting joint(s), elements with multiple curves, symmetrically arranged segments of elements, non-symmetrically arranged segments of elements, elements comprising outer coatings or layers of non-conducting materials, elements with a 3-dimensional shape (e.g. helical, tubular, etc.) etc.

The antennas 104 disclosed herein may be navigated through the target medium and positioned at one or more positions within the target material using one or more steerable or non-steerable devices. Any of the antennas disclosed herein may comprise one or more attachments or integral elements to enable the user to navigate the antenna 104 through the target medium. Examples of such attachments or elements include, but are not limited to: integral tethers or external pull wires to pull one or more regions of a device or to bend or deflect one or more regions of a device, internal pull wires adapted to bend or deflect one or more regions of a device, one or more elements adapted to be steered by an external navigation modality, etc.

The antennas disclosed herein may be deployed from a slimmer profile insertion configuration to a wide profile working configuration before being placed in the vicinity or inside of the target material. Alternately, the antennas may be deployed from an insertion configuration to a working configuration after being placed in the vicinity or inside of the target material. The deployment of the antennas disclosed herein may be done by one of several methods. The antennas herein may be navigated to the target material in a fully deployed configuration. In another embodiment, an antenna disclosed herein is deployed through an introducer or sheath in which the antenna is in a collapsed, low-profile configuration when inside the introducer and is deployed to a working configuration after the antenna exits the introducer. The antenna may be deployed after the antenna exits the introducer by one or more of: the elastic property of the antenna or its components, the super-elastic property of the antenna or its components, the shape memory property of the antenna or its components, use of a mechanical deployment mechanism for the antenna or its components, use of one or more regions of the target material to change the shape of one or more antenna portions, etc. One or more portions of the antennas herein may be malleable or plastically deformable. This allows the user to shape an antenna to ensure better contact with target material or better navigation through the target material.

The antennas disclosed herein may be conformable to acquire the shape of a portion of the target material or otherwise be shaped by one or more portions of the target material. For example, the antennas disclosed herein may be elastically flexible to conform to the shape of a small cavity or to the shape of an adjacent wall of the cavity into which the antenna is deployed. The antennas disclosed herein may be sized and shaped to approximate the size and shape of a cavity in the target material.

Various additional features may be added to the devices disclosed herein to confer additional properties to the devices disclosed herein. Examples of such features include, but are not limited to one or more lumens, ability to apply a vacuum or suction to the target material, ability to visualize one or more regions of the target material, ability to limit the depth of insertion into the target material, ability to deploy the antenna, ability to connect to a source of energy, etc.

The dimensions or other working parameters of the devices disclosed herein may be adjustable or programmable based on user inputs. The user input may be based on factors such as data from the target material including, but not limited to: shape of the target material, size of the target material, a contour of the target material, the microwave properties of the target material and the desired effect on the target material.

Any of the devices or any introducing catheter or sheath disclosed herein may comprise a fluid transport lumen. The fluid transport lumen may be used for one or more of: evacuating liquids or gases; introducing fluids, contrast agents, cauterizing agents, alcohols, thermal cooling agents, a fluid dielectric medium that surrounds antenna 104, drugs (e.g. antibiotics, chemotherapeutics, etc.), liposome encapsulated drugs, saline and flushing solutions; introducing gases such as carbon dioxide for distending a cavity or detecting perforation of a cavity, applying suction to collapse a target region around the antenna 104; introducing one or more substances that either improve or worsen the matching of the antenna with the surrounding medium, etc. Suction may be applied inside a target to increase the contact of antenna 104 with the target.

Several embodiments of slim and flexible ablation devices are disclosed herein. In medical applications, this allows the user to introduce such ablation devices minimally invasively through small incisions or openings or even non-invasively through natural openings or passageways. Examples of minimally invasive introduction includes percutaneous introduction through the vasculature. Examples of non-invasive introduction includes introduction from the anus, mouth or nostrils into the gastro-intestinal tract, introduction from the vagina into the female reproductive system, introduction from the urethra into the urinary system, introduction from the ear, nostrils or mouth into the ENT system, etc. The devices and methods disclosed herein may be used to ablate diseased tissue or healthy tissue or unwanted tissue in organs or artificially created cavities. The devices disclosed herein may be introduced through laparoscopic, thoracoscopic, cystoscopic, hysteroscopic or other endoscopic openings or instrumentation into or near organs or bodily cavities. The methods disclosed herein may be performed under real-time monitoring e.g. by using one or more of: direct visual observation, hysteroscopy, cystoscopy, endoscopy, laparoscopy, ultrasound imaging, radiological imaging, temperature and other physical parameter monitoring, etc.

Any of the devices disclosed herein may comprise a device transport lumen. The device transport lumen may be used for one or more of: introducing one or more elongate devices in the target material, introducing device 100 over a guidewire or other introducing device and introducing an imaging or visualization device.

Any of the devices disclosed herein may comprise or may be used along with a cooling modality to cool one or more regions of the device or the target material. Examples of such cooling modalities include, but are not limited to: a cooling jacket, inflatable structures inflated with a cooling fluid, gels or other conformable dielectric structures and structures designed to circulate one or more cooling fluids on a surface of antenna 104 and/or the transmission line. The cooling modality may be used to cool one or more of: one or more portions of the target material, a surface of the device, a shaft of the device and an antenna of the device.

Any of the devices disclosed herein may comprise one or more of: an impedance measuring modality, a temperature measuring modality (e.g. a fiber optic thermometry system, a metallic temperature probe) and an electrophysiological signal measuring modality.

In one embodiment of a coaxial cable 102 used for any of the devices 100 herein, coaxial cable 102 is flexible and comprises an inner conductor 108 made of Nitinol with a Ni content of 56%+/−5%. The outer diameter of inner conductor 108 is 0.0172"+/−0.004". Inner conductor 108 has a cladding or plating 120 of a highly conductive metal such as Ag or Au. In one embodiment, inner conductor 108 comprises a silver cladding 120 of thickness 0.000250"+/−0.000050". Cladding 120 in turn is surrounded by dielectric material 110. In one embodiment, dielectric material 110 is made of expanded PTFE with an outer diameter of 0.046"+/−0.005". The dielectric material 110 in turn is surrounded by the outer conductor 106. Outer conductor 106 acts as a shielding element to the microwave signals transmitted by inner conductor 108. Further, outer conductor 106 shields the microwave signals transmitted by inner conductor 108 from external noise. In one embodiment, outer conductor 106 comprises multiple strands of Ag plated Cu. The multiple strands of outer conductor 106 are arranged such that the outer diameter of outer conductor 106 is 0.057"+/−0.005". Outer conductor 106 in turn is covered by an outer jacket 118.

In one embodiment, outer jacket 118 is made of PTFE with an outer diameter of 0.065"+/−0.005". Thus, the outer diameter of coaxial cable 102 is less than about 2 mm. The low profile of flexible coaxial cable 102 has significant advantages since it can be inserted through narrow and/or tortuous paths or lumens. In one embodiment, a shaft comprising coaxial cable 102 is stiffened or strengthened by adding one or more stiffening or strengthening elements such as enclosing stiffening devices jackets, braids, or stiffening layers over coaxial cable 102. In one embodiment, antenna 104 is stiffened or strengthened by adding one or more stiffening or strengthening elements such as jackets, braids or layers within or over antenna 104.

In any of the method and device embodiments disclosed herein, one or more shaping elements 114 may be introduced through a separate device or a separate introduction path to shape the microwave energy profile generated by an antenna 104.

Any of the antennas 104 disclosed herein may comprise or be used in combination with a microwave shielding or absorbing element. The microwave shielding or absorbing element may shield a majority of or a part of the microwave field emitted by antenna 104. Examples of microwave shielding or absorbing elements include, but are not limited to: inflatable or non-inflatable balloons, hollow structures filled with air or a circulating or non-circulating fluid, metallic wires or meshes, metallic films or other flattened structures, gels or other conformable structures, structures filled or wetted with water, structures designed to circulate one or more fluids on the surface of antenna 104, cooling modalities and mechanical spacers made of dielectric materials.

In one such embodiment, a microwave shielding or absorbing element surrounds the whole or part of an antenna 104. The length of the microwave field and the length of the resulting microwave effect by antenna 104 may be changed by sliding the microwave shielding or absorbing element relative to antenna 104. Such microwave shielding or absorbing elements in combination with any antenna 104 disclosed herein may be used to deliver energy to only a portion of a target material disclosed herein. In one such embodiment, microwave shielding or absorbing element is used to ablate a local region of tissue (e.g. a part of the uterine endometrium or a vascular endothelium) or to ablate only a single surface of the tissue (e.g. a single surface of the uterine endometrium).

Any antenna 104 disclosed herein used for medical procedures may be inserted and/or used under endoscopic (e.g. using hysteroscopy, cystoscopy, laparoscopy, flexible endoscopy, etc.) guidance. Any antenna 104 disclosed herein may be inserted and/or used under ultrasonic guidance. Any antenna 104 disclosed herein may be inserted and/or used under radiological (e.g. X-ray or fluoroscopic) guidance.

Even though a majority of the disclosure uses a coaxial cable as an example of a transmission line, an alternate transmission lines for transmitting microwaves may be used. Examples of such alternate transmission lines for transmitting microwaves include, but are not limited to: waveguides, microstrip lines, strip lines, coplanar waveguides and rectax. In such embodiments, the shaping element(s) 114 may be electrically connected directly or indirectly to the shielding element of the transmission line. For example, in a strip line, wherein the shielding element is the combination of the two ground planes, shaping element(s) 114 may be electrically connected directly or indirectly to the combination of the two ground planes. For example, in a hollow metallic waveguide, wherein the shielding element is the electrically conducting wall, shaping element(s) 114 may be electrically connected directly or indirectly to the electrically conducting wall.

In any of the embodiments herein, the whole or portions of antenna 104 may be printed on one or more rigid or flexible, planar or non-planar printed circuit boards.

Several of the embodiments and experiments disclosed herein are described at 0.915 GHz or 2.45 GHz ISM band. Antennas, methods, etc. disclosed herein may be used with or without modifications at other frequencies including, but not limited to ISM bands of 0.434 GHz, 5.8 GHz, etc. The microwave power generator may be magnetron or solid state based. The microwave power generator may be single or multi-channel. The microwave power generator used for during design and/or testing of one or more embodiments disclosed herein comprised a Vector Network Analyzer (Agilent 8753 series) and amplifier modules build in-house using transistors from Freescale Semiconductor (Austin, Tex.). The power measurement was made using a power meter (ML2438A Power Meter, Anritsu Company, Richardson, Tex.). Similar devices and components can be used to design the microwave generator for clinical use with the devices and methods disclosed herein.

Aspects of this invention may be used for medical ablation of tissue in, or adjacent to, the brain, prostate gland, portions of the urinary tract, gall bladder, uterus, uterine adnexae and other portions of the female reproductive tract, regions of the vasculature, intestines and other portions of the lower alimentary tract, stomach and other portions of the upper alimentary tract, liver and other digestive organs, lungs, skin, mucus membranes, kidneys, reproductive organs, joints, or other organs or soft tissues of the body. The devices and methods disclosed herein may be used for the treatment of knee disorders, anterior cruciate ligament instability, vertebral disk injuries and chronic low back pain. The devices and methods disclosed herein may be used several arthroscopic applications such as shrinking the tissues of the ligamentous joint capsule to increase the tension on these ligaments for stabilizing the shoulder joint.

Several devices and methods disclosed herein may be used to treat tissue by microwave thermal ablation. Even though some of the embodiments herein relate to microwave device and methods for ablation of tissue to kill or otherwise damage tissue, the devices and methods disclosed herein may be used to perform a variety of clinically useful actions other than ablation. Examples of such actions include, but are not limited to: 1. causing heat-induced modification of tissue (e.g. desiccation, heat shrinkage or other alteration in the properties of collagen), 2. causing heat-induced modification of an artificially introduced material (e.g. heat induced polymerization of an injected monomer), 3. warming tissue, 4. changing the metabolic activity of tissue (e.g. warming tissue to increase metabolism), 5. causing fat liquefaction e.g. to ease fat extraction during Microwave Assisted Lipoplasty, 6. causing controlled tissue death to debulk tissue for treating conditions such as Obstructive Sleep Apnea or BPH, 6. delivering energy to tissue to change the electrophysiological characteristics of that tissue, and 7. obtaining information about the target anatomy. The microwave emitting device embodiments disclosed herein may be used for medical applications that do not involve ablation of tissue.

Several examples or embodiments of the invention have been discussed herein, but various modifications, combinations, additions, and deletions may be made to those examples and embodiments without departing from the intended spirit and scope of the invention. Thus, any element, component, method step or attribute of one method or device embodiment may be incorporated into or used for another method or device embodiment, unless to do so would render the resulting method or device embodiment unsuitable for its intended use. For example, several embodiments of microwave energy delivery devices 100 may be created by combining antenna 104 of one embodiment with a device feature of another embodiment unless to do so would render the resulting device embodiment unsuitable for its intended use. Any suitable antenna disclosed herein may be used to perform any of the methods disclosed herein. If the various steps of a method are disclosed in a particular order, the various steps may be carried out in any other order unless doing so would render the method embodiment unsuitable for its intended use. A step of one method described herein may be added to or used to replace a step of another method embodiment described herein. A device or method embodiment that is used in one target material or anatomical region may be used in another one target material or anatomical region. Various reasonable modifications, additions and deletions of the described examples or embodiments are to be considered equivalents of the described examples or embodiments.

The invention claimed is:

1. A method of providing microwave energy after introducing an antenna comprising a flexible radiating element into or adjacent to a target material, the method comprising:
   delivering microwave energy through the antenna to the target material;
   obtaining a returned power measurement of the antenna after changing a shape of the antenna;
   detecting a change in an electrical length of the antenna using the returned power measurement and altering delivery of the microwave energy based on the change in electrical length.

2. The method of claim 1, where altering delivery of the microwave energy comprises repositioning the antenna to minimize deformation of the antenna relative to an undeformed shape of the antenna.

3. The method of claim 1, where obtaining the returned power measurement comprises obtaining a plurality of returned power measurements and where detecting the change in the electrical length comprises detecting the change in a shape of the radiating element.

4. The method of claim 1, wherein delivering microwave energy comprises delivering a test microwave energy to the target material, and where the method further comprises delivering a larger dose of microwave energy based on the returned power measurements of the test microwave energy.

5. The method of claim 1, wherein the antenna is connected to a microwave generator and wherein obtaining the returned power measurement comprises measuring a magnitude of microwave energy returned to the generator and calculating the returned power measurement from the magnitude of the microwave energy returned to the generator; wherein calculating comprises dividing the returned power measured by the generator to the forward power measured by the generator.

6. The method of claim 1, further comprising setting a returned power decision limit on a generator connected to the antenna, such that altering the delivery of the microwave energy occurs automatically if the returned power decision limit is met.

7. The method of claim 1, wherein obtaining the returned power measurement occurs after changing a shape of the radiating element.

8. The method of claim 1, wherein the returned power measurement is used to confirm proper deployment of the radiating element in the target material and where altering delivery of the microwave energy comprises repositioning the radiating element.

9. The method of claim 1, wherein the returned power measurement is used to confirm proper deployment of the antenna in the target material and where altering delivery of the microwave energy comprises repositioning the antenna.

10. The method of claim 1, wherein the returned power measurement is used to obtain feedback about a property of the target material.

11. The method of claim 1, wherein the returned power measurement is used to terminate microwave energy delivery.

12. The method of claim 1, wherein the returned power measurement is used for impedance matching of a system comprising the antenna.

13. The method of claim 1, wherein the antenna further comprises a shaping element, and wherein the change in electrical length of is due to the change in the interaction of the microwave energy emitted by the radiating element with the shaping element.

14. The method of claim 1, wherein the antenna is connected to a microwave generator and wherein the method further comprises displaying one or more primary or derived parameters of the microwave energy returned towards the microwave generator.

15. The method of claim 1, further comprising measuring a forward power by a power detector.

16. The method of claim 15, wherein the power detector comprises a diode detector.

17. The method of claim 1, wherein the returned power measurement is made by a power detector.

18. The method of claim 1, further comprising alerting the user about a returned power information.

19. The method of claim 1, further comprising displaying a returned power parameter calculated from a returned power measurement after adjusting for expected microwave energy losses.

20. The method of claim 19, wherein the expected microwave energy losses are one of: losses encountered within a transmission line electrically connected to the antenna and losses encountered within the antenna.

* * * * *